United States Patent
Williams et al.

(10) Patent No.: US 11,890,083 B1
(45) Date of Patent: Feb. 6, 2024

(54) SYSTEMS, APPARATUSES, AND METHODS FOR MAINTAINING CONSTANT PRESSURE OF A PHYSIOLOGICAL SENSOR AGAINST A SUBJECT

(71) Applicant: Tula Health, Inc., Kaysville, UT (US)

(72) Inventors: Josh Williams, American Fork, UT (US); Nicole Winter, Lehi, UT (US); Spencer Talbot, South Jordan, UT (US); Mitchell Slater, Syrcuse, UT (US); Devin Miller, Morgan, UT (US); Ethan Krause, Kaysville, UT (US); Thomas A. Naylor, Provo, UT (US); Paul McMullin, Provo, UT (US); Roger Black, Provo, UT (US); Brian Jensen, Orem, UT (US); Cameron Hernandez, Orem, UT (US)

(73) Assignee: Tula Health, Inc., Farmington, UT (US)

( * ) Notice: Subject to any disclaimer, the term of this patent is extended or adjusted under 35 U.S.C. 154(b) by 261 days.

(21) Appl. No.: 16/994,224

(22) Filed: Aug. 14, 2020

(51) Int. Cl.
*A61B 5/022* (2006.01)
*A61B 5/00* (2006.01)

(52) U.S. Cl.
CPC .............. *A61B 5/022* (2013.01); *A61B 5/681* (2013.01); *A61B 5/6831* (2013.01); *A61B 5/6843* (2013.01); *A61B 5/7275* (2013.01); *A61B 5/7405* (2013.01); *A61B 5/746* (2013.01); *A61B 5/7435* (2013.01); *A61B 2562/0247* (2013.01)

(58) Field of Classification Search
CPC ....... A61B 5/022; A61B 5/681; A61B 5/6831; A61B 5/6843; A61B 5/7275; A61B 5/7405; A61B 5/7435; A61B 5/746; A61B 2562/0247; A61B 5/145
See application file for complete search history.

(56) References Cited

U.S. PATENT DOCUMENTS

| 10,874,348 B1 * | 12/2020 | Han | A61B 5/6843 |
|---|---|---|---|
| 2002/0049389 A1 * | 4/2002 | Abreu | G02C 7/04 |
| | | | 600/318 |
| 2014/0288435 A1 * | 9/2014 | Richards | A61B 5/0205 |
| | | | 600/479 |
| 2016/0278645 A1 * | 9/2016 | Yoon | A61B 5/681 |
| 2016/0374597 A1 * | 12/2016 | Stahmann | A61B 5/7221 |
| | | | 600/309 |

(Continued)

*Primary Examiner* — Eric F Winakur
*Assistant Examiner* — Abid A Mustansir
(74) *Attorney, Agent, or Firm* — Miller IP Law

(57) ABSTRACT

Systems, devices, and methods are described herein for maintaining a physiological sensor at constant pressure against a subject. A system may include a wearable band that is wearable by a subject, a physiological sensor coupled to the wearable band, a pressure sensor coupled to the wearable band, a processor and a user interface. The physiological sensor may be positioned along an inside surface of the wearable band, embedded in the wearable band, or otherwise positioned in the band to be adjacent to the subject as the subject wears the wearable band. The pressure sensor may directly or indirectly measure a pressure of the physiological sensor against the subject. The processor may generate an alert when a pressure measurement for the physiological sensor against the subject is outside a specified range. The user interface may present the alert to the subject.

20 Claims, 49 Drawing Sheets

(56) References Cited

U.S. PATENT DOCUMENTS

2017/0119293 A1* 5/2017 Matsui ............... A61B 5/14551
2020/0077955 A1* 3/2020 Shui .................... A61B 5/7228
2021/0345973 A1* 11/2021 Ko ..................... A61B 5/02116

* cited by examiner

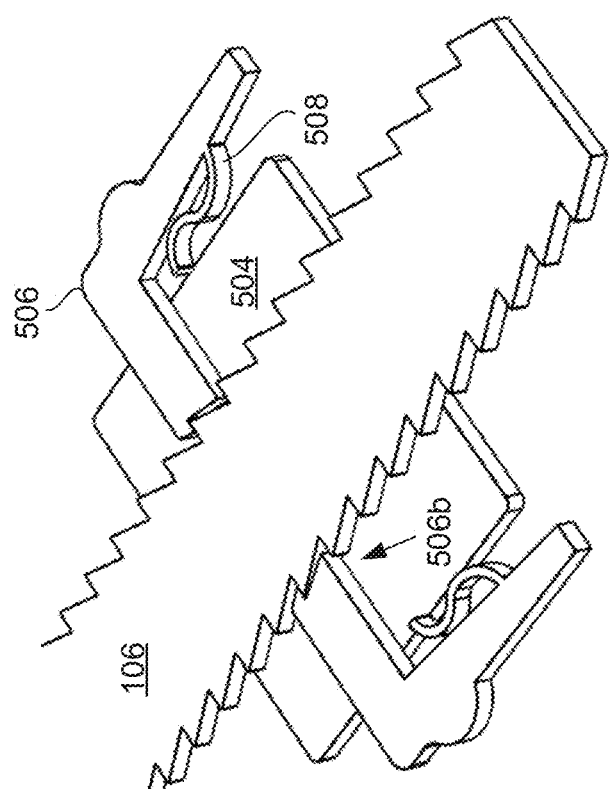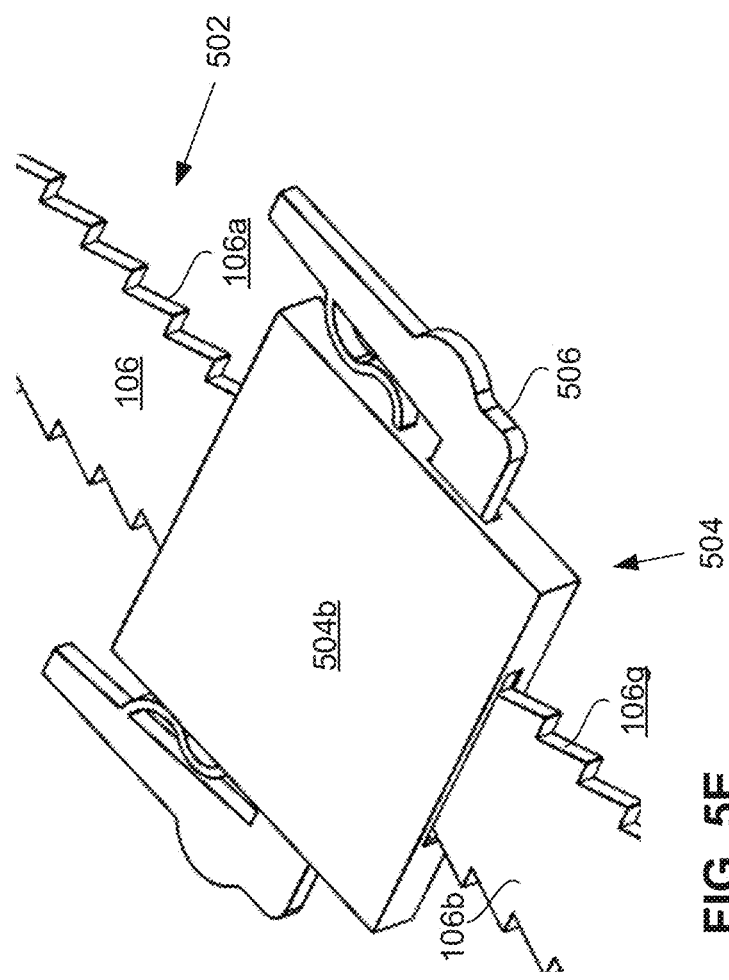

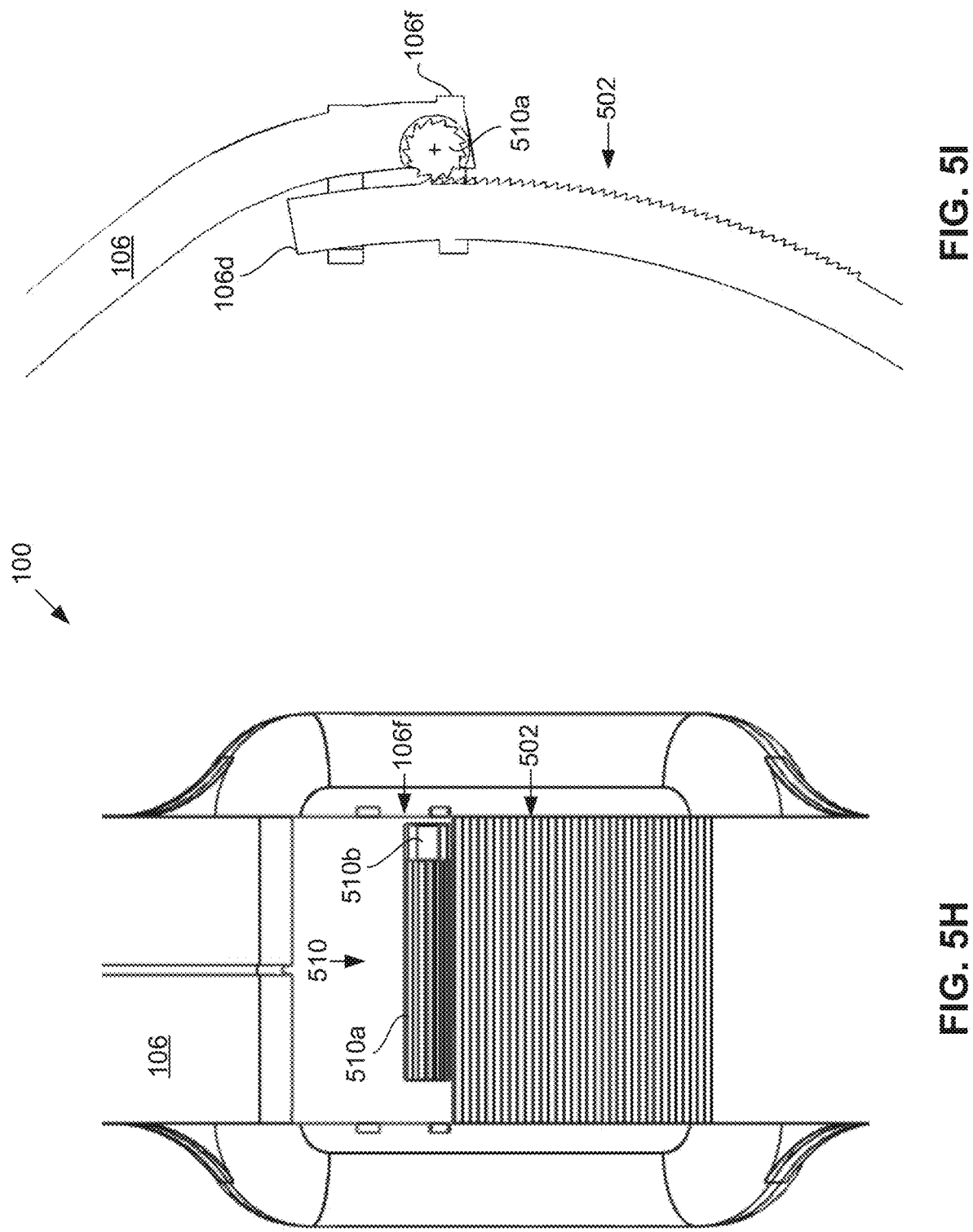

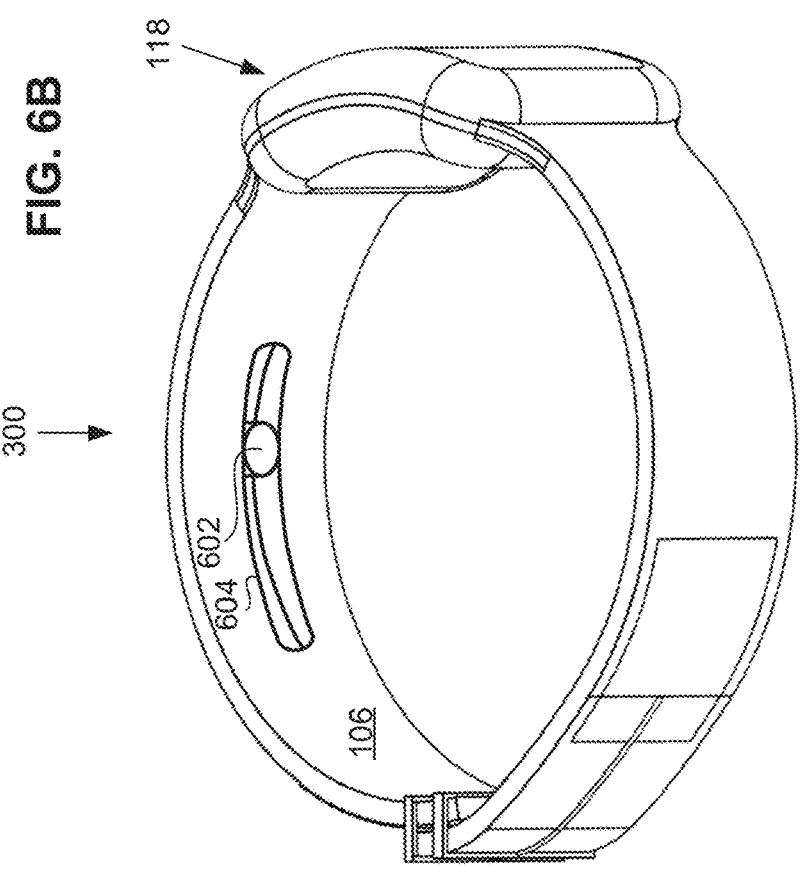
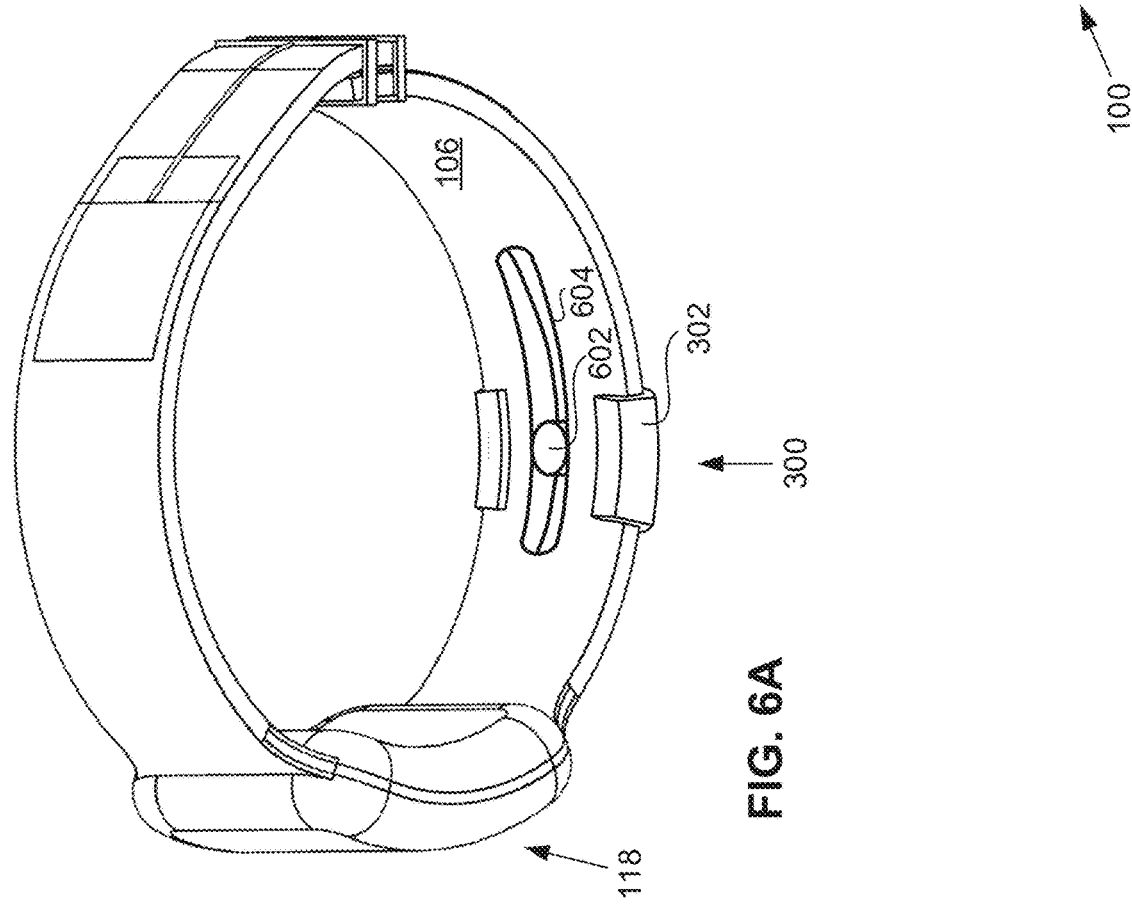

900
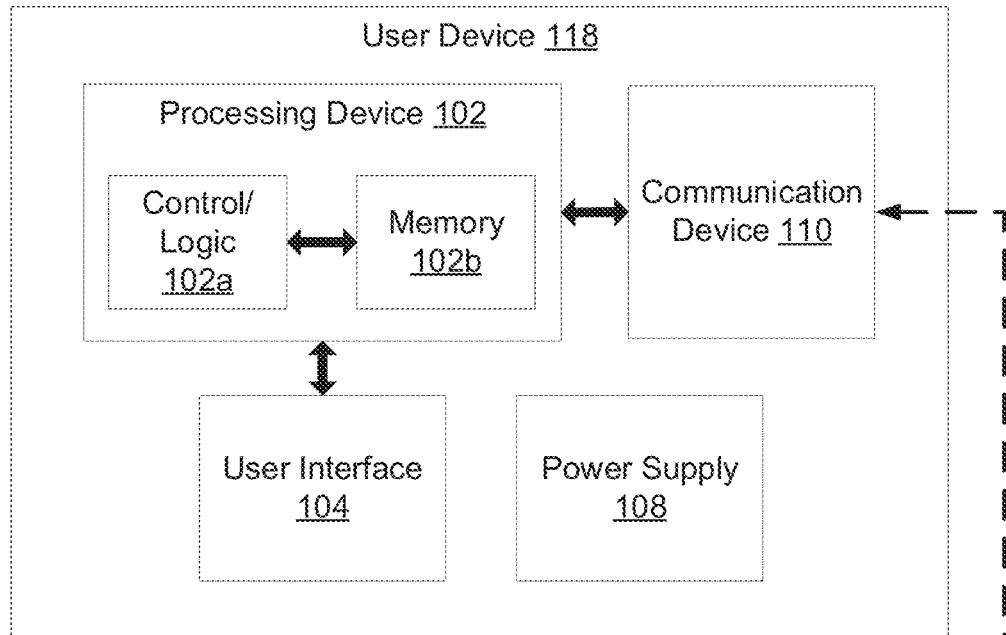
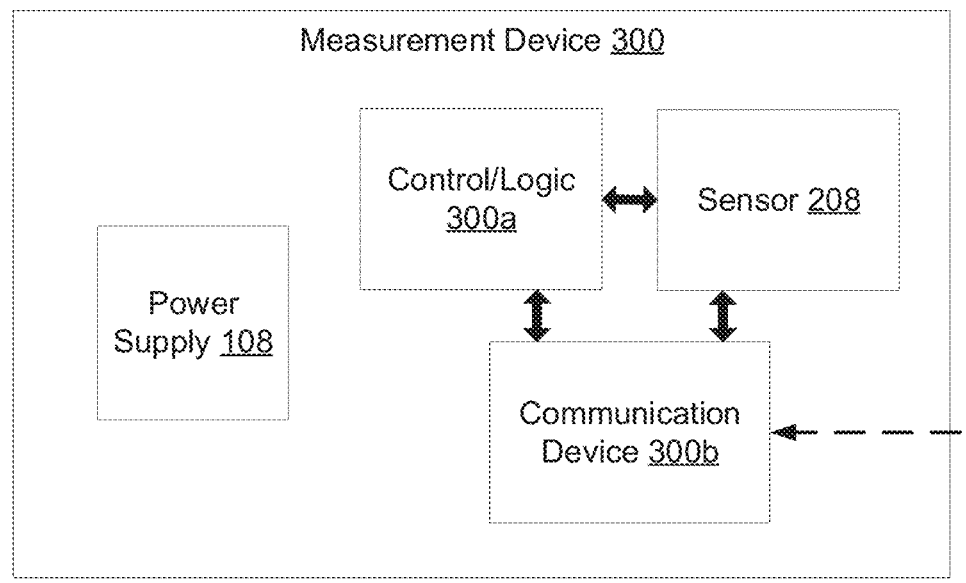
FIG. 9

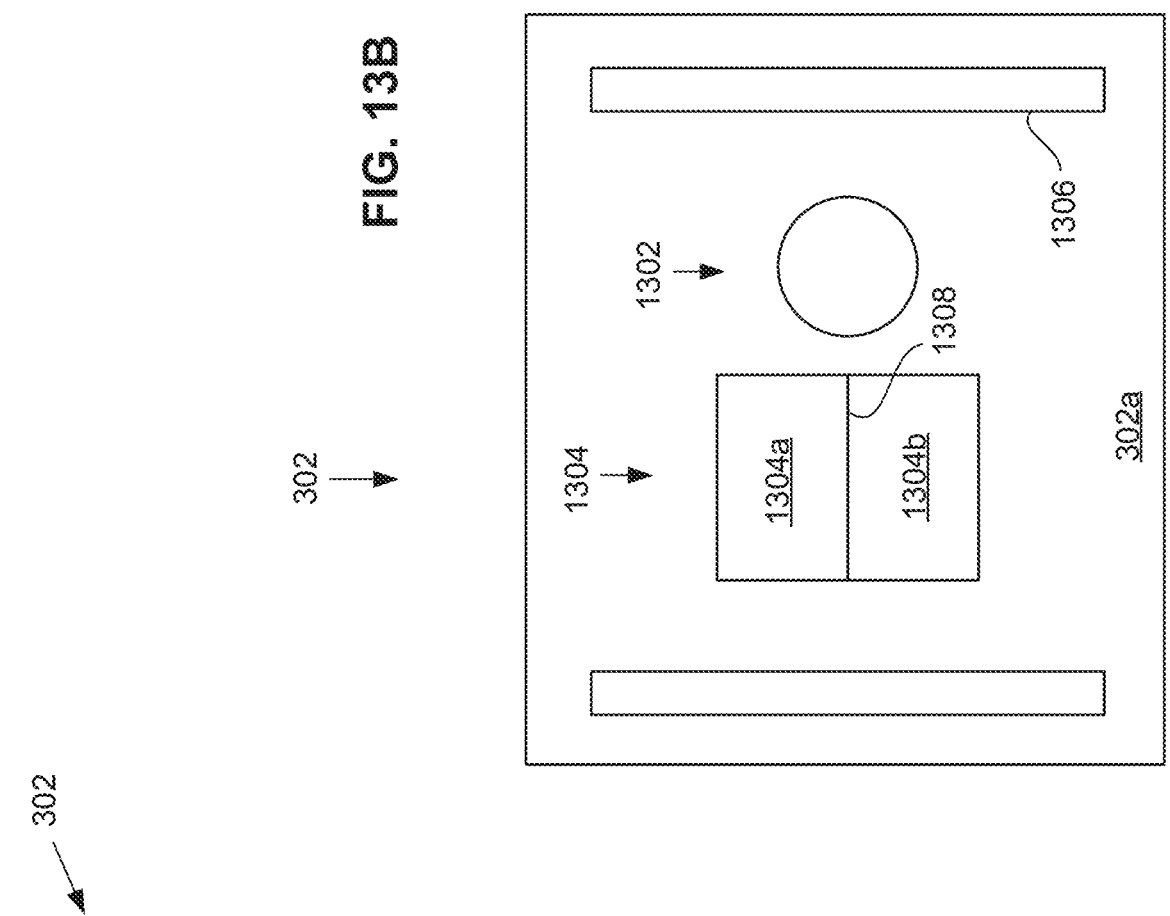
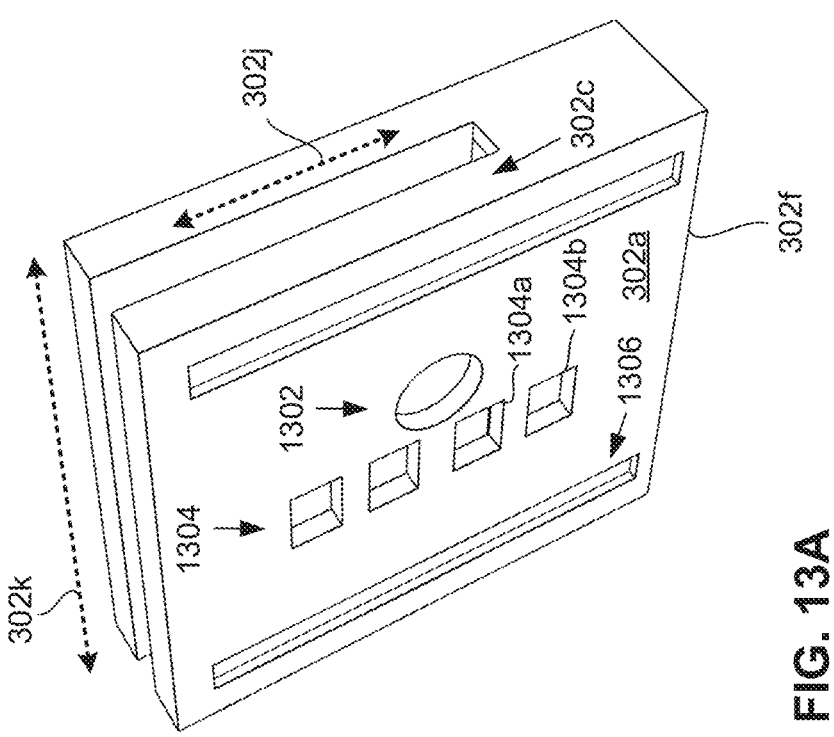

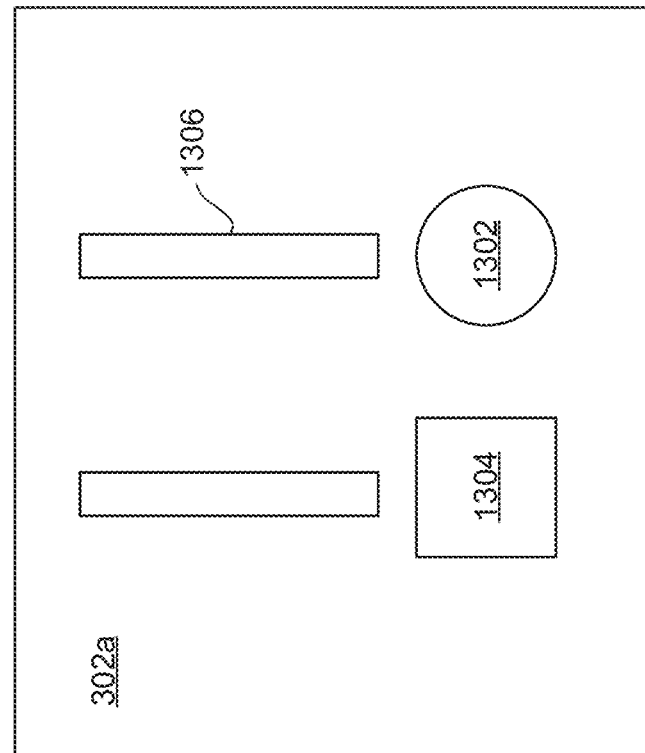
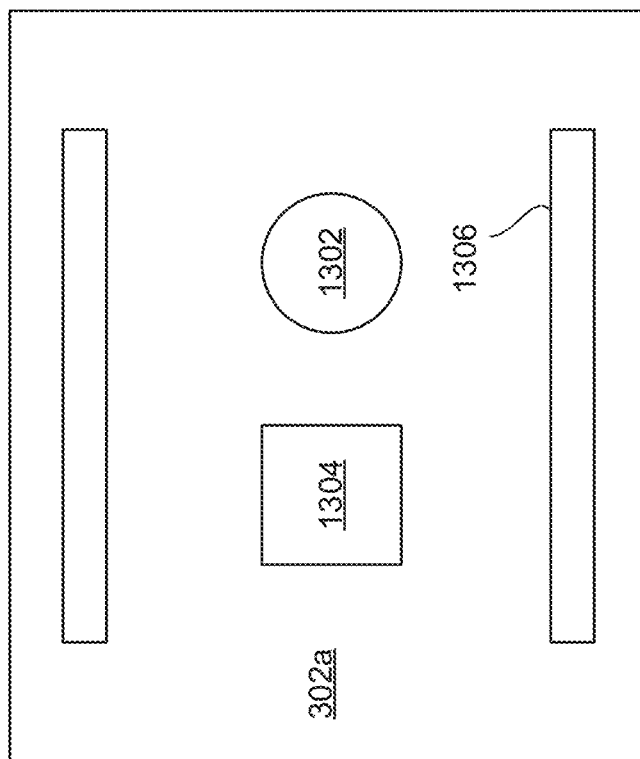
FIG. 13D
FIG. 13C

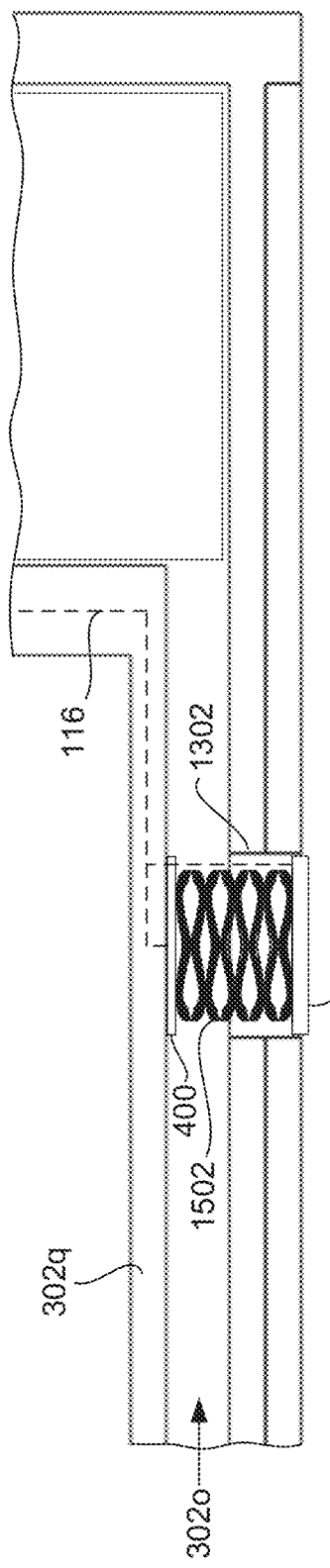
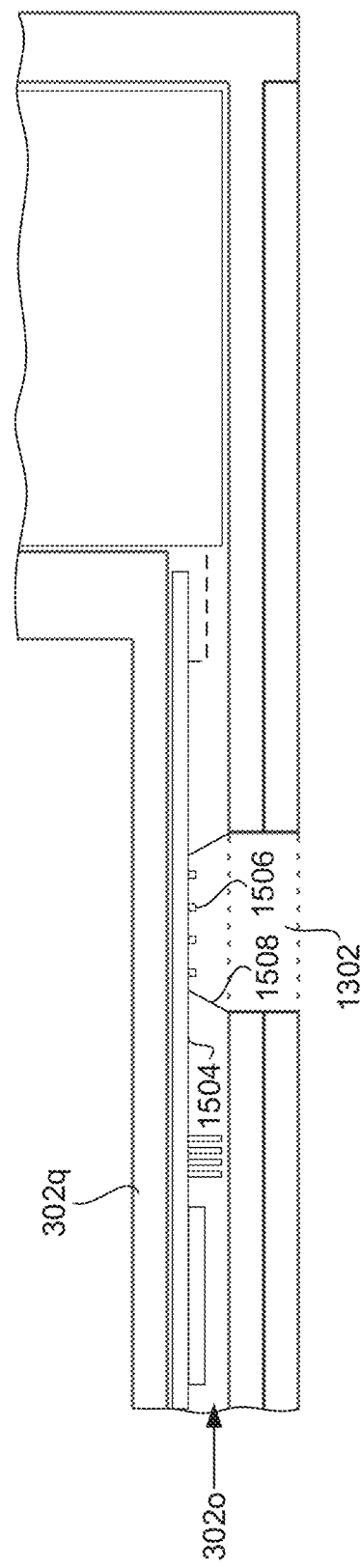

SYSTEMS, APPARATUSES, AND METHODS FOR MAINTAINING CONSTANT PRESSURE OF A PHYSIOLOGICAL SENSOR AGAINST A SUBJECT

BACKGROUND

The symptoms of a chronic health condition can be a significant factor in the quality of life for an individual experiencing the chronic health condition. Proper management of the chronic health condition can lead to outcomes which greatly improve the individual's quality of life compared to outcomes when the chronic health condition is improperly and/or inadequately managed. For example, proper management of a chronic health condition may include taking regular measurements of various body functions, either directly or indirectly. Such measurements may provide critical information necessary for proper management of the chronic health condition. Obtaining measurements may be challenging and/or time-consuming, and the individual may accordingly be unlikely to obtain the measurements. Without the measurements, the chronic health condition may be improperly and/or inadequately managed, leading to poor outcomes for the individual where the individual experiences serious, even life-threatening symptoms of the chronic health condition.

BRIEF DESCRIPTION OF DRAWINGS

The present description will be understood more fully when viewed in conjunction with the accompanying drawings of various examples of systems, methods, and apparatuses for optimizing a physiological measurement taken from a subject. The description is not meant to limit the systems, methods, and apparatuses to the specific examples. Rather, the specific examples depicted and described are provided for explanation and understanding of systems, methods, and apparatuses for optimizing a physiological measurement taken from a subject. Throughout the description, the drawings may be referred to as drawings, figures, and/or FIGS.

FIG. 5E illustrates a first perspective view of a second type of the cantilevered pawl, according to an embodiment.

FIG. 5F illustrates a second perspective view of the second type of the cantilevered pawl, according to an embodiment.

FIG. 5H illustrates a top cross-section view of a motorized band tightening mechanism, according to an embodiment.

FIG. 5I illustrates a side cross-section view of the motorized band tightening mechanism, according to an embodiment.

FIG. 6A illustrates a perspective view of the wearable device having a moveable sensor attached to a measurement device housing and positioned in a slot in the band, according to an embodiment.

FIG. 6B illustrates a perspective view of the wearable device having the moveable sensor in the slot in the band, according to an embodiment.

FIG. 9 illustrates a system diagram of the adjustable measurement device remotely networked to the user device, according to an embodiment.

FIG. 13A illustrates an underside of the adjustable measurement device, according to an embodiment.

FIG. 13B illustrates another arrangement of the underside of the adjustable measurement device, according to an embodiment.

FIG. 13C illustrates a third arrangement of the underside of the housing of the adjustable measurement device, according to an embodiment.

FIG. 13D illustrates a fourth arrangement of the underside of the housing of the adjustable measurement device, according to an embodiment.

FIG. 15B illustrates a zoomed-in view of the cross-section illustrated in FIG. 15A, according to an embodiment.

FIG. 15C illustrates a zoomed-in view of the cross-section illustrated in FIG. 15A including light piping, according to an embodiment.

DETAILED DESCRIPTION

Figure 1A:
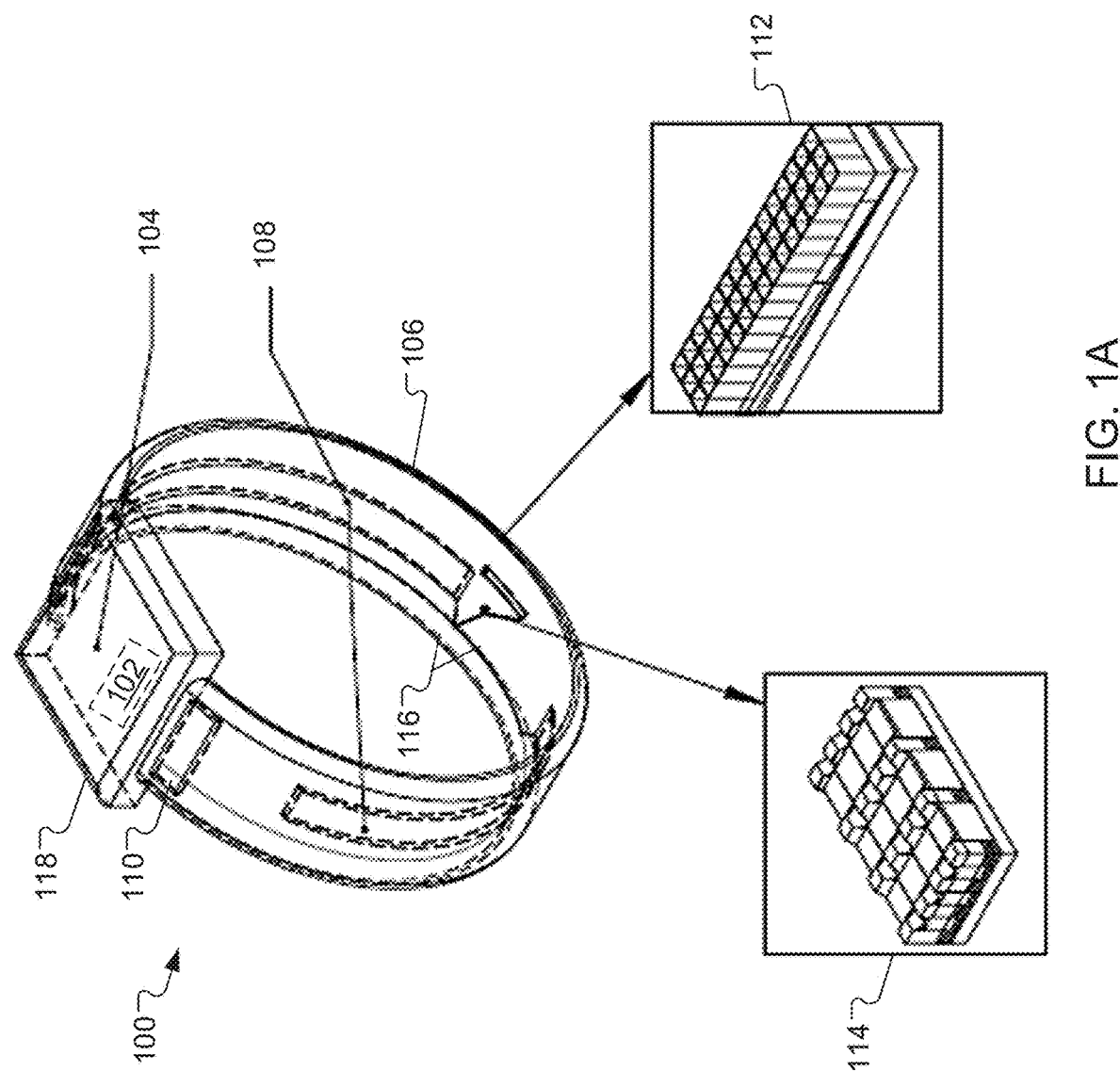
FIG. 1A illustrates a wearable device with incorporated sensors, according to an embodiment.

Systems, methods, and apparatuses for optimizing a physiological measurement taken from a subject as disclosed herein will become better understood through a review of the following detailed description in conjunction with the figures. The detailed description and figures provide merely examples of the various embodiments of systems, methods, and apparatuses for maintaining a sensor at constant pressure against a subject. Many variations are contemplated for different applications and design considerations; however, for the sake of brevity and clarity, all the contemplated variations may not be individually described in this detailed description. Those skilled in the art will understand how the disclosed examples may be varied, modified, and altered and still fall within the scope of the examples described herein.

Throughout this detailed description, examples of various systems, methods, and apparatuses for optimizing a physiological measurement taken from a subject are provided. Related elements in different examples may be identical, similar, or dissimilar in the examples. For the sake of brevity and clarity, the related elements may not be redundantly explained in the various examples. Instead, the use of a same, similar, and/or related element names and/or reference characters may cue the reader that an element in one example with a given name and/or associated reference character may be similar to another related element with the same, similar, and/or related element name and/or reference character in an example explained elsewhere herein. Elements specific to a given example may be described regarding that particular example. A person having ordinary skill in the art will understand that a given element need not be identical to the specific portrayal of a related element in any given figure or example to share features of the related element.

As used herein "same" means sharing all features and "similar" means sharing a substantial number of features or sharing materially important features even if a substantial number of features are not shared. As used herein "may" should be interpreted in a permissive sense and should not be interpreted in an indefinite sense. Additionally, use of "is" regarding examples, elements, and/or features should be interpreted to be definite only regarding a specific example and should not be interpreted as required regarding every variation of the systems, methods, and/or apparatuses disclosed herein. Furthermore, references to "the disclosure" and/or "this disclosure" refer to the entirety of the writings of this document and the entirety of the accompanying illustrations, which extends to all the writings of each subsection of this document, including the Title, Background, Brief description of the Drawings, Detailed Description, Claims, Abstract, and any other document and/or resource incorporated herein by reference.

As used herein regarding a list, "and" forms a group inclusive of all the listed elements. For example, an embodiment described as including A, B, C, and D is an embodiment that includes A, includes B, includes C, and also includes D. As used herein regarding a list, "or" forms a list of elements, any of which may be included. For example, an embodiment described as including A, B, C, or D is an embodiment that includes any of the elements A, B, C, and D but not necessarily all of the elements. Unless otherwise stated, an embodiment including a list of alternatively-inclusive elements does not preclude other embodiments that include various combinations of some or all of the alternatively-inclusive elements. An embodiment described using a list of alternatively-inclusive elements includes at least one element of the listed elements. However, an embodiment described using a list of alternatively-inclusive elements does not preclude another embodiment that includes all of the listed elements. And, an embodiment described using a list of alternatively-inclusive elements does not preclude another embodiment that includes a combination of some, but not necessarily all, of the listed elements. As used herein regarding a list, "and/or" forms a list of elements inclusive alone or in any combination. For example, an embodiment described as including A, B, C, and/or D is an embodiment that may include: A alone; A and B; A, B and C; A, B, C, and D; and so forth. The bounds of an "and/or" list are defined by the complete set of combinations and permutations for the list.

Where multiples of a particular element are shown in a FIG., and where it is clear that the element is duplicated throughout the FIG., only one label may be provided for the element despite multiple instances of the element being present in the FIG. Accordingly, other instances in the FIG. of the element having identical or similar structure and/or function may not be redundantly labeled. A person having ordinary skill in the art will recognize, based on the disclosure herein, redundant and/or duplicated elements of the same FIG. Despite this, redundant labeling may be included where helpful in clarifying the structure of the depicted example embodiments.

Conventional apparatuses for maintaining a sensor against a subject may include a device such as a smartwatch. A smartwatch may be worn by the subject as the subject goes about his or her every-day activities. In other cases, sensors may be used in clinical settings such as in a lab, doctor's office, a hospital, and so forth. In such a setting, a sensor may be held on the subject by, for example, taping the sensor to the subject. In some cases, the sensor may be clamped on to the subject, such as in a case where a pulse oximetry sensor is clamped to the subject's finger. However, various sensors may be inaccurate when held against a subject with the wrong amount of pressure. The wrong amount of pressure may lead to additional noise in a sensor signal, inaccurate readings, or failures to obtain readings altogether. Furthermore, in various cases, a sensor may be configured to take a measurement from a specific position on a subject. If the sensor is not aligned at the specific position on the subject, then the sensor will not accurately measure a physiological characteristic the sensor is designed to measure. Smartwatches may be insufficient to maintain the sensor at a reliable pressure against the subject or in a consistent position on the subject. Tape may be inconvenient, uncomfortable, and may not hold the sensor at a reliable pressure as the subject moves during the subject's daily activities. Tape may not be effective when the subject sweats or otherwise engages in an activity where the subject's skin may become damp and/or wet.

Systems, methods, and apparatuses are described herein that address at least some of the problems described above. In various embodiments, systems, methods, and apparatuses are described herein for optimizing a measurement taken by a physiological sensor such as by maintaining a sensor against a subject at an approximately constant pressure and/or in an approximately constant position. An apparatus for maintaining the sensor at the constant pressure against a subject may include a wearable band. The wearable band may be secured on the subject by a mechanism that allows for fine-tuning of a pressure of the band on the subject. The sensor may be pressed against the subject by an elastic coupling mechanism that is attached to the wearable band or a housing. The housing may be attached to the band. The housing may be movably attached to the band such that, as the band remains secure and in a constant position and/or orientation on the subject, the housing can be moved relative to the subject and/or the band. A pressure sensor may detect a pressure of the wearable band on the subject or a pressure of the sensor against the subject. The band may include a slot through which the sensor extends. The sensor may be pressed against the subject through the slot. The sensor may be electronically coupled to a processing device. The processing device may be programmed to identify an optimal position of the sensor against the subject, such as in alignment with a physiological structure of the subject. The processing device may be programmed to identify an optimal pressure and/or pressure range of the sensor against the subject. The processor may be programmed to communicate information with the subject, such as via a user device and/or a user interface. The information may be associated with the position of the sensor, the pressure of the wearable band on the subject, and/or the pressure of the sensor against the subject.

FIG. 1A illustrates a wearable device 100 with incorporated sensors 112 and/or 114, according to an embodiment. Some of the features in FIG. 1A may be the same as or similar to some of the features in the other FIGS. described herein as noted by same and/or similar reference characters, unless expressly described otherwise. Additionally, reference may be made to features shown in any of the other FIGS. described herein and not shown in FIG. 1A.

The wearable device 100 may be configured to take physiological measurements from a subject. The wearable device 100 may include a user device 118 and a band 106 that are configured to (e.g. in shape, size, material, and so forth) attach to a body of the subject. The wearable device 100 may, for example, be an electronic wrist-worn device such as a smartwatch that may be configured to attach to a wrist or arm of the subject. The wearable device 100 may be attached to a head of the subject using a headband, to a chest of the subject using a chest band, to an ankle of the subject using an ankle band, or otherwise attached to a body of the subject using a sweatband, bandage, band, watch, bracelet, ring, adherent, and/or other attachments and connections.

As used herein, "subject" may be used to refer to an individual from whom a physiological measurement may be taken and/or who may wear the wearable device 100 and/or the other devices described herein. The subject may be another person who may use the wearable device 100 and/or the other devices described herein but from whom the measurements were not taken. For example, a healthcare professional such as a doctor, physician's assistant, and/or nurse may use information generated by the wearable device 100 and/or the other devices described herein. In general, the subject may be the person from whom the physiological measurements are taken and/or a person who may use the wearable device 100, the other devices described herein, and/or the information related to the physiological measurements.

The wearable device 100 may include a processing device 102, a user interface 104, the band 106, a power source 108, the first sensor 112, and/or the second sensor 114. The processing device 102 and the user interface 104 may be integrated into the user device 118 of the wearable device 100. The power source 108, the first sensor 112, and/or the second sensor 114 may be integrated into the band 106 of the wearable device 100. The band 106 may include one or more cavities that the power source 108, the first sensor 112, and/or the second sensor 114 may be stored in. The band 106 may be formed around, molded around, and/or overmolded around the power source 108, the first sensor 112, and/or the second sensor 114. The power source 108, the first sensor 112, and/or the second sensor 114 may be connected to the processing device 102 by one or more electrical trace(s) or circuit(s) 116 (e.g. a flexible circuit board, copper traces, interconnects, and so forth).

The processing device 102 may provide an output based on an input. The processing device 102 may, for example, be a central processing unit, a graphics processing unit, a vision processing unit, a tensor processing unit, a neural processing unit, a physics processing unit, a digital signal processor, an image signal processor, a synergistic processing element, a field-programmable gate array, a sound chip, a microprocessor, a multi-core processor, and so forth.

The first sensor 112 may include a miniaturized spectrometer. The second sensor 114 may include a miniaturized impedance sensor. The first sensor 112 and/or the second sensor may include a temperature sensor, a viscosity sensor, an ultrasonic sensor, a humidity sensor, a heart rate sensor, a dietary intake sensor, an electrocardiogram (EKG) sensor, a galvanic skin response sensor, a pulse oximeter, an optical sensor, and so forth. The wearable device 100 may include other sensors integrated into or attached to the band 106 or the user device 118. The wearable device 100 may be communicatively coupled to one or more remote and/or external devices such as sensors of other devices or third-party devices. The first sensor 112 and/or the second sensor 114 may be configured to take measurements from a subject non-invasively, such as by electrical and/or optical interrogation, and so forth.

The first sensor 112 and/or the second sensor 114 may be electronically and/or communicatively coupled to the processing device 102. The processing device 102 may be configured to manage and/or control the first sensor 112, the second sensor 114, the power source 108, the user interface 104, and so forth. The processing device 102 may control a frequency or rate over time that the first sensor 112 and/or the second sensor 114 take measurements, a wavelength or optical frequency at which the first sensor 112 and/or the second sensor 114 take measurements, a power consumption level of the first sensor 112 and/or the second sensor 114, a sleep mode of the first sensor 112 and/or the second sensor 114 and so forth. The processing device 102 may control and/or adjust measurements taken by the first sensor 112 and/or the second sensor 114 take measurements to remove noise, increase a signal to noise ratio (SNR), dynamically adjust the number of measurements taken over time, enhance a signal amplitude, enhance one or more other signal qualities, and so forth.

The power source 108 may include a battery, a solar panel, a kinetic energy device, a heat converter power device, a wireless power receiver, and so forth. The processing device 102 may be configured to (e.g. may be programmed to and/or include hardware to) transfer power from the power source 108 to the processing device 102, the user interface 104, the first sensor 112, the second sensor 114, other devices or units of the wearable device 100, and so forth. The processing device 102 may be configured to regulate an amount of power provided from the power source 108 to the processing device 102, the user interface 104, the first sensor 112, the second sensor 114, and/or other devices or units of the wearable device 100. In another embodiment, the wearable device 100 may include a power receiver to receive power to recharge the power source 108. For example, the power receiver may include a wireless power coil, a universal serial bus (USB) connector, a thunderbolt connector, a mini USB connector, a micro USB connector, a USB-C connector, and so forth. The power receiver may be coupled to the processing device 102, the power source 108, and so forth.

The processing device 102 may be configured to regulate an amount of power provided from the power receiver to the power source 108. The processing device 102 may include a power management unit configured to control battery management, voltage regulation, charging functions, alternating current to direct current conversion, voltage scaling, power conversion, dynamic frequency scaling, pulse-frequency modulation, pulse-width modulation, amplification, and so forth.

The processing device 102 may be electronically and/or communicatively coupled to a communication device 110. The communication device 110 may be configured to send and/or receive data via a cellular communication channel, a wireless communication channel, a Bluetooth® communication channel, a radio communication channel, a WiFi® communication channel, a USB communication channel, an fiber-optic communication channel, and so forth.

The processing device 102 may include a data processor, a data storage device, a communication device, a graphics processor, and so forth. The processing device 102 may be configured to receive measurement data from the first sensor 112 and/or the second sensor 114. The processing device 102 may be configured to process the measurement data and display information associated with the measurement data via the user interface 104. The processing device 102 may be configured to communicate the measurement data to another device. The other device may process the measurement data and provide information associated with the measurement data to the subject or another individual. The other device may process the measurement data and provide results, analytic information, instructions, and/or notifications to the processing device 102 to provide to the subject. The wearable device 100 may communicate information associated with the measurement data or information related to the measurement data to a subject via the user interface 104. The user interface 104 may include a visual display, an input mechanism, a buzzer, a vibrator, a speaker, a microphone, and so forth.

The wearable device 100 may be part of a system connected to other devices. For example, the wearable device 100 may be configured to send and/or receive data with another device such as another measurement device, another user device, a remote server, a computer, a smartphone, and so forth. The wearable device 100 may be configured to receive data from another measurement device, aggregate the received data with measurement data from the first sensor 112 and/or the second sensor 114, analyze the aggregated data, and provide information and/or notifications associated with the analyzed data.

Figure 1C:
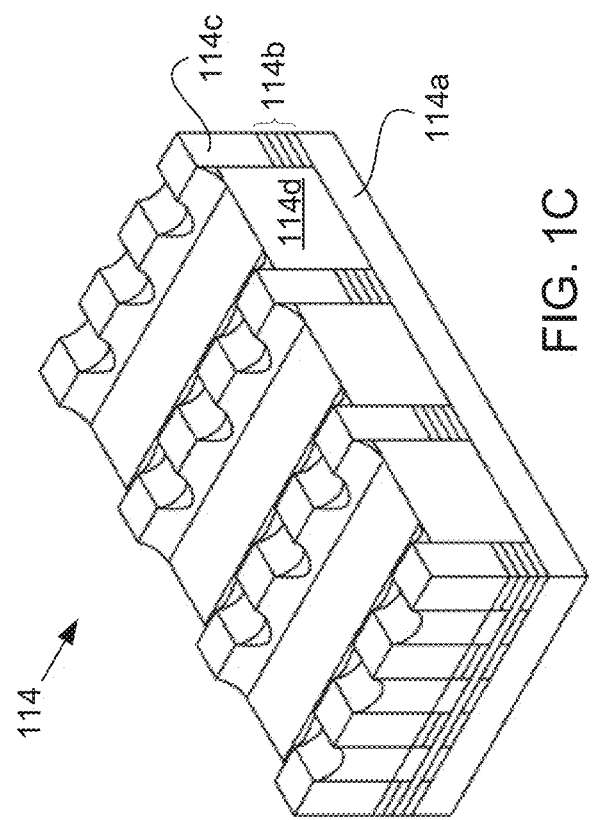
FIG. 1C illustrates a perspective view of a second sensor, according to an embodiment.
Figure 1B:
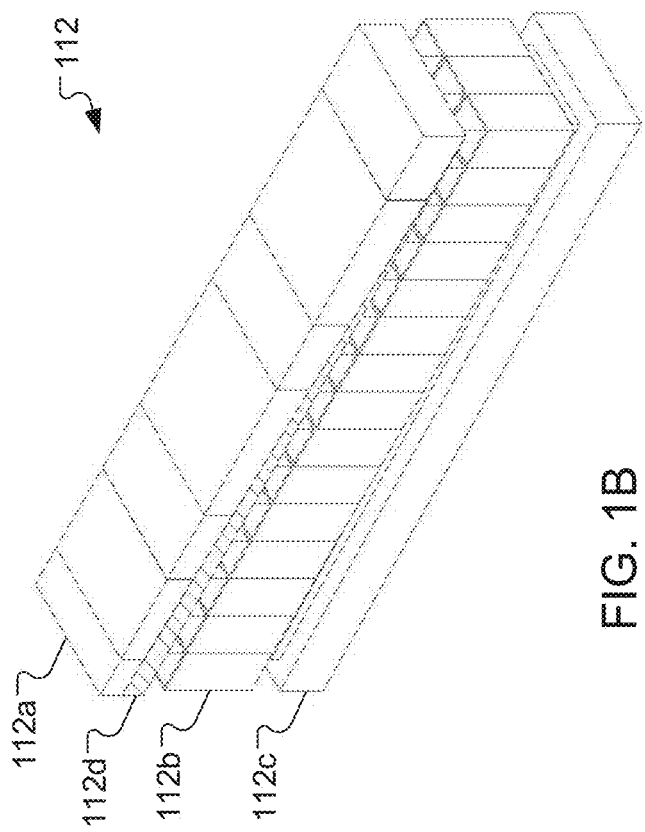
FIG. 1B illustrates a perspective exploded view of a first sensor, according to an embodiment.

FIG. 1B illustrates a side perspective exploded view of the first sensor 112, according to an embodiment. Some of the features in FIG. 1B may be the same as or similar to some of the features in the other FIGS. described herein as noted by same and/or similar reference characters, unless expressly described otherwise. Additionally, reference may be made to features shown in any of the other FIGS. described herein and not shown in FIG. 1B.

The first sensor 112 may include a miniaturized spectrometer. The first sensor 112 may include a filter 112a, a collimator 112b, and/or an optical sensor 112c. The filter 112a may include an optical filter, such as a variable filter, a linear variable filter, an absorptive filter, a dichroic filter, a monochromatic filter, an infrared filter, an ultraviolet filter, a neutral density filter, a long-pass filter, a band-pass filter, a short-pass filter, a guided-mode resonance filter, a metal mesh filter, a polarizer filter, an arc welding filter, a wedge filter, and so forth. The filter may include a Fabry-Perot Etalon filter.

The filter 112a may include a linear variable filter. The linear variable filter may allow for selecting which wavelengths strike the optical sensor 112c at a specific position on the optical sensor 112c. This may allow the processing device 102 to, in turn, distinguish the relative intensities of wavelengths reflected from a tissue to determine which wavelengths are most strongly reflected from the tissue relative to an initial intensity of those wavelengths as emitted from a light source. The processing device 102 may determine, based on the reflected wavelengths, one or more parameters, constituents, and/or conditions of the tissue. For example, light having a first wavelength may strike a first region of the optical sensor 112c corresponding to a first region of the filter 112a. The first wavelength may correspond to a constituent of the subject's blood. The optical sensor 112c may communicate the intensity of the first wavelength to the processor. The processor may process the first wavelength based on an emitted intensity of the wavelength, an expected attenuation of the wavelength, and/or other attenuation factors to determine an amount of the constituent in the subject's blood. Different constituents of the subject's blood may transmit and/or reflect wavelengths of light at different intensities. The filter 112a may pass different wavelengths to different positions on the optical sensor 112c. The optical sensor 112c may pass the intensities of the corresponding wavelengths to the processor, and the processor may determine an amount of the blood constituent based on the relative intensities of the wavelengths.

The filter 112a may include an absorptive filter. The absorptive filter may be formed to have distinct cutoff edges between regions of the absorptive filter corresponding to different wavelength ranges. The absorptive filter may be manufactured of a durable and/or flexible material. The filter 112a may include a dichroic filter (i.e. an interference filter). The dichroic filter may be variable. The dichroic filter may allow for precise selection of wavelengths to be passed through the filter 112a. For example, the dichroic filter may have a transmission profile with a narrow peak, such as a full-width half max wavelength range of 50 nm, 40 nm, 30 nm, 25 nm, 20 nm, 10 nm, 5 nm, and/or 1 nm. The dichroic filter may be implemented in embodiments where the filter 112a is incorporated into a sensor for measuring sensitive phenomena. The sensitive phenomena may include various physiological parameters, conditions, and/or constituents for which small-percentage changes, such as less than or equal to a 50 percent change, result in dramatically different outcomes. For example, the sensitive phenomenon may include a blood acidity level. A healthy blood acidity may include a pH of 7.4. A blood pH less than or equal to 6.8 or greater than or equal to 7.8 may result in irreversible cell damage. As another example, the sensitive phenomenon may include bone density.

The filter 112a may include a grism. The filter 112a may include a prism coupled to a diffraction grating. The grism and/or the coupled prism and diffraction grating may be referred to as the grism. The prism may include a dispersion prism and/or a prismatic sheet, such as a Fresnel prism. The diffraction grating may include a ruled grating, a holographic grating, a transmission grating, a reflective grating, a blazed holographic grating, a concave grating, an aberration-corrected concave grating, a constant deviation monochromator concave grating, a Rowland type concave grating, a blazed holographic concave grating, a sinusoidal holographic grating, a sinusoidal ruled grating, a pulse compression grating, and so forth. The diffraction grating may include a volume phase holographic grating. The diffraction grating may diffract impinging light along one dimension or along two dimensions.

The collimator 112b may include a device that restricts beam(s) of particles or waves passing into the first sensor 112, such as light in visible and/or non-visible wavelengths, to specific directions of motion, angles, or ranges of angles to become more aligned in a specific direction as the beam(s) travels through the first sensor 112. The collimator 112b may restrict a spatial cross-section of the beam(s). The collimator 112b may restrict the beam(s) along one dimension and/or along two dimensions.

The collimator 112b may be formed in one or more of a variety of ways. The collimator 112b may be formed of one or more microtubes. The collimator 112b may include a plurality of microtubes, where a microtube of the plurality of microtubes is defined by one or more walls encircling a through-channel. A microtube of the plurality of microtubes may have a width ranging from 10 microns to 150 microns, and/or a height ranging from 30 microns to 500 microns. For example, the microtube may have a height equal to less than a thickness of 4 pages of printer paper, and a width equal to less than a thickness of 1 page of printer paper. The microtubes may be prepared separately and joined together, such as by a binder, or the microtubes may be prepared together. For example, the walls of the microtubes may be formed of CNTs. A catalyst layer may be patterned on a substrate forming an impression of the plurality of microtubes, and the CNTs may be grown on the catalyst layer, forming the walls encircling the through-channels to form the microtubes. The collimator 112b may include a volume of material through which pores and/or apertures are formed. The volume of material may, for example, include a photoresist material. The pores and/or apertures may be etched through the photoresist material, such as by photolithography or plasma etching.

The collimator 112b may be positioned against the filter 112a and/or the optical sensor. For example, the collimator 112b may be disposed between the filter 112a and the optical sensor 112c, or the filter 112a may be disposed between the collimator 112b and the optical sensor 112c. A wall forming a microtube of the collimator 112b may be aligned normal to a surface of the filter 112a and/or a surface of the optical sensor 112c. Light may pass through the filter 112a and the collimator 112b may allow light within a range of normal incidence passing from the filter 112a to impinge on the optical sensor 112c. The collimator 112b may allow light to impinge on the filter 112a within a range of normal incidence. The collimator wall may be aligned at a non-normal angle relative to the surface of the filter 112a and/or the surface of the optical sensor 112c. The angle may correspond to an angle of separated light leaving the filter 112a.

The optical sensor 112c may be operable to convert light rays into electronic signals. For example, the optical sensor 112c may measure a physical quantity of light such as intensity and translate the measurement into a form that is readable by the processor such as an amount of current corresponding directly to the intensity of the light. The optical sensor 112c may include a semiconductor. The semiconductor may have one or more bandgaps corresponding to a wavelength and/or wavelength range. The semiconductor may be arranged into an array, such as an array of pixels, corresponding to specific regions of the filter 112a. In another example, the optical sensor 112c may include a temperature sensor, a velocity liquid level sensor, a pressure sensor, a displacement (position) sensor, a vibration sensor, a chemical sensor, a force sensor, a force radiation sensor, a pH-value sensor, a strain sensor, an acoustic field sensor, an electric field sensor, a photoconductive sensor, a photodiode sensor, a through-beam sensor, a retro-reflective sensor, a diffuse reflection sensor, and so forth.

The optical sensor 112c may include a segment such as a pixel. The optical sensor 112c may include a plurality of the segment arrange in an array, such as an array of pixels. The sensor segment may be aligned with a region of the filter 112a. The segment may have an identifier such that the processor may associate the segment with the region of the filter. The identifier may enable the processor to determine a wavelength of light detected by the segment of the optical sensor 112c. For example, the optical sensor may include a first sensor segment aligned with a first filter region, a second sensor segment aligned with a second filter region, and so forth. The first sensor segment may be identified by the processor as detecting a wavelength and/or range of wavelengths that may correspond to a passband of the first filter region. For example, wavelengths ranging from 400 nm to 449 nm may pass unfiltered through the first filter region. The unfiltered light may strike the first sensor segment, and the first sensor segment may, in response generate an electrical signal that may be transmitted to the processor. The processor may identify the electrical signal as being transmitted by the first sensor segment and may identify that signals transmitted by the first sensor segment may be generated by light having a wavelength ranging from 400 nm to 449 nm.

The filter 112a, the collimator 112b, and the optical sensor 112c may be stacked together to form the first sensor 112. The filter 112a, the collimator 112b, and the optical sensor 112c may be integrated together to form an integrated sensor body. The filter 112a, the collimator 112b, and the optical sensor 112c may be interconnected together. The filter 112a, the collimator 112b, and the optical sensor 112c may be stacked vertically on top of each other. The filter 112a may be wedge-shaped where one end of the filter 112a has a relatively thick end that tapers to a thinner edge. The collimator 112b and the optical sensor 112c may have relatively flat top surfaces and/or bottom surfaces. When the filter is a wedge shape, a filling material 112d may be attached or affixed to the collimator 112b and/or the optical sensor 112c so that the filter 112a may rest or attach flush or level to the collimator 112b and/or the optical sensor 112c. The filling material 112d may include an optically transparent material (such as clear glass or a clear plastic), an optically translucent material (such as polyurethane, colored or frosted glass, colored or frosted plastic, and so forth), or other material that does not interfere with defined wavelengths of light. The filling materials 112d may be attached or affixed to the collimator 112b and/or the optical sensor 112c by an adhesive, by welding, by friction, by a pressure fit, and so forth.

FIG. 1C illustrates a perspective view of the second sensor 114, according to an embodiment. Some of the features in FIG. 1C may be the same as or similar to some of the features in the other FIGS. described herein as noted by same and/or similar reference characters, unless expressly described otherwise. Additionally, reference may be made to features shown in any of the other FIGS. described herein and not shown in FIG. 1C.

The second sensor 114 may include a miniaturized impedance sensor. The miniaturized impedance sensor may include a substrate 114a which may provide structural support for one or more microstructures. The microstructures may include various intermediate layers 114b, a microelectrode 114c, and/or an interstitial filler 114d. The miniaturized impedance sensor may include the substrate 114a, one or more of the intermediate layers 114b, the microelectrode 114c, and/or the interstitial filler 114d. The miniaturized impedance sensor may include a plurality of microelectrodes 114c.

The substrate 114a may provide a base support structure for deposition, growth, and/or etching of the microstructures. The substrate 114a may provide a support structure for integrating the second sensor 114 into the wearable device 100. The substrate 114a may include a silicon and/or a tungsten wafer. The substrate 114a may include glass, such as a glass fiber-reinforced resin. The substrate 114a may be formed of a flexible material such as polyimide. The substrate 114a may include one or more conductors, such as an electrical trace or a through-surface via. The conductors may electrically couple the microelectrodes 114c to electronics external to the second sensor 114, such as the processing device 102.

The intermediate layers 114b may include a conductive layer, one or more insulating layers, and/or a catalyst layer. The conductive layer may electrically couple the microelectrode 114c to the substrate 114a conductor. The catalyst layer may catalyze growth of the microelectrode 114c. In an embodiment, the intermediate layers 114b may include one or more ceramic insulating layers, such as alumina, which may be rendered conductive by a preparation process of the miniaturized impedance sensor.

The microelectrode 114c may include a bundle of nanotubes. The bundle may be infiltrated with a bolstering material, where bolster may refer to a property of a material that increases resistance against an applied force of the material and/or another material with which the material is incorporated. Accordingly, the bolstering material may increase the rigidity of the bundle relative to similarly structured bundles not including the bolstering material. The bolstering material may reduce the brittleness of the bundle relative to similarly structured bundles not including the bolstering material. For example, the nanotubes may include carbon nanotubes (CNTs) grown on an iron catalyst. The bolstering material may include carbon, a metal, and/or a conductive polymer. The microelectrode 114c may include CNTs infiltrated with carbon. The microelectrode 114c may include CNTs infiltrated with a conductive polymer. The microelectrode 114c may include a polymer coated with a conductive film. The conductive film may include a thin film. The thin film may include metal and/or carbon. The polymer may be formed into a pillar.

The interstitial filler 114d may be positioned between rows and/or columns of microstructures on the substrate 114a. The interstitial filler 114d may fill a region between separate microelectrodes 114c. The interstitial filler 114d may include a polymer. The interstitial filler 114d may include a photoresist material. The interstitial filler 114d may include polyimide. The interstitial filler 114d may include bisphenol A novolac epoxy. The interstitial filler 114d may be deposited on the substrate 114a and/or around the intermediate layers 114b and microelectrodes 114c by sputtering and or spin-coating.

The first sensor 112 and/or the second sensor 114 may be referred to as the physiological sensor(s). The physiological sensor may be pressure-sensitive such that a pressure of the physiological sensor against the subject directly correlates with noise in an electronic signal generated by the physiological sensor or an accuracy of the physiological measurement generated from the electronic signal. For example, the pressure with which the first sensor 112 is pressed against the subject may affect an amount of light received by the first sensor 112 and where the light is received. If the first sensor 112 is not pressed against the subject with sufficient pressure, light from outside the subject's body may strike the first sensor 112, adding significant noise to the signal generated by the first sensor 112. If the light source is not pressed against the subject with enough pressure, light may scatter outside the subject's body. If the scattered light is received by the first sensor 112, the signal generated by the first sensor 112 may include a significant amount of noise. Similarly, if the second sensor 114 is not pressed against the subject's body with sufficient pressure, an impedance measured by the second sensor 114 may be significantly higher than the impedance due to a physiological characteristic of the subject, thus introducing noise into the signal generated by the second sensor 114. Ensuring the physiological sensor is pressed against the subject with the correct pressure may, therefore, minimize the amount of noise in the signal generated by the physiological sensor.

The first sensor 112, the second sensor 114, a light source, and/or other measurement electronics may be incorporated together into a sensor module. The sensor module may be referred to unitarily as a physiological sensor throughout this disclosure. The first sensor 112 may take a first measurement of a physiological state of the subject via a first physical mechanism, such as by optical spectroscopy. The second sensor 114 may take a second measurement of the physiological state via a second physical mechanism that may be different from the first physical mechanism, such as by impedance spectroscopy. The processing device 102 may be configured to (e.g. may include programming instructions that, when executed, perform a function that) filter noise from the first measurement and the second measurement by comparing the first measurement and the second measurement.

Figure 2A:
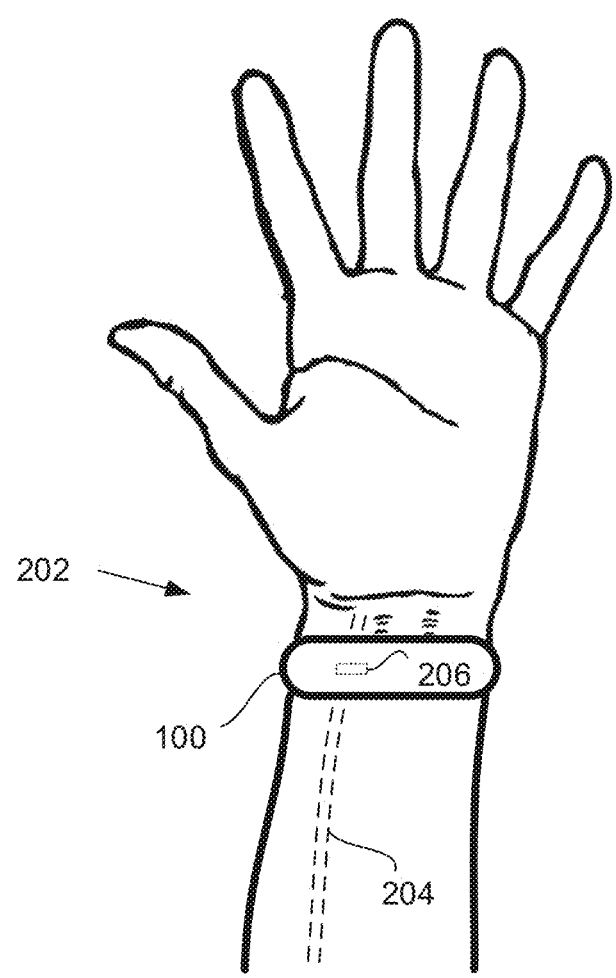
FIG. 2A illustrates the wearable device on a wrist of a subject, according to an embodiment.

FIG. 2A illustrates the wearable device 100 on a wrist 202 of the subject, according to an embodiment. Some of the features in FIG. 2A may be the same as or similar to some of the features in the other FIGS. described herein as noted by same and/or similar reference characters, unless expressly described otherwise. Additionally, reference may be made to features shown in any of the other FIGS. described herein and not shown in FIG. 2A.

The wrist 202 may include a type of physiological structure 204 (e.g. a muscular-walled tube, a vein, an artery, a skeletal structure, a muscular structure, an organ, and so forth). The physiological structure 204 may be, in an embodiment, a vein or an artery. The wearable device 100 may have an integrated physiological sensor 206. The physiological sensor 206 may be, for example, the first sensor 112 and/or the second sensor 114. For example, the physiological sensor 206 may include the miniaturized impedance sensor and/or the miniaturized spectrometer.

The wearable device 100 may be positioned on the wrist 202 so that the physiological sensor 206 may be positioned over the physiological structure 204. In an embodiment, the physiological structure 204 may be positioned in the wrist 202 approximate to an underside of the wrist 202. For example, the physiological structure 204 may be positioned in the wrist 202 between a dermal layer of the wrist 202 and one or more bones in the wrist 202. The physiological sensor 206 may be positioned against the underside of the wrist 202. This may optimize an accuracy and/or a precision of a measurement taken by the physiological sensor 206 from the physiological structure 204. The wearable device 100 may use the measurements to determine a physiological condition of the subject. Positioning the physiological sensor 206 against the underside of the wrist may also reduce a chance of the physiological sensor 206 being struck or otherwise damaged in a way that may affect the accuracy and/or precision of the measurement taken by the physiological sensor 206. For example, an outside of the wrist 202 may be exposed to other surfaces against which the wearable may be struck, whereas an underside of the wrist 202 may be less likely to strike other surfaces because it faces towards a body of the subject.

Figure 2B:
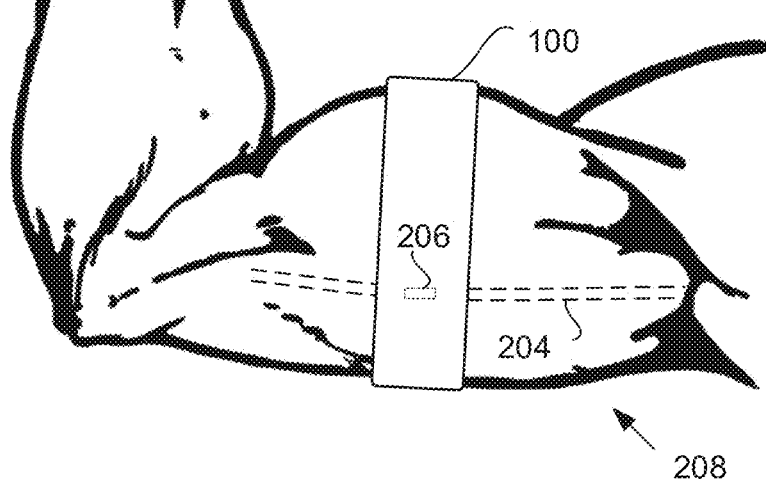
FIG. 2B illustrates the wearable device on an arm of the subject, according to an embodiment.

FIG. 2B illustrates the wearable device 100 on an arm 208 of the subject, according to an embodiment. Some of the features in FIG. 2B may be the same as or similar to some of the features in the other FIGS. described herein as noted by same and/or similar reference characters, unless expressly described otherwise. Additionally, reference may be made to features shown in any of the other FIGS. described herein and not shown in FIG. 2B.

The arm 208, or more generally the body part of the subject, may include a type of the physiological structure 204. The wearable device 100 may be positioned on the arm 208 so that the physiological sensor 206 may be positioned over the physiological structure 204. The wearable device 100 may be worn by the subject on another body part such as a hand of the subject, a forearm of the subject, an elbow of the subject, a chest of the subject, a neck of the subject, a head of the subject, a torso of the subject, a waist of the subject, a thigh of the subject, a calf of the subject, a knee of the subject, an ankle of the subject, a foot of the subject, and so forth. The body part may include the type of the physiological structure such as a muscular-walled tube, an ulnar artery, a radial artery, a brachial artery, a basilic vein, a cephalic vein, an axillary artery, an axillary vein, a carotid artery, a jugular vein, an iliac artery, a femoral artery, a femoral vein, a tibial artery, a great saphenous vein, a *dorsalis* pedis artery, an arch of foot artery, a temporal artery, and so forth. The physiological structure may include an organ, a tissue, a skeletal structure, a muscle, a tendon, a ligament, the subject's skin, and so forth.

The physiological sensor 206 may be pressed against a skin surface of the body part. The physiological sensor 206 and/or wearable device 100 may be positioned on the body part over a region of the body part where the muscular-walled tube may be closest to the skin surface for the body part. The physiological sensor 206 may be positioned against the body part where the muscular-walled tube may be positioned between the physiological sensor 206 and a skeletal structure of the body part. This may minimize a distance between the physiological sensor 206 and the muscular-walled tube, which in turn may optimize one or more biometric measurements taken by the physiological sensor 206 from the muscular-walled tube. The physiological sensor 206 and/or the wearable device 100 may be positioned on the body part over a region of the body part where the skeletal structure is positioned between the skin surface and the muscular-walled tube. This may maximize the distance between the physiological sensor 206 and the muscular-walled tube, which in turn may minimize effects of the muscular-walled tube on measurements taken by the physiological sensor 206. For example, the subject may desire to measure a relatively static physiological condition, physiological parameter, and/or physiological constituent such as a bone density of the subject and/or a body fat percentage of the subject. The physiological structure 204 may be a dynamic structure, such as a muscular-walled tube that changes shape with the subject's heartbeat, and may interfere with measuring the static physiological condition, physiological parameter, and/or physiological constituent. Accordingly, maximizing the distance between the physiological sensor 206 and the physiological structure 204 may result in more accurate and/or precise measurements of the static physiological condition, physiological parameter, and/or physiological constituent. The physiological sensor 206 and/or the wearable device 100 may be positioned on the body part such that the physiological sensor 206 may be approximate the physiological structure 204 and the skeletal structure such that the physiological structure 204 is not between the skeletal structure and the physiological sensor 206 and the skeletal structure is not between the physiological structure 204 and the physiological sensor 206.

Figure 3B:
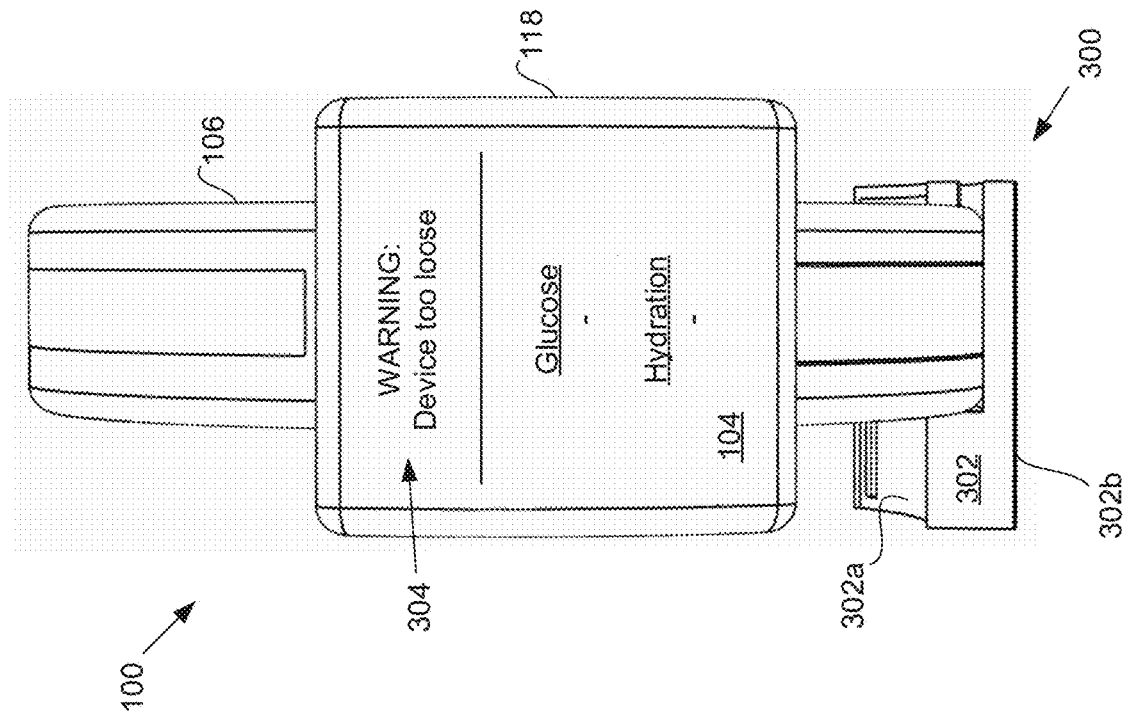
FIG. 3B illustrates a front view of a user interface of the wearable device, according to an embodiment.
Figure 3A:
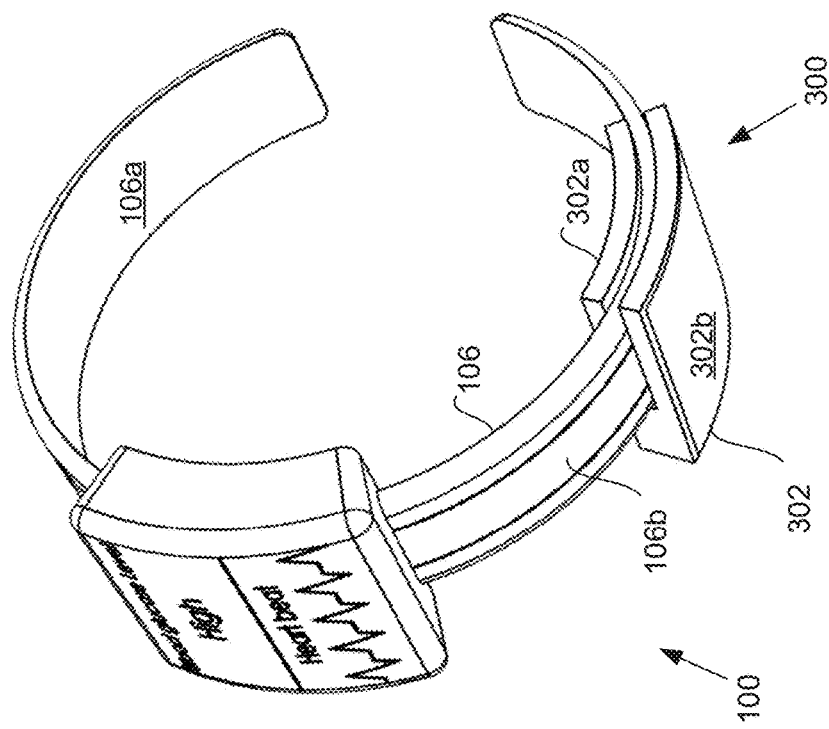
FIG. 3A illustrates a first perspective view of an adjustable measurement device attached to a band of the wearable device, according to an embodiment.

FIG. 3A illustrates a first perspective view of an adjustable measurement device 300 attached to the band 106 of the wearable device 100, according to an embodiment. Some of the features in FIG. 3A may be the same as or similar to some of the features in the other FIGS. described herein as noted by same and/or similar reference characters, unless expressly described otherwise. Additionally, reference may be made to features shown in any of the other FIGS. described herein and not shown in FIG. 3A.

The adjustable measurement device 300 may include a housing 302 configured to attach to the band 106. The housing 302 may house various electronic components. As such, the housing 302 may be formed to protect those components. The housing may be formed of a material, and may have corresponding dimensions, that resist flexing under the types of conditions the wearable device 100 may be subjected to as the subject wears the wearable device 100. For example, the housing may be formed of aluminum, polyvinylchloride, polycarbonate, and so forth. A thickness of the walls of the housing may vary depending on the type of material used to make the housing but may generally range from approximately 1/64 of an inch to approximately 1/8 of an inch. The range may be referred to as "approximate" because various manufacturing limitations may result in, for example, variation of the thickness of the walls from 1/64 of an inch, such as plus or minus 5 thousandths of an inch (mils), and so forth.

The band 106 may be wearable by the subject, such as on a wrist, arm, neck, head, leg, and/or ankle of the subject, and so forth. The housing 302 may be hollow, rigid, and/or shaped to be complementary to a body part of the subject against which the housing 302 is pressed by the band 106 as the subject wears the band 106. For example, various surfaces of the housing 302 may be substantially planar (i.e. planar to within a manufacturing tolerance) or may be curved. The curve of the housing 302 may be complementary to the body part of the subject the housing 302 is designed to be worn against. A radius of a curve of the housing 302 may, therefore, be approximately equal to a radius of the subject's wrist, a radius of the subject's forearm, a radius of the subject's bicep, a radius of the subject's neck, a radius of the subject's head, a radius of the subject's ankle, and so forth. The radius of the curve of the housing 302 may accordingly range, from 1/8 of an inch to 3/4 of an inch when the housing 302 is designed for a finger-worn implementation, from 1/2 of an inch to 4 inches when the housing 302 is designed for a wrist-worn implementation, from 3 inches to 15 inches when the housing 302 is designed for a chest-worn implementation, and so forth.

A shape of the body part to which the housing 302 is complimentary and is designed to be held against may be curvilinear and/or non-uniform. For example, a cross-section of the subject's wrist may not be perfectly circular or a perfect oval. Rather, a curvature of a first portion of the subject's wrist may have a different radius than the curvature of a second portion of the subject's wrist, and so forth. The same may be true of various other body parts of the subject. Accordingly, the housing 302 may have a cross-sectional curvature with a first portion and a second portion. The first portion of the curvature of the housing 302 may have a first radius. The second portion of the curvature of the housing 302 may have a second radius.

The curvature and/or general shape of the housing 302 may be designed for a specific subject or may be generalized. For example, a mold may be made of a specific subject's body part and the mold of the body part may be used to form a mold for the housing 302. In another example, a generalized shape may be determined by overlaying cross-sections of a large sample of subjects (i.e. 100 subjects, 500 subjects, 1000 subjects, and so forth). The cross-sections may be sub-divided into size groupings such as a small-size grouping, a medium-size grouping, a large-size grouping, and so forth. An average shape of the cross-sections, collectively and/or within the size groupings, may be calculated by segmenting the cross-sections and determining average radii for the segments. The average shape of the cross-sections may be used to create a mold for the housing 302.

The band 106 may include an inward-facing surface 106a and an outward-facing surface 106b. The inward-facing surface 106a may face towards the subject's body part as the subject wears the wearable device 100. The outward-facing surface 106b may face away from the body part on which the subject is wearing the wearable device 100. Similarly, an inward-facing portion 302a of the housing 302 may face inwards towards the body part of the subject as the subject wears the wearable device 100 and an outward-facing portion 302b of the housing 302 may face outwards from the body part as the subject wears the wearable device 100. The inward-facing portion 302a of the housing 302 may be shaped to conform to the subject's body part. The outward-facing portion 302b may be shaped complimentarily to the inward-facing portion 302a. The outward-facing portion 302b may have a different shape than the inward-facing portion 302a. For example, the inward-facing portion 302a may be curvilinear and the outward-facing portion 302b may be approximately flat. The inward-facing portion 302a may be rectangular relative to a plane (i.e. may create a rectangular projection on the plane) and the outward-facing portion 302b may be circular relative to the same plane (i.e. may create a circular projection on the plane).

FIG. 3B illustrates a front view of the user interface 104 of the wearable device 100, according to an embodiment. Some of the features in FIG. 3B may be the same as or similar to some of the features in the other FIGS. described herein as noted by same and/or similar reference characters, unless expressly described otherwise. Additionally, reference may be made to features shown in any of the other FIGS. described herein and not shown in FIG. 3B.

The user device 118, which may be coupled to the band 106, may include the user interface 104. The user interface 104 may be electronically coupled to the processing device 102. The processing device 102 may be configured to (i.e. may store and/or execute computer program code that, when executed, generates an output based on stored data and/or an input) compare a current pressure for the band 106 on the subject to an optimal pressure for the band 106 on the subject. The pressure may be measured by a pressure sensor in the band 106, the user device 118, the adjustable measurement device 300, and/or the physiological sensor 206. The user interface 104 may be configured to generate an indicator 304 that indicates a difference between a current pressure and an optimal pressure of the band 106, the user device 118, the adjustable measurement device 300, and/or the physiological sensor 206 against the subject's body part. The optimal pressure may be one pressure or may be one of various pressure values within a range of optimal pressure values.

To minimize noise in a measurement taken by the physiological sensor 206, the physiological sensor 206 may be pressed against the subject's body part at a pressure within a range of optimal pressures. If the pressure is too light, factors external to the subject's body part may influence the measurement. If the pressure is too great, the physiological sensor 206, the band 106, the user device 118, and/or the adjustable measurement device 300 may deform the subject's body part or otherwise affect the subject's body part in a way that produces an inaccurate measurement. For example, pressing the physiological sensor 206 against the subject's skin too hard may squeeze blood out of capillaries under the skin. Pressing the physiological sensor 206 against the subject's skin too hard may burst the capillaries. Having the band 106 too tight around the subject's wrist may restrict blood flow, which may affect measurement of constituents in the subject's blood. Thus, it may be beneficial to ensure the physiological sensor 206, the band 106, the user device 118, and/or the adjustable measurement device 300 are pressed against the subject in a range of pressures that prevent outside influence on the measurement and does not distort the physiological characteristic being measured. The indicator 304 may communicate to the subject or other individual operating the physiological sensor 206 whether the physiological sensor 206, the band 106, the user device 118, and/or the adjustable measurement device 300 is pressed against the subject in the optimal range of pressures.

The indicator 304 may include an audible indication or a visual indication. For example, the user interface 104 may include a speaker, a touch screen display, an output-only display, and so forth. The user interface 104 may be electronically coupled to the processing device 102. The processing device 102 may store and/or execute instructions to generate outputs and/or communicate the outputs via the user interface 104. When the processing device 102 executes a function that outputs the indicator, the user interface 104 may respond by displaying the indicator via the display, emitting a sound, and so forth. Accordingly, the user interface 104 may be configured to generate and/or communicate the indicator.

The indicator 304 may notify the subject whether the pressure measurement value is above a maximum pressure value or below a minimum pressure value. The indicator 304 may notify the subject whether the pressure measurement value is outside the range of optimal pressures. The range of optimal pressures may have an upper limit equal to a maximum optimal pressure and a lower limit equal to a minimum optimal pressure. The indicator 304 may notify the subject of an amount by which the pressure measurement value may be outside the range of pressure values. The indicator may instruct the subject to increase the pressure. For example, the indicator may instruct the subject to increase the pressure on the physiological sensor 206 or decrease the pressure on the physiological sensor 206. As another example, the indicator may instruct the subject to tighten the band 106 or loosen the band 106.

Figure 4:
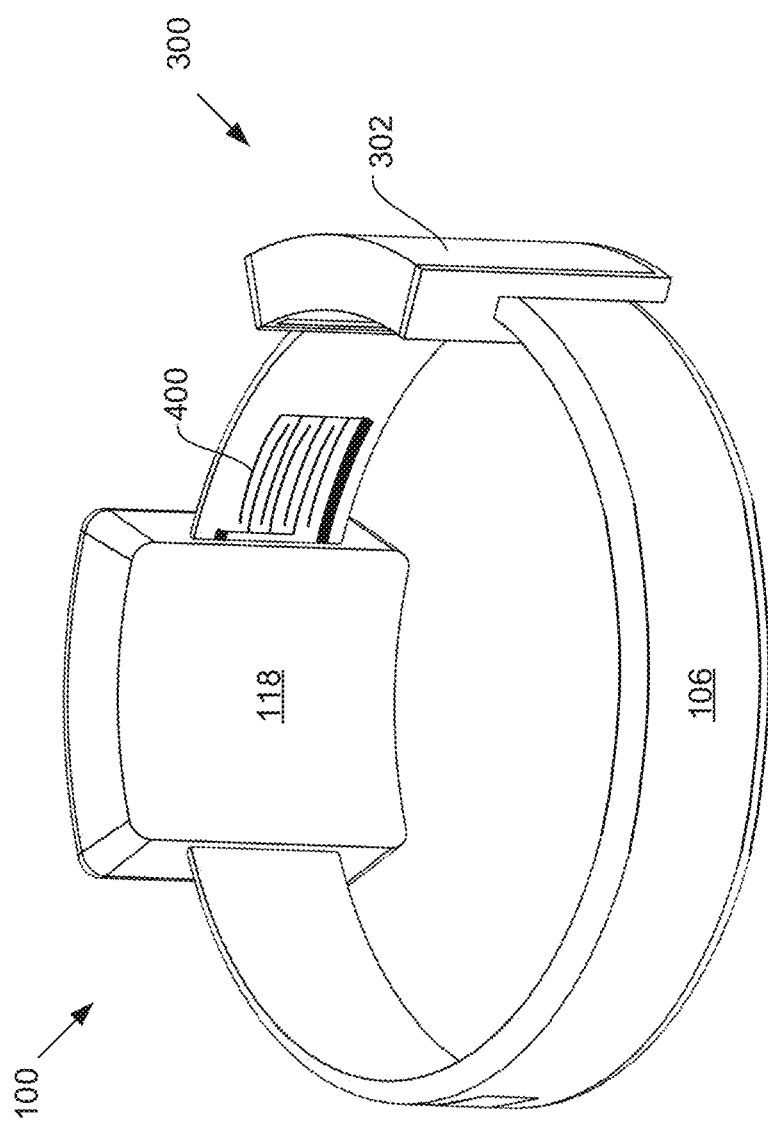
FIG. 4 illustrates a perspective view of the adjustable measurement device attached to a band that has a pressure sensor, according to an embodiment.

FIG. 4 illustrates a perspective view of the adjustable measurement device 300 attached to the band 106 where the band 106 includes a pressure gauge 400, according to an embodiment. Some of the features in FIG. 4 may be the same as or similar to some of the features in the other FIGS. described herein as noted by same and/or similar reference characters, unless expressly described otherwise. Additionally, reference may be made to features shown in any of the other FIGS. described herein and not shown in FIG. 4.

The wearable device may include the pressure sensor 400 coupled to the band 106. The pressure sensor may be configured to measure a pressure of the band 106 on the subject or a pressure of the physiological sensor 206 against the subject as the band 106 may be attached to the subject. The pressure sensor 400 may include a strain gauge, a piezoresistive strain gauge, a capacitive pressure sensor, an electromagnetic pressure sensor, a piezoelectric strain gauge, an optical pressure sensor, a potentiometric pressure sensor, a force balancing pressure sensor, and so forth. A type of the pressure sensor 400 incorporated with the wearable device 100 and/or the adjustable measurement device 300 may depend on how the pressure sensor 400 is incorporated and/or what the pressure sensor 400 is designed to directly measure. For example, the pressure sensor 400 may measure a tightness of the band 106 on the subject. In such an example, a strain gauge may be integrated into the band 106. As another example, the pressure sensor 400 may measure a pressure of the physiological sensor 206 against the subject. In such an example, a capacitive pressure sensor, electromagnetic pressure sensor, and/or potentiometric pressure sensor may be positioned between the physiological sensor 206 and the band 106, the housing 302, and/or the user device 118, and so forth.

The pressure sensor 400 may include a strain gauge. The strain gauge may include conductive tracings embedded in the band 106. The conductive tracings may be formed of copper, silver, gold tungsten, graphite, graphene, and/or carbon nanotubes, and so forth. The conductive tracings may be electronically coupled to the processing device 102. The processing device may be configured to measure a change in resistance of the conductive tracings. The change in resistance may reflect a strain on the band 106. The strain on the band 106 may be a direct indicator of the amount of pressure the band 106 is placing on the subject's body part.

The pressure sensor 400 may be coupled to the band 106 and electronically coupled to the processing device 102. For example, the pressure sensor 400 may couple two ends of the band 106 together. In another example, the pressure sensor 400 may be coupled to the band 106 and the user device 118 between the band 106 and the user device 118. The pressure sensor 400 may generate an electronic signal corresponding to a pressure of the band 106 on the subject as the subject wears the band 106. The processing device 102 may convert the electronic signal into a pressure measurement. The pressure measurement may have a corresponding pressure measurement value. The pressure measurement value may represent a tightness of the band 106 on the subject.

It may be beneficial to measure the tightness of the band 106 on the subject. For example, the physiological sensor 206 may be embedded in the band 106. As stated above, the physiological sensor 206 may provide optimal signal quality when pressed against the subject within a range of pressures. The strain in the band 106 may indicate how tightly the band 106 is pressed against the subject and, therefore, how tightly the physiological sensor 206 is pressed against the subject. In another example, the physiological sensor 206 may be coupled to the band 106, the adjustable measurement device 300, and/or the user device 118 by an elastic coupling mechanism such as a spring. In such an embodiment, the pressure sensor 400 may be positioned between the physiological sensor 206 and the elastic coupling mechanism, between the elastic coupling mechanism and the band 106, and so forth. The pressure sensor 400 may thereby directly measure the pressure of the physiological sensor 206 against the subject.

Figure 5B:
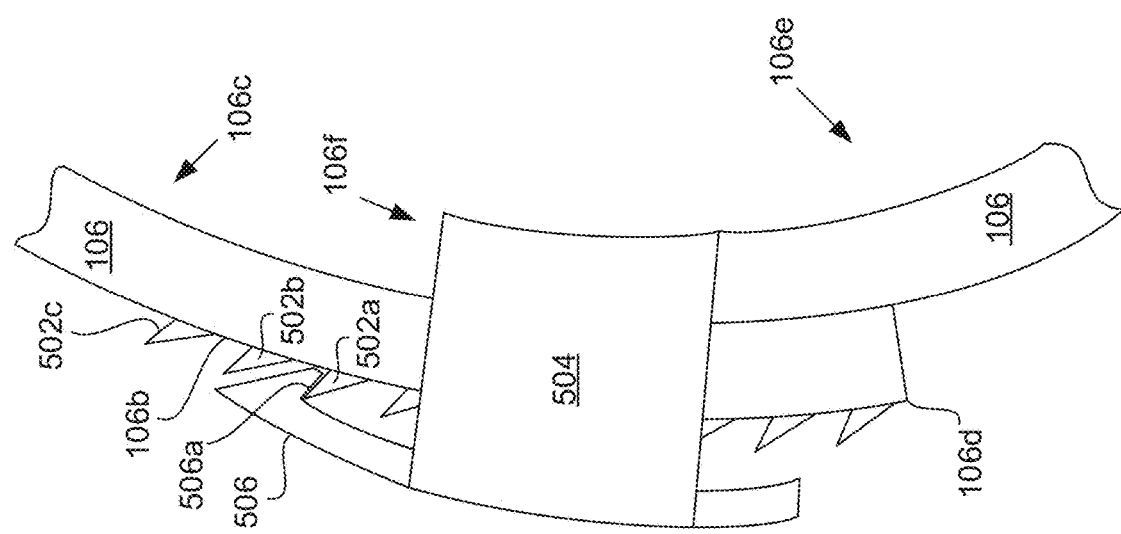
FIG. 5B illustrates a zoomed-in side view of the incrementally tightenable band, according to an embodiment.
Figure 5A:
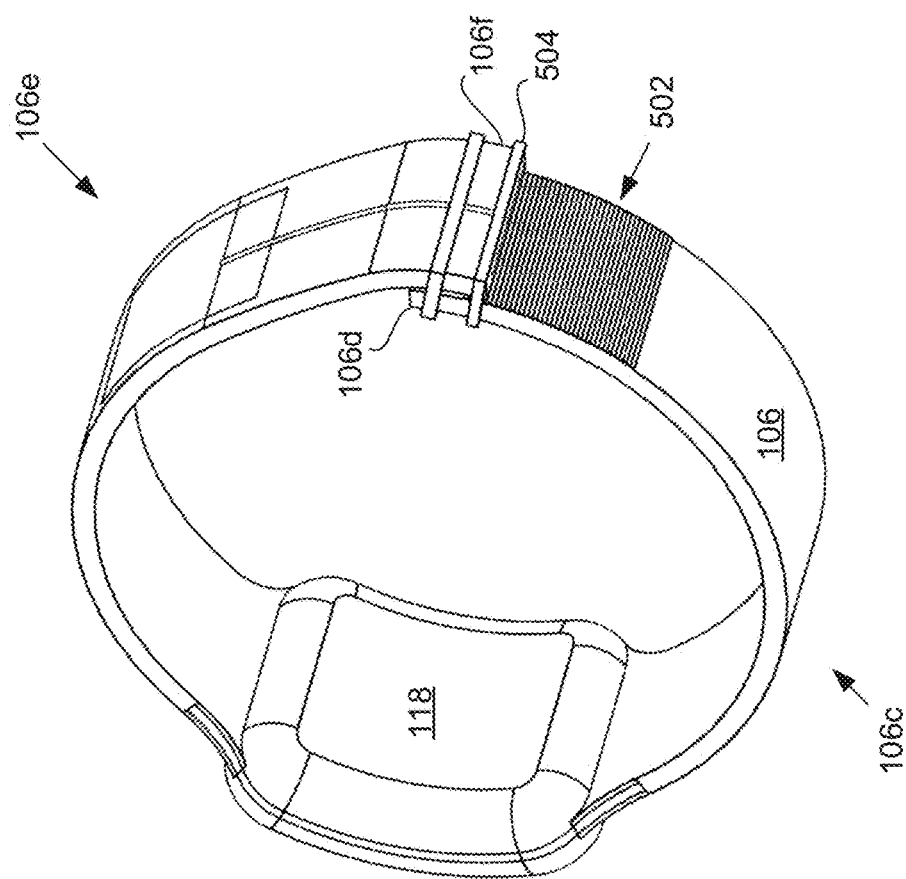
FIG. 5A illustrates a perspective view of the wearable device having an incrementally tightenable band, according to an embodiment.

FIG. 5A illustrates a perspective view of the wearable device 100 where the band 106 is incrementally tightenable, according to an embodiment. Some of the features in FIG. 5A may be the same as or similar to some of the features in the other FIGS. described herein as noted by same and/or similar reference characters, unless expressly described otherwise. Additionally, reference may be made to features shown in any of the other FIGS. described herein and not shown in FIG. 5A.

The band 106 may include a first side 106c extending from the user device 118 and/or the housing 302 of the adjustable measurement device 300 to a first end 106d of the band 106. The first side 106c of the band 106 may include a set of teeth 502 along the first side 106c of the band 106 between the user device 118 (and/or the housing 302, as the case may be) and the first end 106d. The set of teeth 502 may include a first tooth, a second tooth, and so forth. The band 106 may include a second side 106e extending from the user device 118 and/or the housing 302 of the adjustable measurement device 300 to a second end 106f of the band 106. The second side may include a keeper loop 504 affixed the second side 106e of the band 106 approximate to the second end 106f of the band 106.

The first and/or second tooth, and so forth, may engage with a securing mechanism that secures the first end 106d of the band 106 to the second end 106f of the band 106. The securing mechanism may include a pawl, a cantilevered pawl, a gear, one or more teeth of a second set of teeth on the second end 106f of the band 106, and so forth. A distance between the teeth of the set of teeth 502, such as between the first tooth and the second tooth, may be such that tightening the band 106 on the subject, such as around the subject's body part, from engagement of the securing mechanism with the first tooth to engagement of the securing mechanism with the second tooth increases the pressure on the subject by the band in a range from 0.1 kpa to 1 kpa. For example, the securing mechanism may be a cantilevered pawl. Moving the cantilevered pawl from engagement with the first tooth to engagement with the second tooth may increase the pressure on the subject by the band 106 in a range from 0.1 kpa to 0.5 kpa, in a range from 0.2 kpa to 0.5 kpa, in a range from 0.1 kpa to 0.3 kpa, in a range from 0.2 kpa to 0.3 kpa, or by approximately 0.2 kpa.

The spacing of the first tooth, second tooth, and so forth of the set of teeth 502 may be designed such that at least one increment of change in the pressure from engagement of the securing mechanism with the first tooth to engagement of the securing mechanism with the second tooth is less than a range of optimal pressures for the physiological sensor 206. The spacing may be such that a sum of at least two increments of change in the pressure is less than the range of optimal pressures. The spacing may be such that a sum of up to five increments of change in the pressure is less than the range of optimal pressures. The spacing may be such that a sum of up to ten increments of change in the pressure is less than the range of optimal pressures.

The band 106 may be pliable enough that the weight of the band 106 is sufficient to bend the band 106. The band 106 may be rigid enough that the weight of the band 106 is not sufficient to bend the band 106. The band 106 may be formed in an arc as the band 106 is attached to the subject and/or via a manufacturing process of the band that renders the band rigid enough to retain the arc shape against its own weight.

FIG. 5B illustrates a zoomed-in side view of the band 106 of the wearable device 100 where the band 106 is incrementally tightenable, according to an embodiment. Some of the features in FIG. 5B may be the same as or similar to some of the features in the other FIGS. described herein as noted by same and/or similar reference characters, unless expressly described otherwise. Additionally, reference may be made to features shown in any of the other FIGS. described herein and not shown in FIG. 5B.

The set of teeth 502 may be disposed on an outside face (i.e. the outward-facing surface 106b) of the band 106. A cantilevered pawl 506 may be attached to the keeper loop 504. The set of teeth 502 may include a first tooth 502a and/or a second tooth 502b. The first tooth 502a and/or the second tooth 502b may include a catch face 502c that may engage with a catch surface 506a of the cantilevered pawl 506. The catch face 502c may form a non-normal angle with the outside face of the band 106 as the band 106 is formed in the arc such that at least a portion of the cantilevered pawl 506 (e.g. an engagement end 506b and/or the catch face 502c) is disposed under the catch face 502c between the catch face 502c and the first side 106c of the band as the cantilevered pawl engages with the catch face 502c.

The catch face 502c may form a non-normal angle with the outside face of the band 106 to ensure that, even as the band 106 bends, the first tooth 502a and/or the second tooth 502b remains engaged with the cantilevered pawl 506. Such a structure may also enable the cantilevered pawl 506 to remain engaged with the first tooth 502a and/or the second tooth 502b as the subject moves and/or the band 106 changes shape.

The set of teeth 502 may be disposed on an inside face of the band 106, e.g. the inward-facing surface 106a. The catch face 502c of the first tooth 502a and/or the second tooth 502b may form a non-normal angle with the inside face of the band 106 as the band 106 is formed in an arc and attached to the subject. At least a portion of the cantilevered pawl 506 may be positioned under the catch face 502c between the catch face 502c and the inside face of the band 106 as the catch surface 506a engages with the catch face 502c.

Figure 5C:
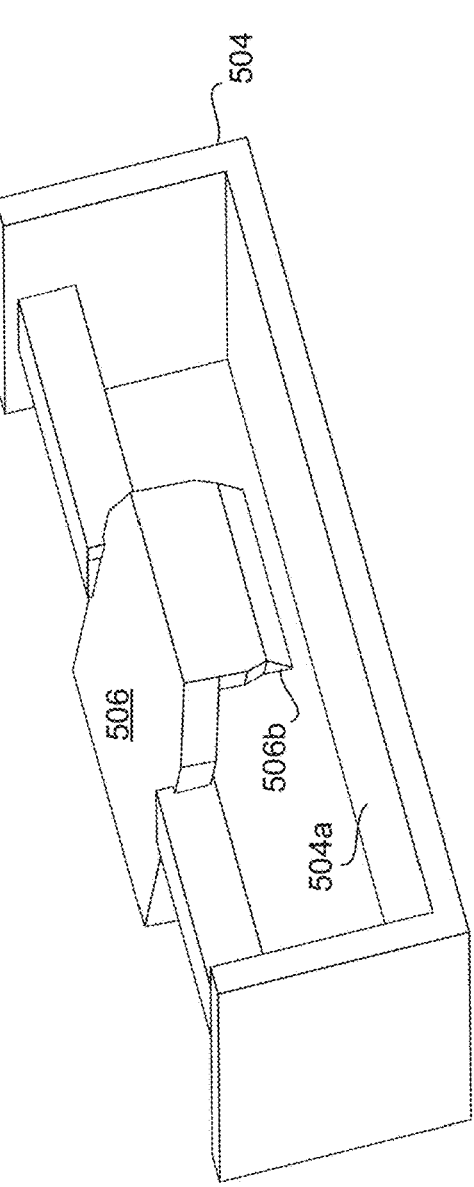
FIG. 5C illustrates a first perspective view of a cantilevered pawl, according to an embodiment.

FIG. 5C illustrates a first perspective view of the cantilevered pawl 506, according to an embodiment. Some of the features in FIG. 5C may be the same as or similar to some of the features in the other FIGS. described herein as noted by same and/or similar reference characters, unless expressly described otherwise. Additionally, reference may be made to features shown in any of the other FIGS. described herein and not shown in FIG. 5C.

The cantilevered pawl 506 may be coupled to the keeper loop 504. The cantilevered pawl 506 may be positioned on the keeper loop 504 such that, as the first side 106c of the band 106 is passed through the keeper loop 504, the cantilevered pawl 506 engages the first tooth 502a or the second tooth 502b. The cantilevered pawl 506 may prevent the first side 106c of the band 106 from pulling out of the keeper loop 504.

The cantilevered pawl 506 may be monolithically integrated with the keeper loop 504. For example, the cantilevered pawl 506 and keeper loop 504 may be 3D printed together or may be manufactured from a single mold of an injection molding system. A distance between an engagement end 506b of the cantilevered pawl 506 and an inside surface 504a of the keeper loop 504 may be less than a thickness of the band 106 along the set of teeth 502. As the first end 106d of the band 106 and the set of teeth 502 are positioned in the keeper loop 504 between the cantilevered pawl 506 and the inside surface 504a, and/or as the cantilevered pawl 506 engages the first tooth 502a or the second tooth 502b, a torsional force between the keeper loop 504 and the cantilevered pawl 506 may force the cantilevered pawl 506 against the first tooth 502a or the second tooth 502b. The cantilevered pawl 506 may thereby be configured to prevent the first end 106d of the band 106 from withdrawing from the keeper loop 504.

Figure 5D:
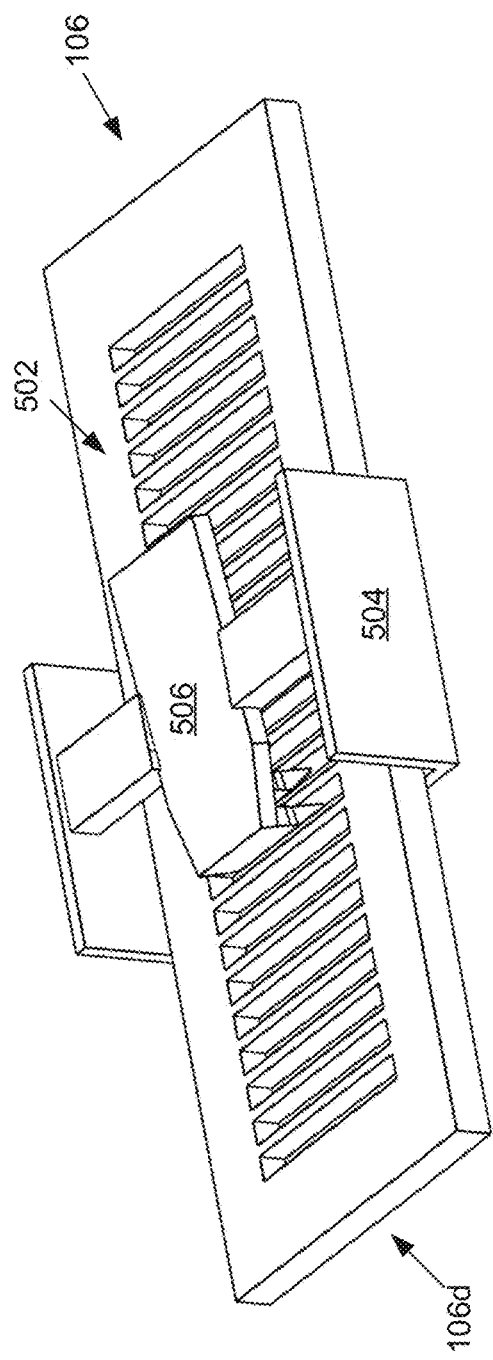
FIG. 5D illustrates a second perspective view of the cantilevered pawl with the band, according to an embodiment.

FIG. 5D illustrates a second perspective view of the cantilevered pawl 506 and includes the band 106, according to an embodiment. Some of the features in FIG. 5D may be the same as or similar to some of the features in the other FIGS. described herein as noted by same and/or similar reference characters, unless expressly described otherwise. Additionally, reference may be made to features shown in any of the other FIGS. described herein and not shown in FIG. 5D.

The engagement end 506b of the cantilevered pawl 506 may include a first instance of the catch surface 506a that engages the first tooth 502a and/or a second instance of the catch surface 506a that engages the second tooth 502b simultaneously as the first instance of the catch surface 506a engages the first tooth 502a. The cantilevered pawl 506 may include three instances of the catch surface 506a, four instances of the catch surface 506a, five instances of the catch surface 506a, and so forth. A shallower depth of the set of teeth 502 may be more effectively engaged by a plurality of teeth, increasing a maximum amount of resistive force the cantilevered pawl 506 and set of teeth 502 can exert counter to one or more forces that may pull the first end 106d of the band 106 from the keeper loop 504.

FIG. 5E illustrates a first perspective view of a second type of the cantilevered pawl 506, according to an embodiment. Some of the features in FIG. 5E may be the same as or similar to some of the features in the other FIGS. described herein as noted by same and/or similar reference characters, unless expressly described otherwise. Additionally, reference may be made to features shown in any of the other FIGS. described herein and not shown in FIG. 5E.

The band 106 may include an outside face, e.g. the outward-facing surface 106b, that faces away from the subject as the band 106 is attached to the subject. An inside face, e.g. the inward-facing surface 106a, face towards and/or is pressed against the subject as the band 106 is attached to the subject. The band 106 may include a side face 106g. The side face 106g may extend between the outside face and the inside face. The side face 106g may be approximately perpendicular to the outside face and the inside face. A plane formed in part by the side face 106g may intersect with a plane formed in part by the outside face and/or a plane formed in part by the inside face. The side face 106g may be planar or may be curved. The outside face and/or the inside face may be curved. The set of teeth 502 may be disposed on the side face 106g of the band 106. The keeper loop 504 may wrap around the width of the band 106 and the cantilevered pawl 506 may be on a side of the keeper loop 504 that is approximately coplanar with, parallel to, and/or otherwise aligned with the side face 106g of the band 106. The first tooth 502a and/or the second tooth 502b may include the catch face 502c. The cantilevered pawl 506 may include the catch surface 506a that engages with the catch face 502c of the first tooth 502a or the second tooth 502b such that, as the band 106 is formed in an arc, and/or as the first end 106d of the band 106 passes through the keeper loop 504, the catch surface 506a of the cantilevered pawl 506 is flush with the catch face 502c of the first tooth 502a and/or the second tooth 502b.

The user interface 104 may be coupled to the keeper loop 504. For example, the user interface 104 may be incorporated into a top surface 504b of the keeper loop 504. The power source 108 may be coupled to and/or incorporated with the keeper loop 504. The keeper loop 504 may include electrical contacts which may electrically couple the user interface 104 to the electrical trace or circuit 116 in the band 106. The electrical trace or circuit 116 may electronically couple the user interface 104 to the processing device 102, the power source 108, the communication device 110, and so forth. The keeper loop 504 may incorporate one or more of the structural elements of the housing. The keeper loop 504 and the housing 302 may be incorporated and/or integrated together. The keeper loop 504 and the housing 302 may be a single unit.

FIG. 5F illustrates a second perspective view of the second type of the cantilevered pawl 506 with a portion of the keeper loop 504 removed to show the cantilevered pawl 506 engaged with the first tooth 502a and the second tooth 502b, according to an embodiment. Some of the features in FIG. 5F may be the same as or similar to some of the features in the other FIGS. described herein as noted by same and/or similar reference characters, unless expressly described otherwise. Additionally, reference may be made to features shown in any of the other FIGS. described herein and not shown in FIG. 5F.

The keeper loop 504 may include two instances of the cantilevered pawl 506. The first instance of the cantilevered pawl 506 may be on one side of the keeper loop 504 and the second instance of the cantilevered pawl 506 may be on a side of the keeper loop 504 opposite the first instance of the cantilevered pawl 506. A spring mechanism 508 may couple the instances of the cantilevered pawl 506 to the keeper loop 504. The engagement end 506b of the cantilevered pawl 506 may pass through an opening in the keeper loop 504. An inner width of the keeper loop 504 may be equal to the width of the band 106 plus a clearance between the band 106 and the keeper loop 504. The clearance may range from 0.1 mm to 2 mm.

Figure 5G:
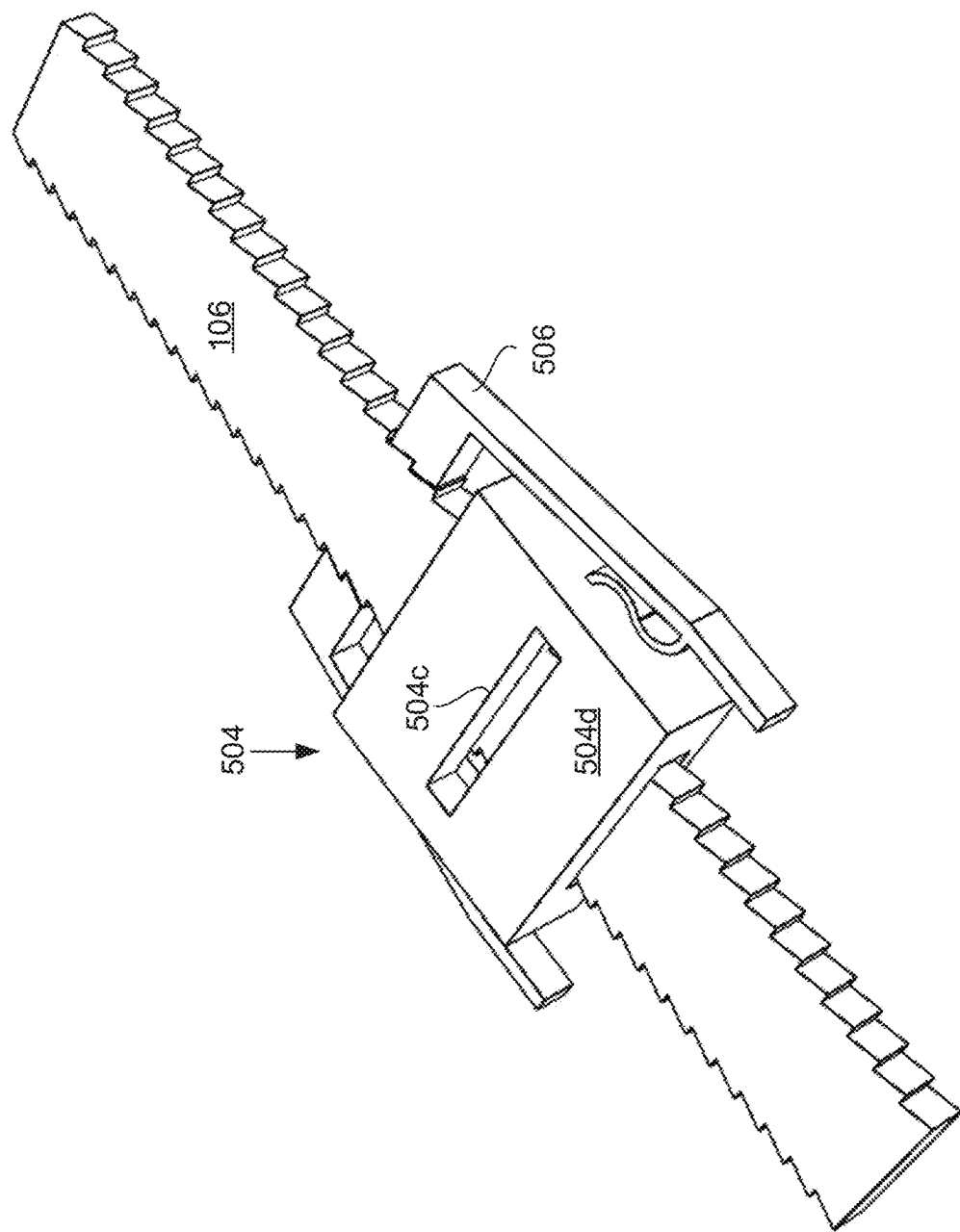
FIG. 5G illustrates a perspective view of a third type of the cantilevered pawl, according to an embodiment.

FIG. 5G illustrates a perspective view of a third type of the cantilevered pawl 506, according to an embodiment. Some of the features in FIG. 5G may be the same as or similar to some of the features in the other FIGS. described herein as noted by same and/or similar reference characters, unless expressly described otherwise. Additionally, reference may be made to features shown in any of the other FIGS. described herein and not shown in FIG. 5G.

The keeper loop 504 may be hollow similar to the housing 302 of the adjustable measurement device 300. Electronics such as the physiological sensor 206, the processing device 102, the power source 108, and/or the communication device 110 may be disposed within the hollow keeper loop 504. The keeper loop 504 may include a window 504c. The physiological sensor 206 may be positioned in the window 504c, aligned with the window 504c, and/or may extend through the window 504c. The window 504c may be positioned on an underside 504d of the keeper loop 504. The underside 504d of the keeper loop 504 may be positioned against the subject's body part as the subject wears the band 106 with the keeper loop 504.

FIG. 5H illustrates a top cross-section view of a motorized band tightening mechanism 510, according to an embodiment. Some of the features in FIG. 5H may be the same as or similar to some of the features in the other FIGS. described herein as noted by same and/or similar reference characters, unless expressly described otherwise. Additionally, reference may be made to features shown in any of the other FIGS. described herein and not shown in FIG. 5H.

The wearable device 100 may include the motorized band tightening mechanism 510. The motorized band tightening mechanism 510 may be integrated into the second end 106f of the band 106. The motorized band tightening mechanism 510 may include a gear 510a coupled to a motor 510b. The motor 510b may drive the gear 510a. The motor 510b may be an electric motor. The motor 510b may be electrically coupled to the processing device 102 and/or the power source 108 via the electrical trace or circuit 116 in the band 106. The processing device 102 may be configured to control the motor 510b. For example, the processing device 102 may include instructions to output a control signal to the motor 510b to tighten the band when the subject inputs an instruction to tighten the band via the user interface 104. The motor 510b may drive the gear 510a. The gear 510a may engage with the set of teeth 502 to tighten and/or loosen the band 106, such as when the subject wears the wearable device 100.

FIG. 5I illustrates a side cross-section view of the motorized band tightening mechanism 510, according to an embodiment. Some of the features in FIG. 5I may be the same as or similar to some of the features in the other FIGS. described herein as noted by same and/or similar reference characters, unless expressly described otherwise. Additionally, reference may be made to features shown in any of the other FIGS. described herein and not shown in FIG. 5I.

Figure 5J:
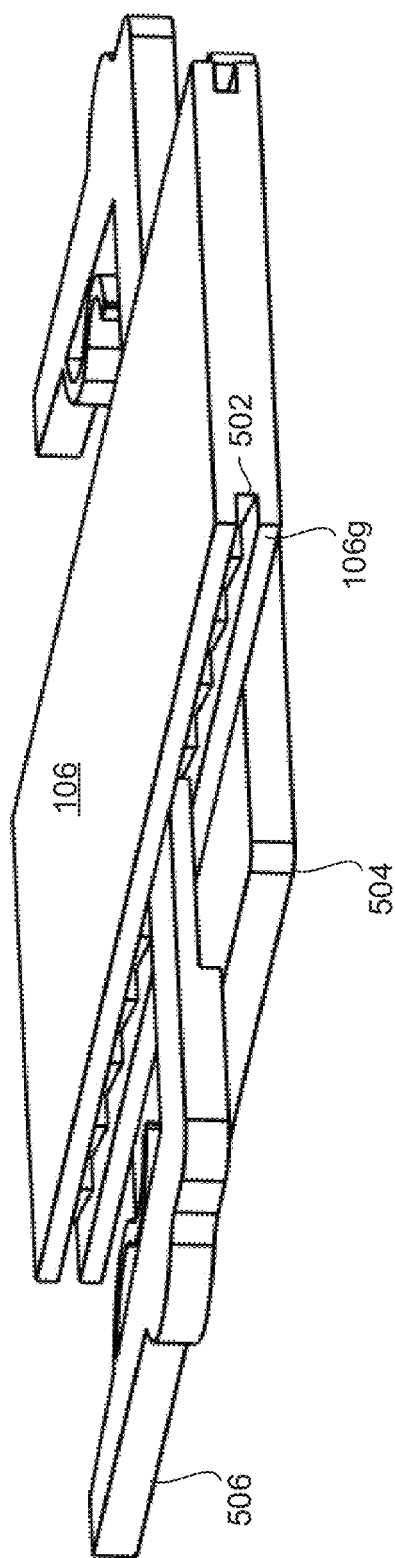
FIG. 5J illustrates a perspective view of the third type of the cantilevered pawl used with a type of the band that includes the set of teeth inset into the side face of the band, according to an embodiment.

FIG. 5J illustrates a perspective view of the third type of the cantilevered pawl 506 used with a type of the band 106 that includes the set of teeth 502 inset into the side face 106g of the band 106, according to an embodiment. Some of the features in FIG. 5J may be the same as or similar to some of the features in the other FIGS. described herein as noted by same and/or similar reference characters, unless expressly described otherwise. Additionally, reference may be made to features shown in any of the other FIGS. described herein and not shown in FIG. 5J.

Figure 5L:
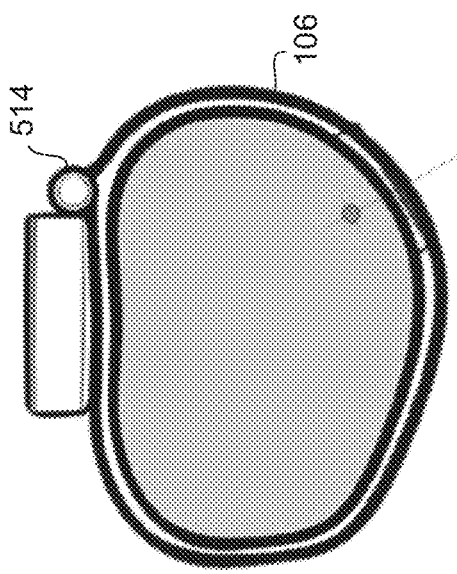
FIG. 5L illustrates a coil mechanism integrated into the band, according to an embodiment.
Figure 5M:
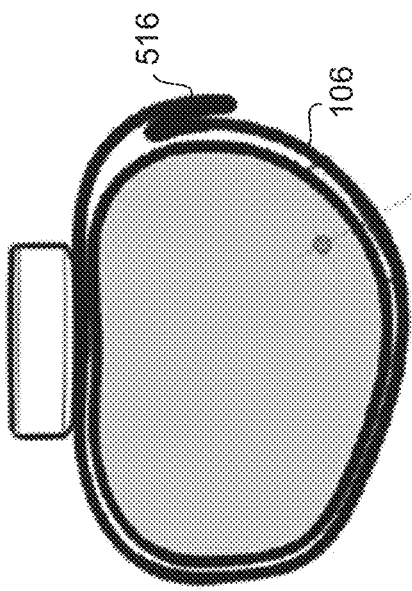
FIG. 5M illustrates a fold in the band, according to an embodiment.
Figure 5K:
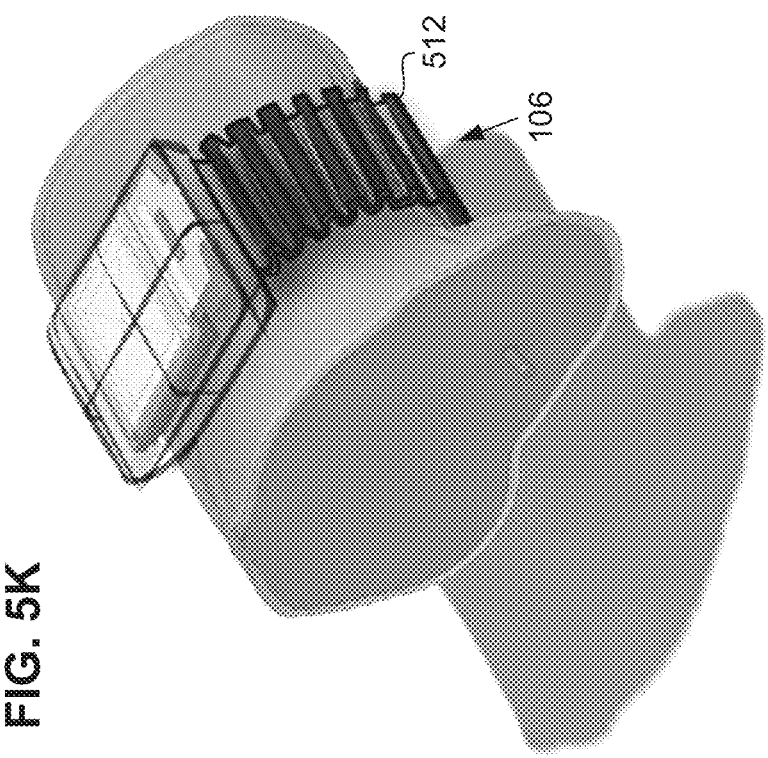
FIG. 5K illustrates an accordion mechanism integrated into the band, according to an embodiment.

FIG. 5K illustrates an accordion mechanism 512 integrated into the band 106, according to an embodiment. Some of the features in FIG. 5K may be the same as or similar to some of the features in the other FIGS. described herein as noted by same and/or similar reference characters, unless expressly described otherwise. Additionally, reference may be made to features shown in any of the other FIGS. described herein and not shown in FIG. 5K.

The band 106 may include the accordion mechanism 512. The entire band 106 may be an accordion or only a portion of the band 106 may be an accordion. The accordion mechanism 512 may extend and/or collapse passively (e.g. as the subject moves and the subject's wrist changes diameter, the accordion mechanism 512 may expand and/or collapse with the changes in the diameter of the subject's wrist). The accordion mechanism 512 may maintain the band 106 and/or the physiological sensor 206 in constant contact with the subject's body part (e.g. the subject's wrist 202). The accordion mechanism 512 may maintain the band 106 and/or the physiological sensor 206 at an approximately constant pressure against the subject's body part. The accordion mechanism 512 may provide a durable means for ensuring constant pressure and/or constant contact when compared with more mechanically complicated mechanisms. The accordion mechanism 512 may enable fine adjustment of the size of the band 106 to enable constant pressure and/or constant contact.

FIG. 5L illustrates a coil mechanism 514 integrated into the band 106, according to an embodiment. Some of the features in FIG. 5L may be the same as or similar to some of the features in the other FIGS. described herein as noted by same and/or similar reference characters, unless expressly described otherwise. Additionally, reference may be made to features shown in any of the other FIGS. described herein and not shown in FIG. 5L.

The band 106 may include the coil mechanism 514. The coil mechanism 514 may enable rolling and/or unrolling of the band 106. The coil mechanism 514 may operate by a spring such as a coil spring. The coil mechanism 514 may enable passive extension and/or retraction of portions of the band 106 to accommodate changes in the diameter of the subject's body part. The coil mechanism 514 may be motorized. The coil mechanism 514 may automatically extend and/or retract portions of the band 106. The coil mechanism 514 may be manually operated to extend and/or retract portion of the band 106. Spring-loaded coiling and/or automatic coiling of the band 106 may enable fine-tuning of the pressure of the band 106 on the subject's body part. Spring-loaded coiling and/or automatic coiling of the band 106 may enable fine-tuning of the pressure of the physiological sensor 206 against the subject's body part. The coil mechanism 514 may maintain the band 106 and/or the physiological sensor 206 in constant contact with the subject's body part (e.g. the subject's wrist 202). The coil mechanism 512 may maintain the band 106 and/or the physiological sensor 206 at an approximately constant pressure against the subject's body part.

FIG. 5M illustrates a fold 516 in the band 106, according to an embodiment. Some of the features in FIG. 5M may be the same as or similar to some of the features in the other FIGS. described herein as noted by same and/or similar reference characters, unless expressly described otherwise. Additionally, reference may be made to features shown in any of the other FIGS. described herein and not shown in FIG. 5M.

The band 106 may include the fold 516. The fold 516 may enable dynamic adjustment of the size and/or shape of the band 106 as the size and/or shape of the subject's body part changes (e.g. as the subject moves and/or engages in activity). The fold 516 may maintain the band 106 and/or the physiological sensor 206 in constant contact with the subject's body part. The fold 516 in the band 106 may be formed with a passive elastic memory. The fold 516 may expand into a more linear form as a strain is exerted on the band. The fold 516 may retract into a more folded form as the strain on the band 106 is lessened. The fold 516 may enable passive extension and/or retraction of the band 106 to accommodate changes in the diameter of the subject's body part. The fold 516 in the band 106 may enable fine-tuning of the pressure of the band 106 on the subject's body part. The fold 516 may enable fine-tuning of the pressure of the physiological sensor 206 against the subject's body part. The fold 516 may maintain the band 106 and/or the physiological sensor 206 at an approximately constant pressure against the subject's body part.

Figure 5O:
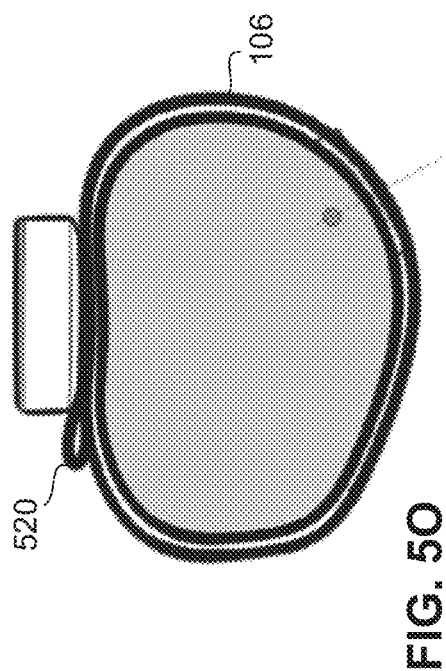
FIG. 5O illustrates a loopback in the band, according to an embodiment.
Figure 5N:
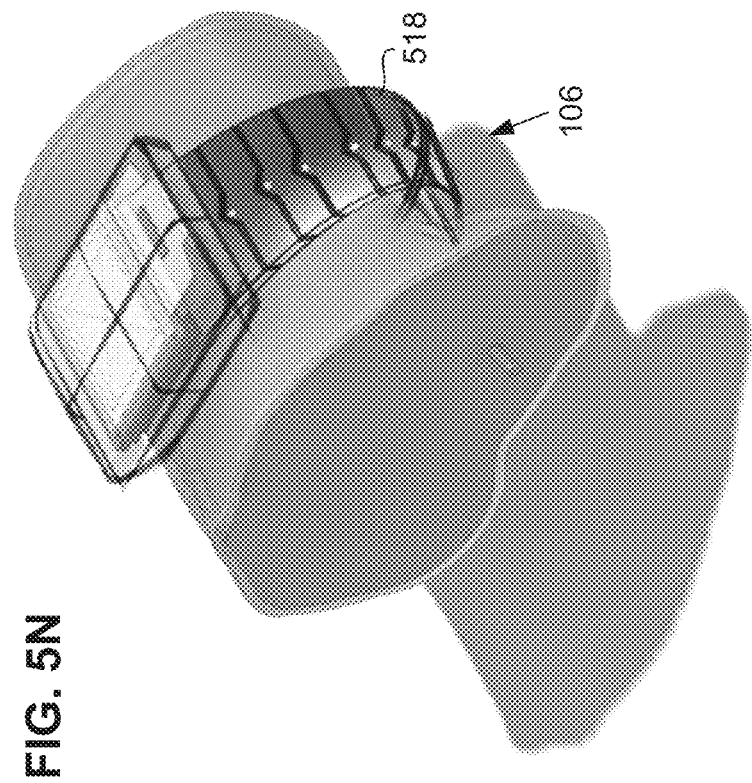
FIG. 5N illustrates the band formed with a set of e-links, according to an embodiment.

FIG. 5N illustrates the band 106 formed with a set of e-links 518, according to an embodiment. Some of the features in FIG. 5N may be the same as or similar to some of the features in the other FIGS. described herein as noted by same and/or similar reference characters, unless expressly described otherwise. Additionally, reference may be made to features shown in any of the other FIGS. described herein and not shown in FIG. 5N.

The band 106 may include one or more of the e-link 518. An individual e-link 518 may be connected to a neighboring e-link 518 inelastically or elastically. The e-link 518 may include conductive tracing (e.g. the electrical trace or circuit 116) and electrical contacts that electrically couple the conductive tracing to electrical contacts and/or conductive tracing in neighboring B-links 518. The physiological sensor 206 may be integrated into one of the e-links. The band 106 may be made entirely of e-links 518. A segment of the band 106 may be made of one or more B-links 518 and another segment of the band 106 may be made of another material and/or structure. The e-links 518 may have a same length. E-links 518 of differing lengths may be provided to enable fine-tuning of a fit of the band 106 on the subject's body part. Elastic coupling of the B-links 518 may enable dynamic adjustment of the size and/or shape of the band 106 as the size and/or shape of the subject's body part changes (e.g. as the subject moves and/or engages in activity). Elastic coupling of the e-links 518 may maintain the band 106 and/or the physiological sensor 206 in constant contact with the subject's body part. Elastic coupling of the e-links 518 may maintain the band 106 and/or the physiological sensor 206 at a constant pressure against the subject's body part. Elastic coupling of the e-links 518 may enable passive extension and/or retraction of the band 106 to accommodate changes in the diameter of the subject's body part. The interchangeability, variable sizing, and elastic coupling of the e-links 518 in the band 106 may enable fine-tuning of the pressure of the band 106 on the subject's body part. The interchangeability, variable sizing, and elastic coupling of the e-links 518 in the band 106 may enable fine-tuning of the pressure of the physiological sensor 206 against the subject's body part. The band 106 with the e-links 518 may maintain the band 106 and/or the physiological sensor 206 in constant contact with the subject's body part (e.g. the subject's wrist 202). The band 106 with the e-links 518 may maintain the band 106 and/or the physiological sensor 206 at an approximately constant pressure against the subject's body part.

FIG. 5O illustrates a loopback 520 in the band 106, according to an embodiment. Some of the features in FIG. 5O may be the same as or similar to some of the features in the other FIGS. described herein as noted by same and/or similar reference characters, unless expressly described otherwise. Additionally, reference may be made to features shown in any of the other FIGS. described herein and not shown in FIG. 5O.

The band 106 may include the loopback 520. The loopback 520 may enable dynamic adjustment of the size and/or shape of the band 106 as the size and/or shape of the subject's body part changes (e.g. as the subject moves and/or engages in activity). The loopback 520 may maintain the band 106 and/or the physiological sensor 206 in constant contact with the subject's body part. The loopback 520 may have a passive elastic memory. The loopback 520 may shrink as a strain is exerted on the band 106. The loopback 520 may expand to an equilibrium size as the strain on the band 106 is lessened. The loopback 520 may enable passive extension and/or retraction of the band 106 to accommodate changes in the diameter of the subject's body part. The loopback 520 may enable fine-tuning of the pressure of the band 106 on the subject's body part. The loopback 520 may enable fine-tuning of the pressure of the physiological sensor 206 against the subject's body part. The loopback 520 may maintain the band 106 and/or the physiological sensor 206 at an approximately constant pressure against the subject's body part.

Figure 5P:
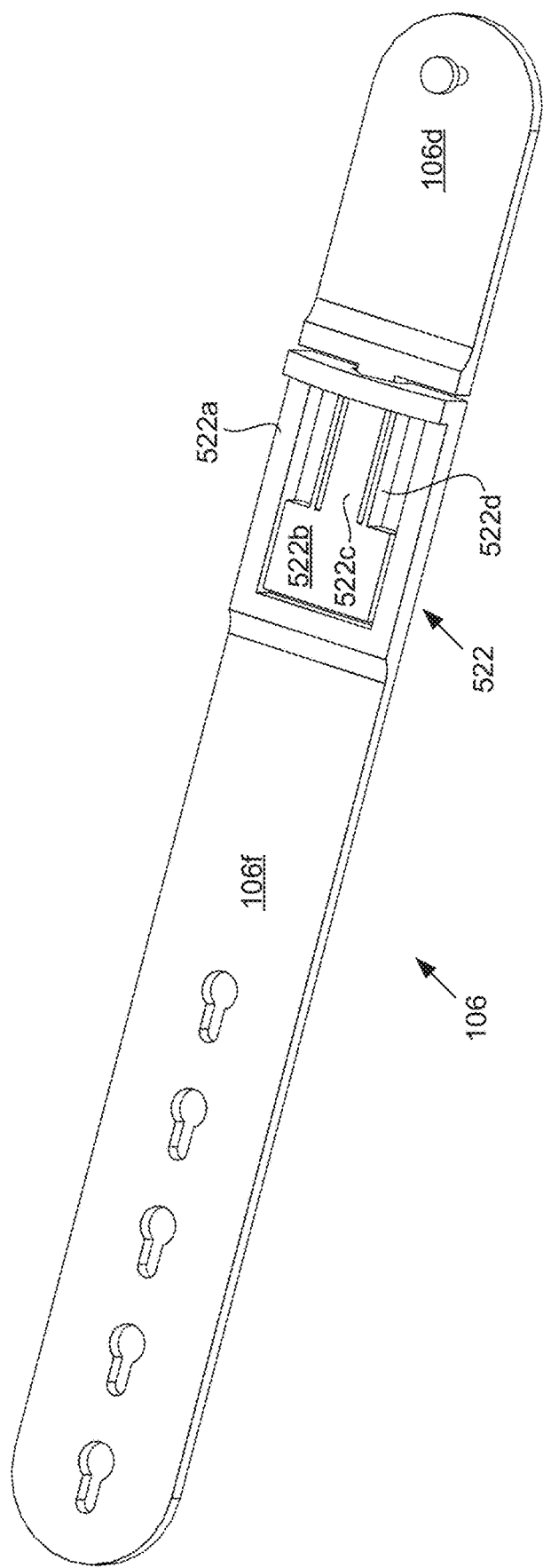
FIG. 5P illustrates a perspective view of the band including a buckling beam mechanism, according to an embodiment.

FIG. 5P illustrates a perspective view of the band 106 including a buckling beam mechanism 522, according to an embodiment. Some of the features in FIG. 5P may be the same as or similar to some of the features in the other FIGS. described herein as noted by same and/or similar reference characters, unless expressly described otherwise. Additionally, reference may be made to features shown in any of the other FIGS. described herein and not shown in FIG. 5P.

The band 106 of the wearable device may include the buckling beam mechanism 522 as a mechanism that maintains the physiological sensor 206 in constant contact with the subject and/or at a constant pressure against the subject. The buckling mechanism 522 may include a buckling mechanism housing 522a. The buckling mechanism housing 522 may be hollow and may house one or more components of the buckling mechanism 522. The buckling mechanism 522 may include a buckling mechanism housing 522a, a stabilizer 522b, a stem 522c, and a buckling column 522d. The buckling mechanism housing 522a may have in internal chamber and/or may house various components of the buckling mechanism 522 within the chamber. As shown, a wall of the buckling mechanism housing 522a is removed to show the internal components. The stabilizer 522b may prevent various of the buckling mechanism 522 components from being pulled out of the buckling mechanism housing 522a and/or may prevent the first end 106d of the band 106 from twisting. The stem 522c may couple the stabilizer 522b to the first end 106d of the band 106. The buckling column 522d may be coupled to a wall of the buckling mechanism housing 522a. The buckling column 522d may be coupled to the stabilizer 522b. The buckling column may be made of a material that springs back into an extended shape when compressed. As a force is exerted on the first end 106d of the band 106 away from the buckling mechanism 522, the buckling column 522d may buckle. The buckling column 522d may exert a counter-force that resists the force exerted on the first end 106d of the band 106 away from the buckling mechanism 522. The counter-force by the buckling column 522d may enable a constant pressure of the band 106 on the subject and/or of the physiological sensor 206 against the subject.

Figure 5Q:
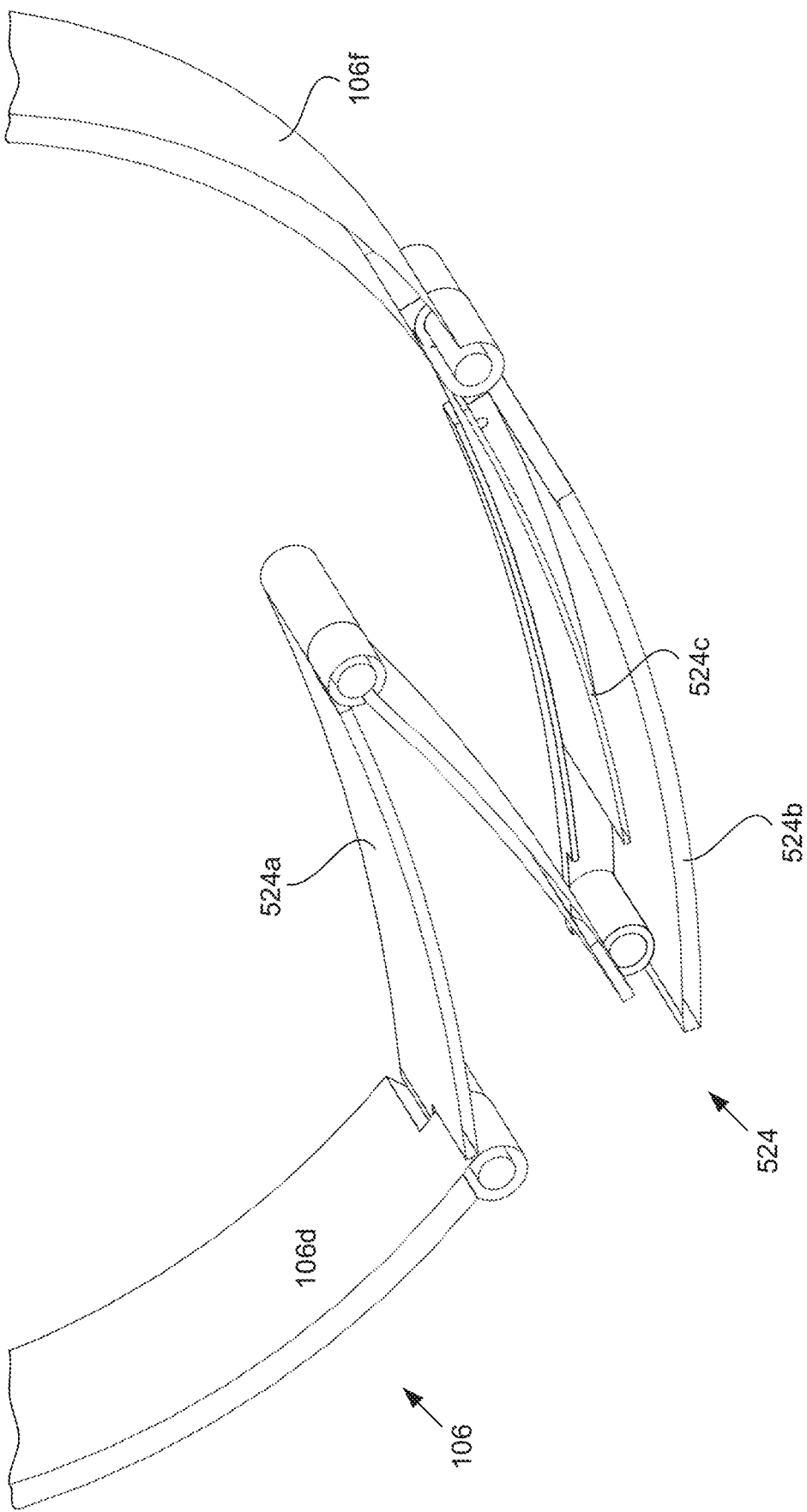
FIG. 5Q illustrates a perspective view of the band including a tri-folding spring mechanism, according to an embodiment.

FIG. 5Q illustrates a perspective view of the band 106 including a tri-folding spring mechanism 524, according to an embodiment. Some of the features in FIG. 5Q may be the same as or similar to some of the features in the other FIGS. described herein as noted by same and/or similar reference characters, unless expressly described otherwise. Additionally, reference may be made to features shown in any of the other FIGS. described herein and not shown in FIG. 5Q.

The band 106 of the wearable device may include the tri-folding spring mechanism 524 as a mechanism that maintains the physiological sensor 206 in constant contact with the subject and/or at a constant pressure against the subject. The tri-folding spring mechanism 524 may include a leaf 524a, a hollow leaf 524b, and a tension mechanism 524c. The leaf 524a and the hollow leaf 524b may fold over each other and/or may latch to each other to narrow a diameter of the band 106. The tension mechanism 524c may be attached to the first end 106d of the band 106 and to an interior of the hollow leaf 524b. The tension mechanism 524c may include, for example, a z-spring that is attached to an inner wall of the hollow leaf 524b at one end and at another end to the first end 106d of the band 106. As a force is exerted on the first end 106d of the band 106 away from the tri-folding spring mechanism 524, the tension mechanism 524c may exert a counter-force that resists the force exerted on the first end 106d of the band 106 away from the tri-folding spring mechanism 524. The counter-force by the tension mechanism 524c may enable a constant pressure of the band 106 on the subject and/or of the physiological sensor 206 against the subject.

Figure 5R:
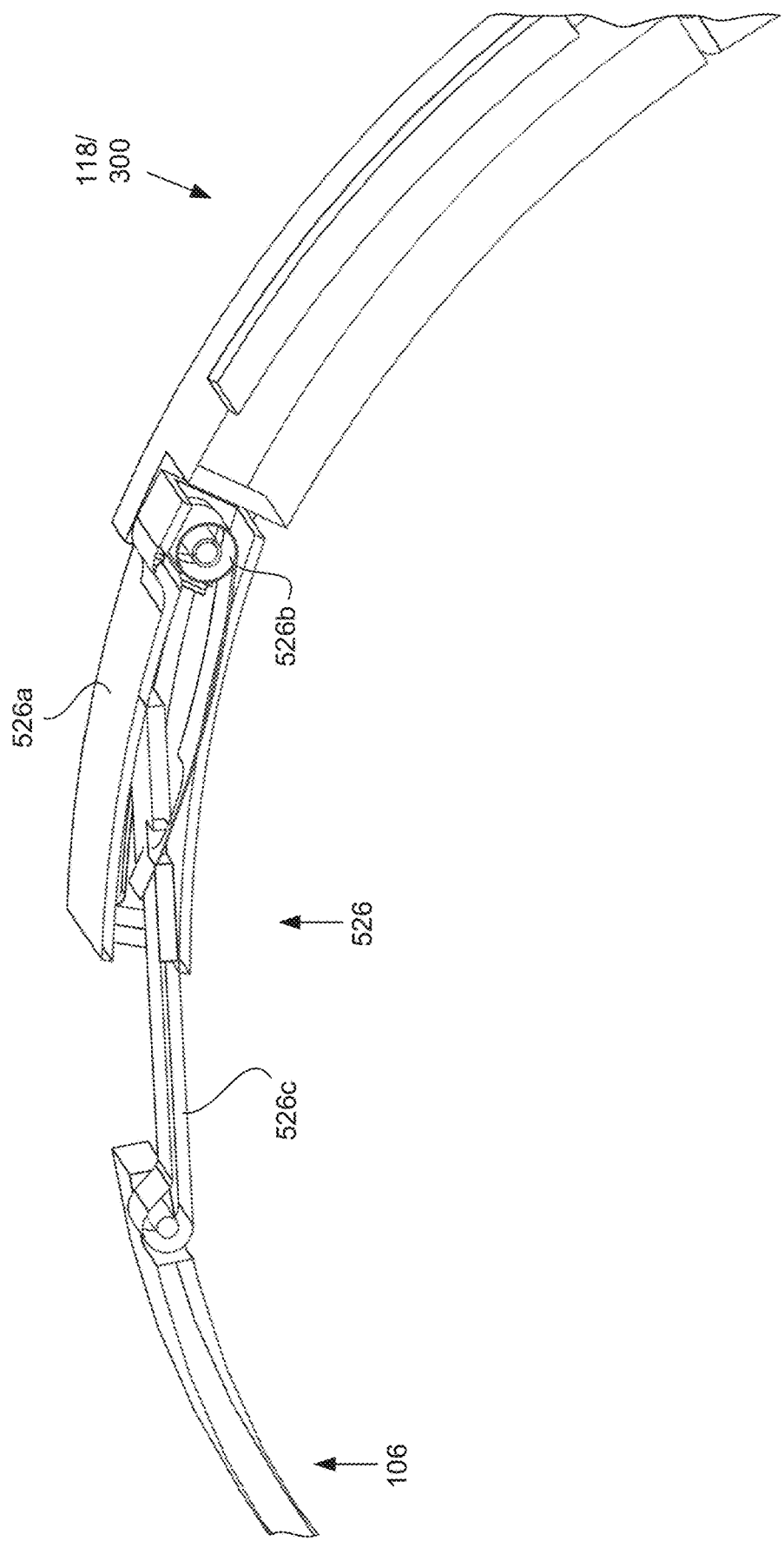
FIG. 5R illustrates a perspective view of the band 106 including a tape spring mechanism 526, according to an embodiment.

FIG. 5R illustrates a perspective view of the band 106 including a tape spring mechanism 526, according to an embodiment. Some of the features in FIG. 5R may be the same as or similar to some of the features in the other FIGS. described herein as noted by same and/or similar reference characters, unless expressly described otherwise. Additionally, reference may be made to features shown in any of the other FIGS. described herein and not shown in FIG. 5R.

The band 106 of the wearable device may include the tape spring mechanism 526 as a mechanism that maintains the physiological sensor 206 in constant contact with the subject and/or at a constant pressure against the subject. The tape spring mechanism 526 may include a spring housing 526a, a tape spring 526b, and/or a coupling mechanism 526c. The spring housing 526a may house various components of the tape spring mechanism 526. The coupling mechanism 526c may couple the tape spring 526b to the band 106. The coupling mechanism 526c may also enable expansion of the tape spring mechanism 526 while protecting the tape spring 526b by allowing the tape spring 526b to stay within the spring housing 526a when the tape spring 526b is extended. As a force is exerted on the band 106 away from the tape spring mechanism 526, the tape spring 526b may exert a counter-force that resists the force exerted on the band 106 away from the tape spring mechanism 526. The counter-force by the tape spring 526 may enable a constant pressure of the band 106 on the subject and/or of the physiological sensor 206 against the subject.

FIG. 6A illustrates a perspective view of the wearable device 100 having a moveable sensor 602 attached to the housing 302 and positioned in a slot 604 in the band 106, according to an embodiment. Some of the features in FIG. 6A may be the same as or similar to some of the features in the other FIGS. described herein as noted by same and/or similar reference characters, unless expressly described otherwise. Additionally, reference may be made to features shown in any of the other FIGS. described herein and not shown in FIG. 6A.

The band 106 may include the slot 604. The moveable sensor 602, which may include the first sensor 112, the second sensor 114, and/or generally the physiological sensor 206, may be aligned with the slot 604 and/or positioned in the slot 604. As the moveable sensor 602 slides along the slot 604, the band 106 may remain fixed relative to the subject's body part. The moveable sensor 602 may be attached to the housing 302 of the adjustable measurement device 300. The moveable sensor 602 may slide along the slot 604 as the housing 302 is adjusted on the band 106.

The moveable sensor 602 may be attached to the housing 302, and the housing 302 and moveable sensor 602 may together form the adjustable measurement device 300. The housing 302 may form a c-shape and the band 106 may pass through a slot of the c-shape. The moveable sensor 602 may be electronically coupled to the processing device 102. The processing device 102 may be positioned in the housing 302 and the moveable sensor 602 and the processing device 102 may be interconnected via a printed circuit board. The processing device 102 may be positioned in the user device 118 and the moveable sensor 602 and the processing device 102 may be interconnected via electrical traces embedded in the band 106.

FIG. 6B illustrates a perspective view of the wearable device 100 having a moveable sensor 602 in a slot 604 in the band 106, according to an embodiment. Some of the features in FIG. 6B may be the same as or similar to some of the features in the other FIGS. described herein as noted by same and/or similar reference characters, unless expressly described otherwise. Additionally, reference may be made to features shown in any of the other FIGS. described herein and not shown in FIG. 6B.

The band 106 may include the slot 604. The moveable sensor 602, which may include the first sensor 112, the second sensor 114, and/or generally the physiological sensor 206, may be aligned with the slot 604 and/or positioned in the slot 604. As the moveable sensor 602 slides along the slot 604, the band 106 may remain fixed relative to the subject's body part. The moveable sensor 602 may be moveably attached to the band 106. For example, a width of the slot 604 and/or the moveable sensor 602 at the surfaces of the band 106 may be less than a width of the slot 604 and/or the moveable sensor 602 between the surfaces of the band 106. As another example, the moveable sensor 602 may include tabs or the slot 604 may include ridges. The slot 604 may include tracks along inside walls of the slot 604 corresponding to the tabs in the moveable sensor 602. The moveable sensor 602 may include tracks corresponding to the ridges of the slot 604.

The moveable sensor 602 may be attached to the housing 302, and the housing 302 and moveable sensor 602 may together form the adjustable measurement device 300. The housing 302 may form a c-shape and the band 106 may pass through a slot of the c-shape. The moveable sensor 602 may be electronically coupled to the processing device 102. The processing device 102 may be positioned in the housing 302 and the moveable sensor 602 and the processing device 102 may be interconnected via a printed circuit board. The processing device 102 may be positioned in the user device 118 and the moveable sensor 602 and the processing device 102 may be interconnected via electrical traces embedded in the band 106.

Figure 7:
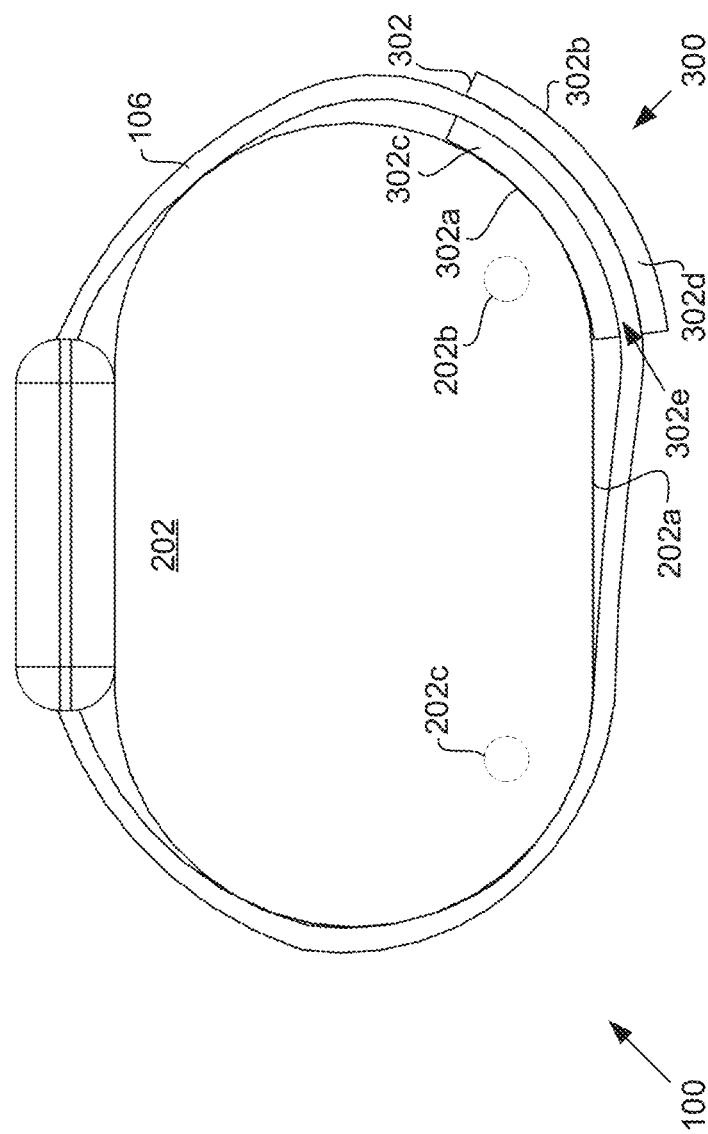
FIG. 7 illustrates the wearable device with the adjustable measurement device relative to a cross-section of the subject's wrist, according to an embodiment.

FIG. 7 illustrates the wearable device 100 with the adjustable measurement device 300 relative to a cross-section of the subject's wrist 202, according to an embodiment. Some of the features in FIG. 7 may be the same as or similar to some of the features in the other FIGS. described herein as noted by same and/or similar reference characters, unless expressly described otherwise. Additionally, reference may be made to features shown in any of the other FIGS. described herein and not shown in FIG. 7.

The housing 302 may include an underside 302c and a topside 302d. The underside 302c of the housing 302 may be positioned between the wrist 202 and the band 106 as the subject wears the band 106 and the adjustable measurement device 300 is attached to the band 106. The topside 302d of the housing 302 may be positioned on an opposite side of the band 106 from the underside 302c of the housing 302 as the adjustable measurement device 300 is attached to the band 106 and as the subject wears the band 106. As discussed regarding other embodiments, the housing 302 may be c-shaped (and/or u-shaped, as the case may be) such that the band 106 passes through a slot 302e of the housing 302 as the housing 302 is attached to the band 106. The underside 302c of the housing 302 may include the inward-facing portion 302a of the housing 302. The topside 302d of the housing 302 may include the outward-facing portion 302b of the housing 302.

At least a portion of a wall of the housing 302 along the inward-facing portion 302a of the housing 302 forms an arc that is complementary to a curvature of a body part of the subject (e.g. the wrist 202, the arm 208, and so forth). The inward-facing portion may be configured to be approximately flush with the body part as the subject wears the band 106 and the housing 302 is coupled to the band 106. The body part may include an underside 202a of the wrist 202 of the subject that includes a radial artery 202b or an ulnar artery 202c of the subject, i.e. the radial artery 202b and/or ulnar artery 202c of the subject may be closest to the surface of the wrist 202 along the underside 202a of the wrist 202.

The housing 302 may be configured to (e.g. designed in shape) conform to the subject's body part to ensure optimal contact between the physiological sensor 206 and the subject's skin. Optimal contact may mean that sensor surfaces and surfaces of the housing surrounding the sensor surfaces are in complete contact with the subject's skin without having to compress the subject's skin and/or otherwise press the physiological sensor 206 into the subject's skin. This may reduce the optimal range for the pressure of the physiological sensor 206 against the subject's skin while still ensuring the signal produced by the physiological sensor 206 has a maximized signal-to-noise ratio (SNR) and/or a maximized amplitude. The conformity of the housing 302 to the subject's body part may improve the comfort of the wearable device 100 and/or the adjustable measurement device 300 to the subject while still enabling the physiological sensor 206 to take sufficient readings from the subject to determine one or more physiological characteristics of the subject.

Figure 8:
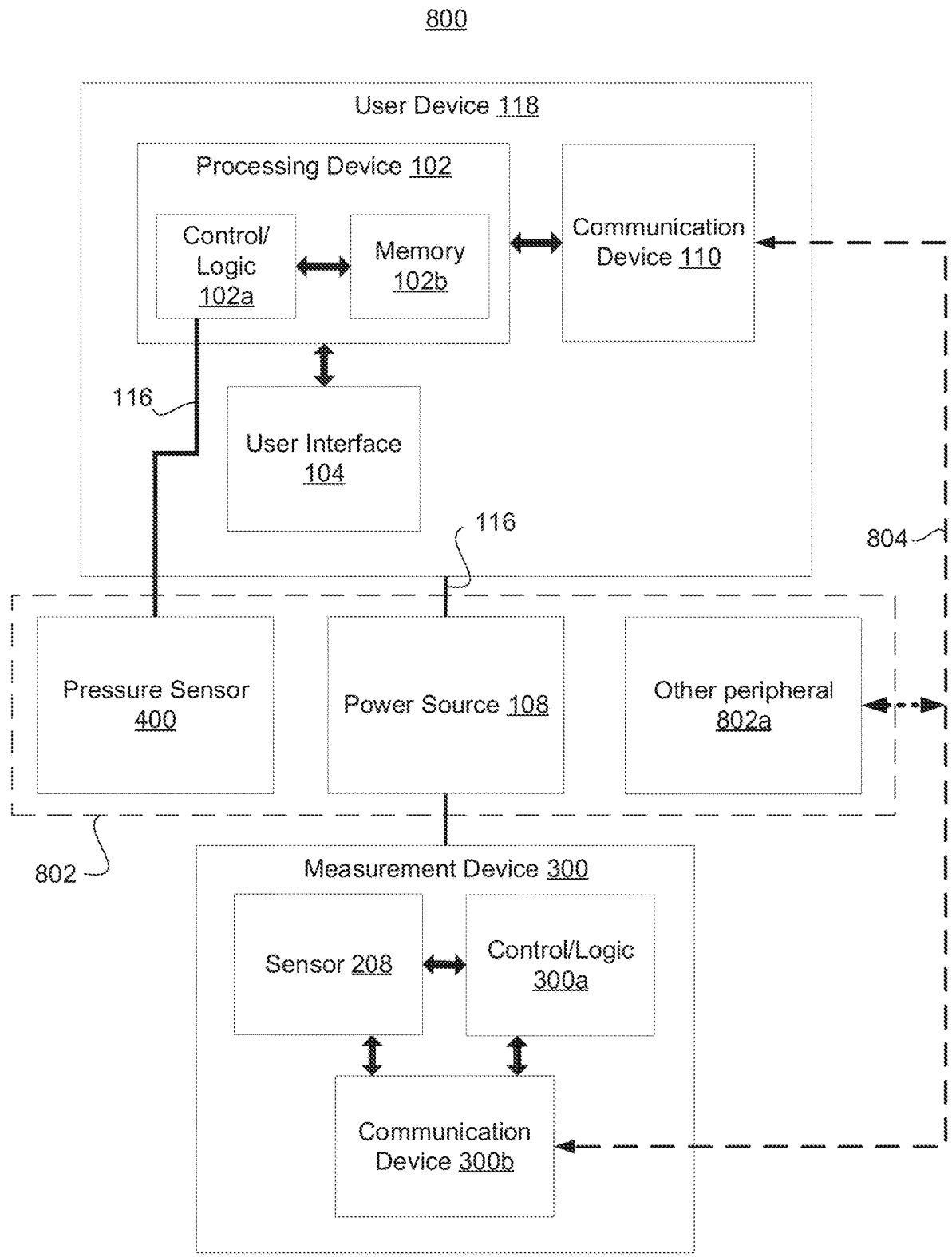
FIG. 8 illustrates a system diagram of a user device and the adjustable measurement device, according to an embodiment.

FIG. 8 illustrates a diagram of a system 800 that includes the user device 118 and the adjustable measurement device 300, according to an embodiment. Some of the features in FIG. 8 may be the same as or similar to some of the features in the other FIGS. described herein as noted by same and/or similar reference characters, unless expressly described otherwise. Additionally, reference may be made to features shown in any of the other FIGS. described herein and not shown in FIG. 8.

The system 800 may include the user device 118, the adjustable measurement device 300, and one or more external devices and/or components 802. The external devices and/or components 802 may include the pressure sensor 400, the power source 108, and/or another peripheral electronic device 802a. The user device 118 may include the processing device 102, the communication device 110, and/or the user interface 104. The processing device 102 may include control programming and/or logic 102a (i.e. control/logic 102a) and memory 102b. The control/logic 102a may execute one or more instructions stored in the memory 102b based on one or more inputs received from the communication device 110, the user interface 104, the pressure sensor 400, the other peripheral electronic device 802a, and so forth. The control/logic 102a may generate one or more outputs based on the input and the instructions. The output may be transmitted to the user interface 104 and/or the communication device 110.

The adjustable measurement device 300 may include the physiological sensor 206, control programming and/or logic 300a (i.e. control/logic 300a), and/or an internal communication device 300b. The control/logic 300a may execute one or more functions based on one or more inputs received by the control/logic 300a from the physiological sensor 206, and/or the communication device 300b. For example, the physiological sensor 206 may generate a signal corresponding to a measurement of a physiological characteristic of the subject. The signal may be communicated from the physiological sensor 206 to the control/logic 300a. The control/logic 300a may filter noise out of the signal and pass the filtered signal to the communication device 300b. The communication device 300b may communicate the filtered signal to the communication device 110 of the user device 118. As another example, the control/logic 300a may receive programming via the communication device 300b of the adjustable measurement device 300. The programming may include a schedule for taking measurements by the first sensor 112. The control/logic 300a may trigger the physiological sensor 206 to take a measurement according to the schedule.

The pressure sensor 400 may be hardwired by conductive tracing, such as the electrical trace or circuit 116, to the control/logic 102a of the processing device 102. For example, the pressure sensor 400 may be a strain gauge in the band 106 and may be connected to the processing device 102 via the electrical trace or circuit 116, which may be embedded in the band 106 and a printed circuit board. The power source 108 may also be hardwired via the conductive tracing to the user device 118 and/or the adjustable measurement device 300. The power source 108 may be embedded in the band 106 separate from the user device 118 and/or the adjustable measurement device 300. The electrical trace or circuit 116 in the band 106 may connect the power source 108 to an electronic interconnect such as a printed circuit board (PCB) in the user device 118 or a PCB in the adjustable measurement device 300. The PCB may include a power control module that regulates delivery of power to the electronic components of the user device 118 and/or the adjustable measurement device 300. For example, the power source 108 may deliver power to the processing device in the user device 118 and the physiological sensor 206 in the adjustable measurement device 300. The PCB may include electrical interconnects that interconnect electronic components, in the user device 118 and/or the adjustable measurement device 300. The electronic components may include the processing device 102, the communication device 110, the user interface 104, the physiological sensor 206, the control/logic 300*a*, the communication device 300*b*, and so forth. The electronic components in the user device 118 and/or the adjustable measurement device 300 may be electronically coupled by wiring in the user device 118 and/or the adjustable measurement device 300.

The communication device 110 of the user device 118 and the communication device 300*b* of the adjustable measurement device 300 may be networked together (e.g. communicatively coupled) via a wired connection, such as the electrical trace or circuit 116, and/or a wireless connection 804. For example, the communication device 110 and the communication device 300*b* may be networked over a Bluetooth® network. The other peripheral electronic device 802*a* may be wirelessly connected to the communication device 110 and/or the communication device 300*b*. The other peripheral electronic device 802*a* may be hardwired to the adjustable measurement device 300 and/or the user device 118.

The user interface 104 may be integrated into the user device 118. The user interface 104 may be integrated into the band 106 separate from the user device 118 and/or the adjustable measurement device 300. The user interface 104 may be integrated into the adjustable measurement device 300. The user interface 104 may be integrated into another user device such as a smartphone, a smartwatch, a tablet, a computer, and so forth, that is separate from band 106, the adjustable measurement device 300, and/or the wearable device 100.

FIG. 9 illustrates a diagram of a system 900 that includes the adjustable measurement device 300 networked to the user device 118, according to an embodiment. Some of the features in FIG. 9 may be the same as or similar to some of the features in the other FIGS. described herein as noted by same and/or similar reference characters, unless expressly described otherwise. Additionally, reference may be made to features shown in any of the other FIGS. described herein and not shown in FIG. 9.

The user device 118 and the adjustable measurement device 300 may not be electrically coupled and may be communicatively coupled, such as via the wireless connection 804. The system 900 may thereby be configured to incorporate the band 106 where the band 106 does not include conductive tracing such as the electrical tracing or circuit 116. For example, the user device 118 may be a smartwatch not having conductive elements integrated into the band 106. The smartwatch and the adjustable measurement device 300 may be paired via a Bluetooth® network. The adjustable measurement device 300 may be attached to the band 106 as the subject wears the smartwatch. The band 106 may be configured to squeeze the subject's wrist 202 with enough pressure to ensure accurate measurement of the physiological characteristic by the adjustable measurement device 300.

The processing device 102 may be configured to take a physiological measurement from the subject using the physiological sensor 206. The processing device 102 may send, via the communication device 110 in the user device 118 and the communication device 300*b* in the adjustable measurement device 300, instructions to take the physiological measurement. The control/logic 300*a* of the adjustable measurement device 300 may automatically trigger the physiological sensor 206 to take the physiological measurement and transmit the signal to the processing device 102. The processing device 102 may cause a value associated with the physiological measurement to be displayed on the user interface 104.

The user device 118 may be attached to the band 106. The user interface 104 may be configured to display the physiological measurement taken from the subject. For example, the user interface may include an LED display, a capacitive touch screen, a resistive touch screen, an augmented reality interface, and so forth. The adjustable measurement device 300 may be configured to take the physiological measurement and communicate the physiological measurement to the user device 118.

The processing device 102 may be communicatively coupled to the physiological sensor 206, such as via the communication devices 110 and 300*a*. The processing device 102 may be configured to receive an electronic signal from the physiological sensor 206. For example, the processing device 102 may be electronically coupled to the communication device 110 and may store instructions to process the electronic signal from the physiological sensor 206. The processing device 102 may be configured to generate a value corresponding to a measurement of a physiological state of the subject. For example, the processing device 102 may be programmed with instructions to compare the electronic signal to a table of signals and corresponding glucose levels. The processing device 102 may be programmed with more complex data analytics to extract one or more measurement values from the electronic signal. The user interface 104 may be electronically coupled to the processing device 102. The user interface 104 may be remote from the processing device 102 and/or may be communicatively coupled to the processing device 102. For example, the user interface 104 may be integrated into another user device and may be communicatively coupled to the processing device 102 via the communication device 110.

The user interface 104 may be communicatively and/or electronically coupled to the physiological sensor 206. The physiological sensor 206 may include processing logic that outputs a measurement value. The measurement value may be output directly to the user interface 104. The user interface 104 may include a dedicated display processor with logic that receives the measurement value as an input and outputs a visual display of the measurement value. The physiological sensor 206 may output the measurement value to the processing device 102. The user interface 104 may be configured to receive the measurement value from the processing device 102. The user interface 104 may generate the indicator 304 in a way that the measurement value may be discernable by the subject or another user. The indicator 304 may be a visual indicator such as words, numbers, symbols, icons, graphics, and/or graphs.

A networking device such as the communication device 300*b* may be electronically coupled to the physiological sensor 206 and coupled to the band 106. The networking device and the physiological sensor 206 may be embedded in the band 106. The processing device 102 and the user interface 104 may be integrated into the user device 118 separate from the band 106. For example, the user device 118 may be a smartphone. The networking device may communicatively couple the physiological sensor 206 to the processing device 102 and/or the user interface 104.

Another communication device may be communicatively coupled to the processing device 102. For example, the additional communication device may be integrated into the band 106 and the processing device 102 may be incorporated into the user device 118 where the user device 118 is remote, e.g. not physically coupled to, the band 106. The adjustable measurement device 300 may be removably attached to the band 106. The communication device 300b in the adjustable measurement device 300 may be a short-range wireless communication device. The additional communication device in the band 106 may have short-range capabilities 9 e.g. may include a Bluetooth® communication chip, a near-field communication chip, and so forth) and long-range communication capabilities (e.g. may include a WiFi communication chip, a cellular communication chip, and so forth). The additional communication device may include a network router. The communication device 300b of the adjustable measurement device 300 may communicate with the processing device 102 via the additional communication device. Thus, the physiological sensor 206 may be communicatively coupled to the communication device 110 and/or the processing device 102. The user interface 104 may be configured to present the information communicated between the physiological sensor 206 and the processing device 102 to the subject, such as by presenting an indicator of the physiological measurement to the subject.

The system 900 may enable the adjustable measurement device to be easily incorporated into the subject's daily routine and/or habits. The adjustable measurement device 300 may be obtained separately by the subject from the user device 118. For example, the user device 118 may include a remote server. The subject may obtain access to the remote server via a subscription service. The subject may enroll the adjustable measurement device 300 with the subscription service. The communication device 300b of the adjustable measurement device 300 may include a cellular communication chip that may communicate with the remote server. The user device 118 may include a smartwatch, a mobile phone, a personal computer, and so forth. The modes of remote communication between the adjustable measurement device 300 and the user device 118 may depend on the type of the user device 118. As such, the communication devices 110 and/or 300a may include short-range communication devices, long-range communication devices, Bluetooth® communication devices, wi-fi communication devices, cellular communication devices, and so forth. The subject may wear the adjustable measurement device 300 using one or more of a variety of types of the band 106. The band 106 may, for example, include an elastic band.

Figure 10:
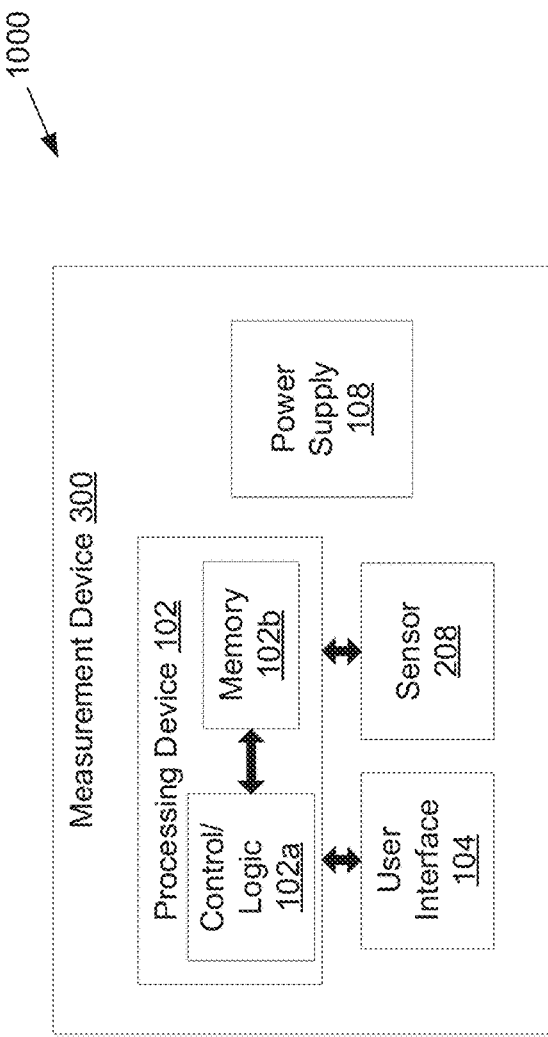
FIG. 10 illustrates a system diagram of the adjustable measurement device with the user interface and an internal power supply, according to an embodiment.

FIG. 10 illustrates a diagram of a system 1000 including the adjustable measurement device 300 with the user interface 104 and the power source 108 positioned internally in the adjustable measurement device 300, according to an embodiment. Some of the features in FIG. 10 may be the same as or similar to some of the features in the other FIGS. described herein as noted by same and/or similar reference characters, unless expressly described otherwise. Additionally, reference may be made to features shown in any of the other FIGS. described herein and not shown in FIG. 10.

The processing device 102, the user interface 104, and/or the power source 108 may be integrated and/or incorporated into the adjustable measurement device 300. The processing device 102 may be electronically coupled to the physiological sensor 206. The adjustable measurement device 300 may not include the communication device 300b. Electronic signals generated by the physiological sensor 206 in response to measurement of a physiological characteristic of the subject may be communicated to the processing device 102. The processing device 102 may generate measurement values based on the electronic signals and may output the measurement values to the user interface 104. The user interface 104 may display and/or otherwise communicate the measurement values to the subject as the subject wears the adjustable measurement device 300.

The adjustable measurement device 300 may include the communication device 300b. The communication device 300b may be electronically coupled to the processing device 102. The communication device 300b may be electronically coupled to the physiological sensor 206. The processing device 102 may transmit, via the communication device 300b, the physiological measurement to another user device configured to display the physiological measurement to the subject. For example, the other user device may include an electronic watch and/or a smartphone. The other user device may include a user application installed on the other user device that interfaces wirelessly with the processing device 102 via the communication device 300b.

Figure 11:
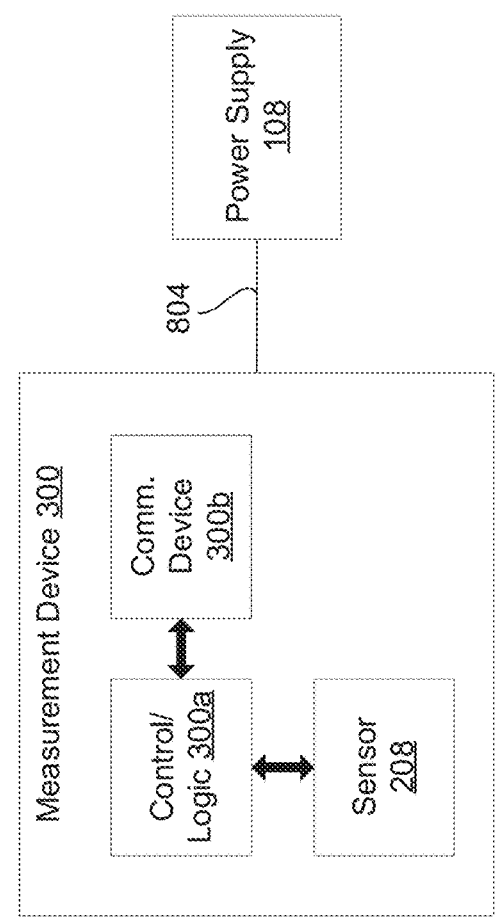
FIG. 11 illustrates a system diagram of the adjustable measurement device with an internal communication device and connected to an external power supply, according to an embodiment.

FIG. 11 illustrates a diagram of a system 1100 that includes the adjustable measurement device 300 with the communication device 300b and connected to the power source 108, which may be external to the adjustable measurement device 300, according to an embodiment. Some of the features in FIG. 11 may be the same as or similar to some of the features in the other FIGS. described herein as noted by same and/or similar reference characters, unless expressly described otherwise. Additionally, reference may be made to features shown in any of the other FIGS. described herein and not shown in FIG. 11.

The adjustable measurement device 300 may include internal sensing, processing, and communication components powered by an external power supply. For example, internal components of the adjustable measurement device 300 may include the control/logic 300a, the communication device 300b, and the physiological sensor 206. The internal components may be electronically coupled via a PCB and/or internal wiring of the adjustable measurement device 300. The internal components may be electrically coupled to the power source 108 by a conductive element such as wiring and/or electrical trace or circuit 116. For example, the power source 108 may be integrated into the band 106 and electrically coupled to the internal components of the adjustable measurement device 300. The adjustable measurement device 300 may include electrical contacts and a portion of the electrical trace or circuit 116 in the band 106 may be exposed. The exposed portion of the electrical trace or circuit 116 may have a length greater than a length of the electrical contacts. The length of the exposed electrical trace or circuit 116 may determine an amount of adjustability of the adjustable measurement device 300 on the band 106.

The adjustable measurement device 300 may have a minimalistic design that limits the components integrated into the adjustable measurement device 300 to only those components necessary to acquire the electronic signal corresponding to measurement of the physiological characteristic of the subject. This may reduce the size of the housing 302. Subjects, including subjects that have chronic health conditions like diabetes, are more likely to wear a monitoring device with a minimalistic design. A monitoring device with a minimalistic design is less likely to interfere with the subject's day-to-day activities and the subject is, therefore, more likely to wear the monitoring device. The adjustable measurement device 300 is such a minimalistic monitoring device. The limited number of internal components of the adjustable measurement device 300 allows for a smaller volume of the housing 302 compared to other monitoring devices. Integration of the power source 108 into the band 106 further minimizes the size of the housing 302.

Figure 12:
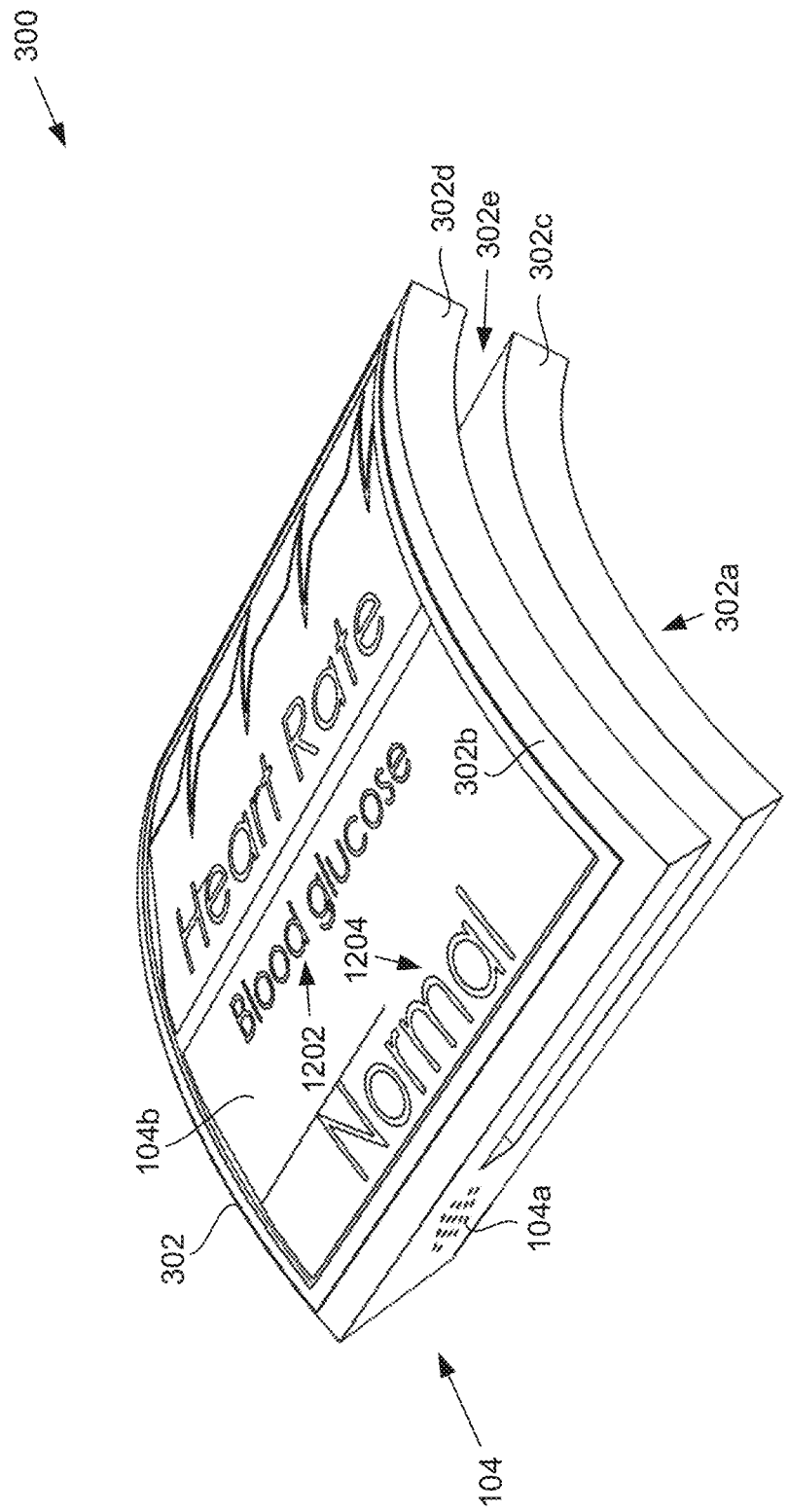
FIG. 12 illustrates a perspective view of the adjustable measurement device including the user interface, according to an embodiment.

FIG. 12 illustrates a perspective view of the adjustable measurement device 300 including the user interface 104, according to an embodiment. Some of the features in FIG. 12 may be the same as or similar to some of the features in the other FIGS. described herein as noted by same and/or similar reference characters, unless expressly described otherwise. Additionally, reference may be made to features shown in any of the other FIGS. described herein and not shown in FIG. 12.

The adjustable measurement device 300 may include the user interface 104. The user interface may be integrated into a first side of the housing 302 (e.g. the topside 302d of the housing 302). The user interface may be electronically coupled to the power source 108, the processing device 102, the communication device(s) 110/300a, and/or the physiological sensor 206. The user interface 104 may display to the subject and/or another person viewing the user interface 104 a physiological measurement 1202 that is taken by the physiological sensor 206 and that is processed by the processing device 102. The user interface 104 may display to the subject and/or another person viewing the user interface 104 a value 1204 associated with the physiological measurement 1202.

The user interface 104 may include a speaker 104a that emits sounds audible to the subject and/or a person within an audible range of the speaker 104a. The sound may provide an indication of one or more measurements taken by the physiological sensor 206 and/or the pressure sensor 400. For example, the speaker 104a may emit a series of beeps that increase in frequency (either regarding the time between beeps or the frequency of each beep) as the physiological sensor 206 as brought into closer alignment with the physiological structure 204 of the subject such as a vein and/or artery. The user interface 104 may include a touch screen 104b that receives touch-based inputs from the subject and visually displays information to the subject and/or a person within viewing range of the touch screen 104b. For example, the touch screen 104b may display an icon to the subject. When the subject touches the icon, the user interface 104 may communicate the touch as an input to the processing device 102.

The processing device 102 may be configured to detect a proximity of the physiological sensor 206 to the physiological structure 204 (e.g. a vein and/or artery) of the subject as the subject wears the housing 302. For example, the processing device 102 may include programming that takes an input such as a signal of heartbeat waveform of the subject and calculates an SNR for the signal. The processing device 102 may compare the SNR to a range of SNRs, where the range of SNRs is associated with a proximity of the physiological sensor 206 to the physiological structure 204. The processing device 102 may compute the proximity based on an algorithm for the proximity as a function of the SNR. The processing device 102 may output the proximity of the physiological sensor 206 to the physiological structure 204. Based on the output, the processing device 102 and/or the user interface 104 may generate indicator 304, which may indicate the proximity of the physiological sensor 206 to the physiological structure 204. The processing device 102 may determine the proximity iteratively, such as every second, ten times per second, one hundred times per second, and so forth. As a position of the adjustable measurement device 300 changes on the subject, the proximity of the physiological sensor 206 to the physiological structure 204 may change. As the proximity changes, the indicator 304 may change.

The user interface 104 and/or the processing device 102 may be configured to dynamically update the indicator as the adjustable measurement device is moved on the band 106 and/or moved relative to the physiological structure 204 of the subject, such as to increase the proximity of the physiological sensor 206 to the subject's vein and/or artery. For example, the user interface 104 may display an arrow pointing a direction of the muscular-walled tube relative to the physiological sensor 206, i.e. a direction the subject should move the adjustable measurement device 300 to bring the physiological sensor 206 into closer alignment with the physiological structure 204. The arrow may decrease in size and/or change color as the physiological sensor 206 gets closer to the physiological structure 204. The arrow may grow in size and/or change color as the physiological sensor 206 gets further away from the physiological structure 204. As another example, the user interface 104 may show a virtual representation of the physiological structure 204 relative to a virtual representation of the physiological sensor 206. The position on the user interface 104 of the physiological structure 204 relative to the physiological sensor 206 may change as the adjustable measurement device moves on the subject. As yet another example, the user interface 104 may emit a sound that changes as the physiological sensor changes proximity to the physiological structure 204.

The housing 302 may be rigid and may be shaped to be complementary to a body part of the subject against which the housing 302 is pressed by the band 106 as the subject wears the band 106. The slot 302e may be complementary in shape to the body part of the subject, such as by being formed in an arc-shape. The underside 302c of the housing 302 may be complementary in shape to the body part of the subject, such as by being formed in an arc-shape. The topside 302d may be complementary in shape to the body part of the subject, such as by being formed in an arc-shape. The arc formed by the housing 302, the underside 302c, the slot 302e, and/or the topside 302d may include an arc length ranging from half an inch to three inches and/or an arc angle ranging from ten degrees to one hundred degrees. The arc length may range from half an inch to one inch, from one inch to one-and-a-half inches, from one-and-a-half inches to two inches, from two inches to two-and-a-half inches, from two-and-a-half inches to three inches, from one inch to two inches, from two inches to three inches, from one inch to three inches, and so forth. The arc angle may range from ten degrees to fifty degrees, from fifty degrees to one hundred degrees, from ten degrees to twenty-five degrees, from twenty-five degrees to fifty degrees, from fifty degrees to seventy-five degrees, from seventy-five degrees to one hundred degrees, and so forth. The topside 302d of the housing 302 may have a different shape than the underside 302c. For example, the topside 302d may be parallel to a plane that is tangential to an arc formed by the underside 302c. The slot 302e may have the same shape as the underside 302c or the same shape as the topside 302d. The slot 302e may have a different shape than both the underside 302c and the topside 302d. For example, the slot 302e may have an arc angle that is greater than the arc angle of the underside 302c and is less than the arc angle of the topside 302d.

The adjustable measurement device 300 may include components such that the user device 118 is effectively integrated with the adjustable measurement device 300. The user device 118 may include components such that the adjustable measurement device 300 is integrated with the user device 118. The user device 118 and the adjustable measurement device 300 may be integrated into the same housing, e.g. housing 302, and may, therefore, be considered a single device. For example, the adjustable measurement device 300 may include the user interface 104, the power source 108, the communication device 110, the processing device 102, the first sensor 112, the second sensor 114, moveable sensor 602, the underside 302c with the inward-facing portion 302a, the topside 302d with the outward-facing portion 302b, the slot 302e, the pressure sensor 400, and so forth.

The user interface 104 may be configured to notify the subject of a pressure and/or a change in the pressure of the physiological sensor 206 against the subject. The user interface 104 may be configured to notify the subject of a strain the band 106. For example, the user interface 104 may be configured to generate a succession of audible beeps that correspond to a difference between the current pressure/strain and an optimal pressure/strain. As another example, the user interface 104 may be configured to display a set of colors along a color spectrum. An individual color in the set of colors may correspond to a difference between the current pressure and the optimal pressure or a range of optimal pressures.

Incorporating the user interface 104 into the adjustable measurement device 300 may allow a subject to incorporate the adjustable measurement device 300 as an accessory in a minimalistic way without adding additional burden to the subject. For example, the subject may already wear a wristwatch and/or wrist jewelry. The adjustable measurement device 300 may be attached to a band and worn by the subject in place of the wristwatch. The adjustable measurement device 300 may include features of the wristwatch, such as displaying the time and date, and may additionally provide physiological measurement information to the subject such as a measurement of the subject's glucose levels. The adjustable measurement device may pair with the subject's smartphone and show phone call data, message data, and so forth.

FIG. 13A illustrates the underside 302c of the housing 302 of the adjustable measurement device 300, according to an embodiment. Some of the features in FIG. 13A may be the same as or similar to some of the features in the other FIGS. described herein as noted by same and/or similar reference characters, unless expressly described otherwise. Additionally, reference may be made to features shown in any of the other FIGS. described herein and not shown in FIG. 13A.

The housing 302 may include a first opening 1302, a second opening 1304, and/or a third opening 1306. The housing 302 may include one or more instances of the first opening 1302, the second opening 1304, and/or the third opening 1306. For example, the housing 302 may include one instance of the first opening 1302, four instances of the second opening 1304, and/or two instances of the third opening 1306. The housing 302 may include one instance of the first opening 1302 and zero instances of the second opening 1304 and the third opening 1306. The housing 302 may include one instance of the second opening 1304 and zero instances of the first opening 1302 and the third opening 1306. The housing 302 may include one instance of the third opening 1306 and zero instances of the first opening 1302 and the second opening 1304. The housing may include one instance of the first opening 1302, one instance of the second opening 1304, and zero instances of the third opening 1306. The housing 302 may include four instances of the second opening 1304 and zero instances of the first opening 1302 and the third opening 1306. The housing 302 may include two instances of the third opening 1306 and zero instances of the first opening 1302 and the second opening 1304. The housing 302 may include other combinations of the openings and/or additional instances of the openings.

The first opening 1302 may be shaped to fit a light source (e.g. a set of light-emitting diodes (LEDs)). For example, a substrate on which the LEDs are mounted may be circular. The first opening 1302 may be circular and may have a same size as the substrate. The second opening 1304 may be shaped to fit a first type of the physiological sensor 206 such as the first sensor 112. The third opening 1306 may be shaped to fit a second type of the physiological sensor 206 such as the second sensor 114. The LEDs may be disposed within the housing 302, aligned with the first opening 1302, and/or may extend through the first opening 1302 from the housing 302. The first sensor 112 may be disposed within the housing 302, aligned with the second opening 1304, and/or may extend through the second opening 1304 from the housing. The first opening 1302, and therefore the LEDs, may be aligned with the second opening 1304 such that light emitted from the LEDs passes through the second opening 1304 and/or to the first sensor 112 after passing through the body part of the subject. The LEDs may be tuned to interrogate the body part of the subject, such as by emitting light within a range of wavelengths and/or frequencies. The first sensor 112 may be an optical sensor and/or may detect light passing through the second opening 1304 from the body part of the subject.

The first opening 1302, the second opening 1304, and/or the third opening 1306 may be formed in and/or through an outer wall 302f, e.g. a first wall, of the housing 302. Instances of the first opening 1302, the second opening 1304, and/or the third opening 1306 may be referred to separately as a first window, a second window, and so forth. For example, the housing 302 may include two instances of the second opening 1304, including a first window 1304a and a second window 1304b. The first window 1304a and the second window 1304b may be aligned with each other parallel to a depth 302j of the slot 302e. The first window 1304a and the second window 1304b may be aligned with each other parallel to a length 302k of the slot 302e. The first window 1304a may be separated from the second window 1304b by a distance ranging from one-sixteenth of an inch to half an inch. The first window 1304a may be separated from the second window 1304b by a distance corresponding to a diameter of a human vein or artery. A first instance of the second sensor 114 may be positioned in the housing 302, aligned with the first window 1304a, and/or may extend through the first window 1304a. A second instance of the second sensor 114 may be positioned in the housing 302, aligned with the first window 1304a, and/or may extend through the first window 1304a.

Instead of being openings that pass through the outer wall 302f of the housing 302, the first opening 1302, the second opening 1304, and/or the third opening 1306 may be a recess with a backing inset into the housing 302 above a plane of the inward-facing portion 302a. The backing may include electrical interconnects that electronically couple electronic components, such as the first sensor 112, the second sensor 114, and/or the light source to electronic components housed within the housing 302. Accordingly, the recesses may be formed in the housing 302 on the underside 302c of the housing 302. The slot 302e formed through the housing 302 may be formed between the recesses and the topside 302d of the housing 302.

The first sensor 112 may be positioned in the first window 1304a. The second sensor 114 may be positioned in the second window 1304b. Spacing between the first window 1304a and the second window 1304b, and therefore a position of the first sensor 112 in the housing 302 relative to the second sensor 114, may be such that, as the first sensor 112 is aligned with a vein and/or artery of the subject as the subject wears the band 106, the second sensor 114 may be positioned within a threshold distance of alignment with the vein and/or artery. For example, the first window 1304a and the second window 1304b may be spaced apart, center-to-center, by an amount ranging from 1 mm to 5 cm, from 1 mm to 10 mm, from 5 mm to 5 cm, from 5 mm to 2 cm, from 5 mm to 10 mm, and so forth.

The adjustable measurement device 300 may include a set of three or more sensors. The set of sensors may include a set of the same sensor type, e.g. three instances of the first sensor 112, and so forth. The set of sensors may include one or more instances of different sensor types, e.g. one instance of the first sensor 112 and two instances of the second sensor 114, and so forth. Having multiple instances of the same sensor, and/or combining multiple instances of the same sensor with one or more instances of another sensor type, may enable the adjustable measurement device 300 to identify a position of the physiological structure 204 of the subject and identify how the adjustable measurement device 300 should be moved to align one or more of the sensors with the physiological structure. The sensors may be fixed relative to each other such that a shift of the adjustable measurement device 300 shifts all the sensors. An indicator (e.g. the indicator 304) that instructs the subject to shift the adjustable measurement device 300 may indicate a shift of the first sensor instance, the second sensor instance, the third sensor instance, and so forth. The adjustable measurement device 300 may include the moveable sensor 602, and a shift instruction may indicate a shift of the moveable sensor 602 and not the other sensor instances.

Incorporating multiple sensors at different positions in the adjustable measurement device 300 may enable the adjustable measurement device 300 to measure multiple physiological characteristics of the subject. The adjustable measurement device 300 may be enabled by the multiple sensors to determine a position of one or more of the sensors relative to the physiological structure of the subject One sensor and information about an optimal SNR of the sensor may also be used to determine the position of the sensor relative to the physiological structure. The adjustable measurement device 300 may be enabled by the multiple sensors near each other to take measurements from the same physiological structure of the subject by different types of sensors. Using different types of sensors, the processing device 102 may be able to differentiate between portions of the signals that reflect different physiological characteristics, such as by multivariate analysis.

FIG. 13B illustrates another arrangement of the underside 302c of the housing 302 of the adjustable measurement device 300, according to an embodiment. Some of the features in FIG. 13B may be the same as or similar to some of the features in the other FIGS. described herein as noted by same and/or similar reference characters, unless expressly described otherwise. Additionally, reference may be made to features shown in any of the other FIGS. described herein and not shown in FIG. 13B.

On the outer wall 302f of the housing 302 and/or on the inward-facing portion 302a of the underside 302c of the housing 302, the second opening 1304 may be segmented into a first portion, e.g. the first window 1304a, and a second portion, e.g. the second window 1304b. The first window 1304a may be segmented from the second window 1304b by a divider 1308. The divider 1308 may have a width ranging from one sixty-fourth of an inch to one thirty-second of an inch. The first window 1304a and the second window 1304b may be configured to (e.g. may have length, width, and/or depth dimensions, may have mounting surfaces, may include mounting hardware, and so forth) receive one or more sensors. Similarly, the openings in general (e.g. the first openings 1302, the second opening 1304, the third opening 1306, and so forth) may be configured to receive one or more sensors. For example, the first window 1304a may be configured to receive a first optical sensor and the second window 1304b may be configured to receive a second optical sensor. The proximity of the first window 1304a to the second window 1304b may be such that light emitted by a light source through the first opening 1302 and traveling through a body part of the subject travels substantially the same distance to the first window 1304a as to the second window 1304b.

FIG. 13C illustrates a third arrangement of the underside 302c of the housing 302 of the adjustable measurement device 300, according to an embodiment. Some of the features in FIG. 13C may be the same as or similar to some of the features in the other FIGS. described herein as noted by same and/or similar reference characters, unless expressly described otherwise. Additionally, reference may be made to features shown in any of the other FIGS. described herein and not shown in FIG. 13C.

On the outer wall 302f of the housing 302 and/or on the inward-facing portion 302a of the underside 302c of the housing 302, the second opening 1304 may be aligned with the first opening 1302. A light source may be positioned in the first opening 1302 and a photosensor such as the first sensor 112 may be positioned in the second opening 1304. Two instances of the third opening 1306 may straddle the first opening 1302 and/or the second opening 1304. Impedance sensors such as the second sensor 114 may be positioned in the instances of the third opening 1306.

FIG. 13D illustrates a fourth arrangement of the underside 302c of the housing 302 of the adjustable measurement device 300, according to an embodiment. Some of the features in FIG. 13D may be the same as or similar to some of the features in the other FIGS. described herein as noted by same and/or similar reference characters, unless expressly described otherwise. Additionally, reference may be made to features shown in any of the other FIGS. described herein and not shown in FIG. 13D.

On the outer wall 302f of the housing 302 and/or on the inward-facing portion 302a of the underside 302c of the housing 302, the second opening 1304 may be aligned with the first opening 1302. A light source may be positioned in the first opening 1302 and a photosensor such as the first sensor 112 may be positioned in the second opening 1304. Two instances of the third opening 1306 may be positioned adjacent to the first opening 1302 and the second opening 1304 and may be similarly aligned with each other. Impedance sensor such as the second sensor 114 may be position in the third opening 1306.

Figure 14:
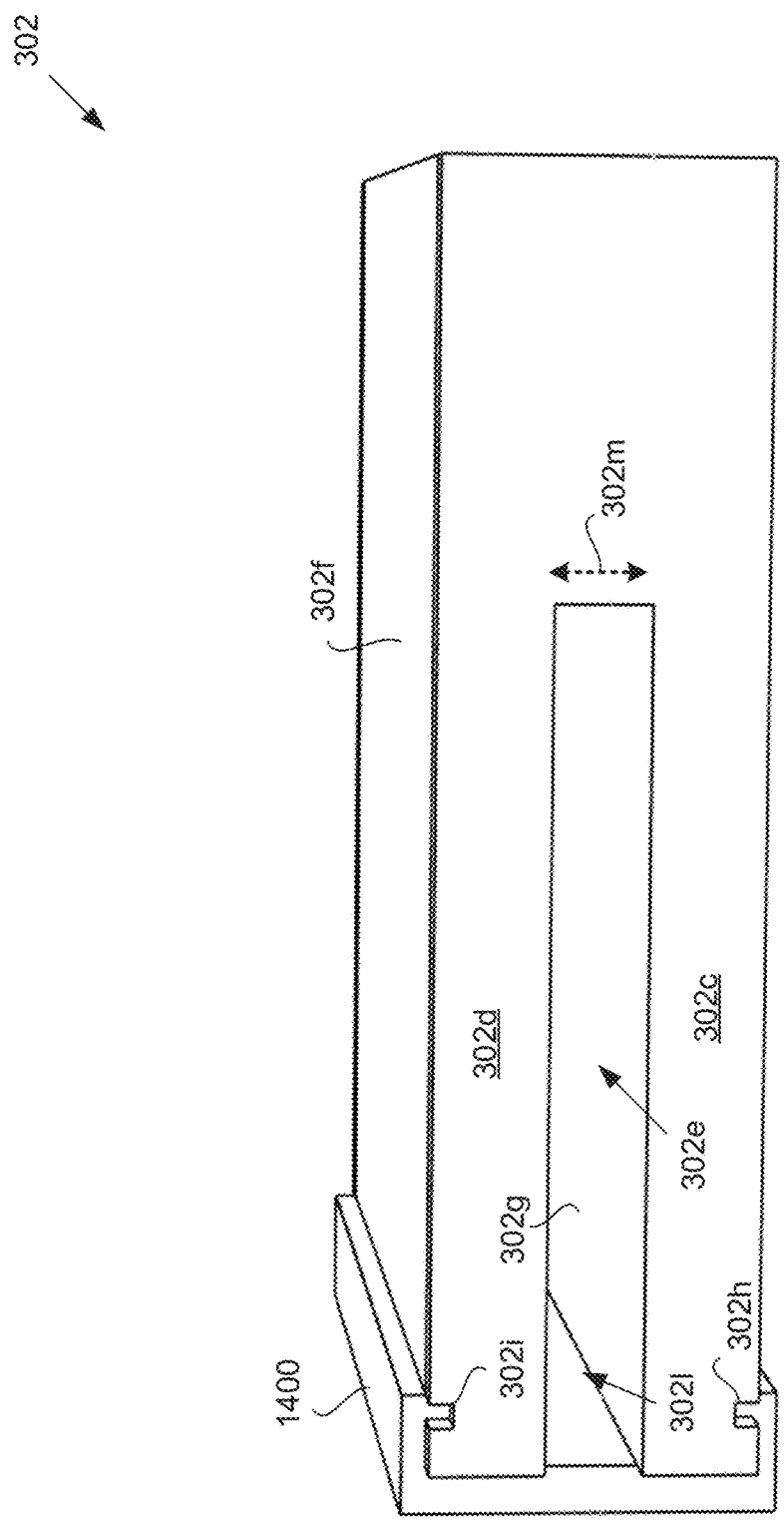
FIG. 14 illustrates a clamping mechanism for the adjustable measurement device, according to an embodiment.

FIG. 14 illustrates a clamping mechanism 1400 for the housing 302 of the adjustable measurement device 300, according to an embodiment. Some of the features in FIG. 14 may be the same as or similar to some of the features in the other FIGS. described herein as noted by same and/or similar reference characters, unless expressly described otherwise. Additionally, reference may be made to features shown in any of the other FIGS. described herein and not shown in FIG. 14.

The housing 302 may include a clamp, e.g. the clamping mechanism 1400. The clamping mechanism 1400 may be coupled to the housing 302 adjacent to an open end 302l of the slot 302e. A thickness 302m of the slot 302e with the clamping mechanism 1400 in a closed position may be less than the thickness 302m of the slot 302e with the clamping mechanism 1400 in an opened position. The slot 302e may receive the band 106. As the slot receives the band 106 and the clamping mechanism 1400 is in the closed position, the slot 302e may narrow such that an inner wall 302g of the housing 302 forms a frictional engagement with the band 106. As the inner wall 302g forms the frictional engagement with the band 106, the housing 302 may be affixed to the band 106 such that the housing 302 becomes immovable relative to the band 106. For example, as the subject wears the adjustable measurement device 300 and the band 106 and goes about activities such as exercise, walking, jogging, running, playing sports, sitting at a desk, and so forth, the housing 302 may not move relative to the band 106. As the clamping mechanism 1400 is in the open position, the housing 302 may be moveable on the band 106 such as by the subject sliding the housing 302 along the band 106 and/or by the subject removing the housing 302 from the band 106 while the band 106 remains on the body part of the subject.

The clamping mechanism 1400 may be a c-clamp that engages with a first slot 302h in the underside 302c of the housing 302 and a second slot 302i in the topside 302d of the housing 302. The slots may be adjacent to the open end 302l of the slot 302e in the housing 302 between the underside 302c and the topside 302d. The clamping mechanism 1400 may be fixed to one side of the housing 302, e.g. the underside 302c, and may include at the other side a catch. The other side of the housing 302, e.g. the topside 302d, may include a catch complimentary to the catch of the clamping mechanism. When the catches engage, the slot 302e may narrow and/or may squeeze the band 106 when the band is positioned in the slot 302e. The clamping mechanism 1400 may include a hinge at one side of the housing 302, e.g. the underside 302c, and the catch at the opposite side of the clamping mechanism. The clamping mechanism 1400 may include a magnet.

The clamping mechanism 1400 may enable the adjustable measurement device 300 to be attached to the band 106, removed from the band 106, and/or affixed in a position on the subject's body part. The band 106 may retain the adjustable measurement device 300 in a fixed position relative to the subject's body part.

Figure 15A:
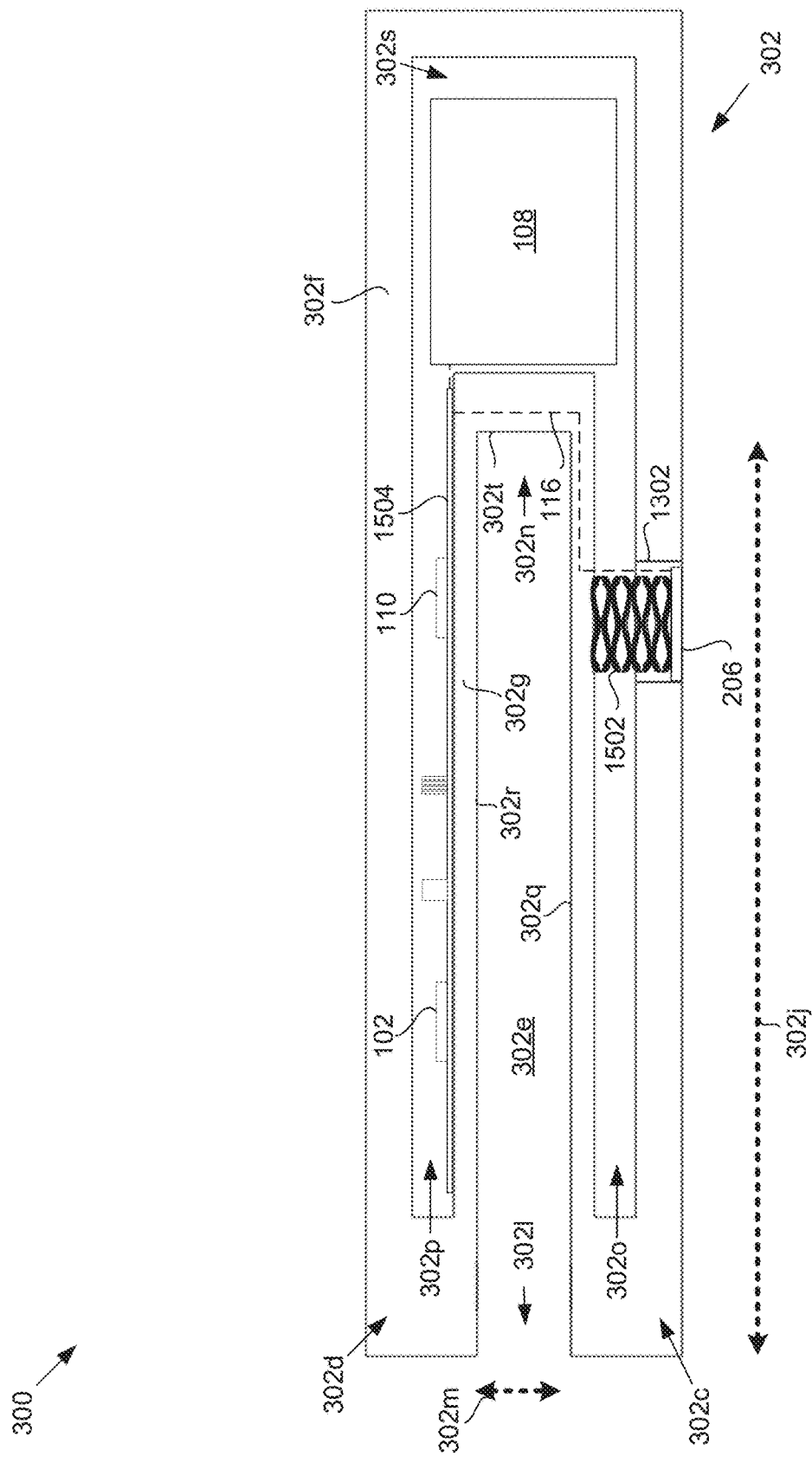
FIG. 15A illustrates a cross-section of the adjustable measurement device showing electronic components of the adjustable measurement device, according to an embodiment.

FIG. 15A illustrates a cross-section of the adjustable measurement device 300 showing electronic components of the adjustable measurement device 300, according to an embodiment. Some of the features in FIG. 15A may be the same as or similar to some of the features in the other FIGS. described herein as noted by same and/or similar reference characters, unless expressly described otherwise. Additionally, reference may be made to features shown in any of the other FIGS. described herein and not shown in FIG. 15A.

The housing 302 may include a first chamber 302o bordered by a first wall, e.g. the outer wall 302f, and a second wall 302q. The second wall 302q may be a portion of the inner wall 302g along the underside 302c of the housing 302. The first wall may include a sensor window, e.g. the first opening 1302. The sensor window may be the first opening 1302, the second opening 1304, the third opening 1306, and so forth. The housing 302 may include a second chamber 302p bordered by the outer wall 302f and a third wall 302r. The third wall 302r may be a portion of the inner wall 302g along the topside 302d of the housing 302. The slot 302e in the housing 302 may be positioned between the first chamber 302o and the second chamber 302p, e.g. the first chamber 302o may be positioned on the opposite side of the slot 302e from the second chamber 302p. The slot 302e may be bordered by the second wall 302q and the third wall 302r. The slot 302e may be separated from the first chamber 302o by the second wall 302q. The slot 302e may be separated from the second chamber 302p by the third wall 302r. The depth 302j of the slot 302e may range from one-quarter of an inch to two inches. The thickness 302m of the slot 302e may range from one thirty-second of an inch to one-quarter of an inch. The slot 302e may include the open end 302l and a closed end 302n opposite the open end 302l.

The housing 302 may include a third chamber 302s between and/or adjacent to the first chamber 302o and/or the second chamber 302p. The third chamber 302s may be at least partially enclosed by the outer wall 302f of the housing and the inner wall 302g of the housing. A fourth wall 302t may partially enclose the third chamber 302s. At least a portion of the fourth wall 302t may be a portion of the inner wall 302g extending between the second wall 302q and the third wall 302r. The fourth wall 302t may be perpendicular to the second wall 302q and/or the third wall 302r. The closed end 302n of the slot 302e may be defined by the fourth wall 302t. The fourth wall 302t may separate the slot 302e from the third chamber 302s. Boundaries between the chambers (e.g. the first chamber 302o, the second chamber 302p, and/or the third chamber 302s) and the slot 302e may be formed by the second wall 302q, the third wall 302r, and/or the fourth wall 302t.

The outer wall 302f of the housing 302 and/or the inner wall 302g of the housing 302 may be c-shaped, u-shaped, and so forth (i.e. c/u-shaped). The inner wall 302g may be nested in the outer wall 302f. The slot 302e may be defined by the c/u-shape of the inner wall 302g. The slot may thereby extend into the housing 302, where the closed-end 602e of the slot 302e is defined by the c/u-shaped inner wall 302g. The shape of the inner wall 302g and/or the outer wall 302f may be configured to extend at least partially around a width of the band 106, where the width of the band 106 may be along the same direction as the depth 302j of the slot 302e. The first chamber 302o, the second chamber 302p, and/or the third chamber 302s may be at least partially enclosed by the c/u-shaped inner wall 302g and the c/u-shaped outer wall 302f.

The physiological sensor 206 may be positioned in the first opening 1302 (i.e. the sensor window). An elastic coupling member 1502 may be disposed in the first chamber 302o and aligned with the first opening 1302. The elastic coupling member may be positioned against the second wall 302q. The elastic coupling member 1502 may be attached to, coupled to, and/or integrated with the second wall 302q. For example, the elastic coupling member 1502 may be adhered to the second wall 302q by glue. The elastic coupling member 1502 and the second wall 302q may be formed of the same material and may form a unitary piece of the housing 302. For example, the elastic coupling member 1502 and the inner wall 302g may be 3D-printed or manufactured by a plastic injection molding process. The first sensor 112 may be attached to the elastic coupling member 1502 at an end of the elastic coupling member 1502 opposite where the elastic coupling member 1502 is attached to the second wall 302*q*. The elastic coupling member 1502 and/or the first sensor 112 may be aligned with the first opening 1302. The elastic coupling member 1502 may have a spring property such that the elastic coupling member 1502 may respond with a reactionary force directed through the first opening 1302 away from the housing 302 when a causal force on the elastic coupling member 1502 is directed towards the second wall 302*q*. A force exerted by the elastic coupling member 1502 on the first sensor 112 may be in a direction through the first opening 1302 and/or away from the housing 302.

Electronic components of the adjustable measurement device 300 may be disposed in various locations throughout the first chamber 302*o*, the second chamber 302*p*, and/or the third chamber 302*s*. For example, the power source 108 may be positioned in the third chamber 302*s*, a PCB 1504 may be positioned in the second chamber 302*p*, and the elastic coupling member 1502 and first sensor 112 may be positioned in and/or adjacent to the first chamber 302*o*. The processing device 102 and communication device 110 may be positioned in the second chamber 302*p* and may be electronically interconnected to each other, the power source 108, and/or the first sensor 112 by a PCB 1504 and/or the electrical trace or circuit 116. The control/logic 300*a* and communication device 300*b* of the adjustable measurement device 300 may be interconnected on the PCB 1504. The power source 108 may be positioned in the first chamber 302*o* and/or the second chamber 302*p*. The power source 108 may include a cellular lithium-ion battery unit formed in the same shape as the inner wall 302*g* and/or the outer wall 302*f* of the housing 302 and may be attached to the inner wall 302*g* and/or the outer wall 302*f*. The power source 108 may be positioned in multiple chambers, e.g. may extend from the first chamber 302*o* through the third chamber 302*s* to the second chamber 302*p*.

The physiological sensor 206 may be electronically coupled to the power source 108. The physiological sensor 206 may have an integrated power management circuit. The physiological sensor 206 may be directly electronically coupled to the power source 108. The power management circuit for the physiological sensor 206 may be integrated into the control/logic 300*a* of the adjustable measurement device 300. The power management circuit for the physiological sensor 206 may be integrated into the processing device 102. The control/logic 300*a* and/or the processing device 102 may regulate the provision of power to the physiological sensor 206. The processing device 102, the control/logic 300*a*, the power source 108, and/or the physiological sensor 206 may be electronically interconnected via the PCB 1504 and/or the electrical trace and circuit 116.

The underside 302*c* of the housing 302 may be configured to be positioned between the band 106 and the subject's body part. For example, the underside 302*c* may be shaped to conform to the subject's body part. The adjustable measurement device 300 may include an indicator on the housing 302 of an orientation of the housing as the subject wears the band 106 and the adjustable measurement device 300. The first opening 1302 (and/or the second opening 1304, the third opening 1306, and so forth) may be adjacent to and/or may contact the subject, e.g. the subject's body part, as the subject wears the band 106 and the housing 302 is coupled to the band 106. The physiological sensor 206 may be adjacent to and/or may contact the subject, e.g. the subject's body part, as the subject wears the band 106 and the housing 302 is coupled to the band 106.

The housing 302 may be hollow. The electronic components of the adjustable measurement device 300 may be positioned within the hollow housing 302 in any of a variety of ways that enable efficient use of space within the housing 302 to minimize a volume and/or "footprint," e.g. surface area, of the housing 302. The sensing electronics such as the first sensor 112, the second sensor 114, the moveable sensor 602, and so forth may be positioned in the first chamber 302*o* to be aligned with the first opening 1302, the second opening 1304, the third opening 1306, and so forth. Room permitting, other electronic components of the adjustable measurement device 300, such as the processing device 102, the control/logic 300*a*, the communication device 300*b*, the power source 108, the PCB 1504, and so forth, may be positioned in the first chamber 302*o*. The other electronic components of the adjustable measurement device 300 may be spread out throughout the interior of the hollow housing 302 such as within the second chamber 302*p* and/or the third chamber 302*s*.

The communication device 300*b* may communicatively couple the internal electronic components of the adjustable measurement device 300 to the user device 118. For example, the electronic components of the adjustable measurement device 300 may include the control/logic 300*a*, the communication device 300*b*, the power source 108, and the physiological sensor 206. A measurement taken by the first sensor 112 may be processed by the control/logic 300*a* to increase the SNR of the signal associated with the measurement. The improved signal may be communicated by the communication device 300*b* to the user device 118, such as via the communication device 110. The processing device 102 may determine a measurement value based on the improved signal. The user device 118 may include the user interface 104, and the user interface 104 may present the measurement value to the subject.

The shape of the housing 302 and the positioning and/or shape of the chambers in the housing 302 may minimize the footprint of the housing 302 and optimize the measurement-taking capabilities of the adjustable measurement device 300. The slot 302*e* passing through the housing 302, instead of having a separate structure to attach the adjustable measurement device 300 to the band 106, may reduce the overall volume of the housing 302. The band 106 passing through the housing 302 and over the sensing electronics may allow for a constant downward force of the sensors against the subject's body part. The elastic coupling member 1502 may counter-balance the force by the band 106 to ensure the sensor is pressed against the subject with the correct amount of pressure in cases where the band may be too tight or too loose. The elastic coupling member 1502 may also ensure constant force of the sensor against the subject as the subject moves and engages in activity such as exercise, playing sports, and so forth. The band 106 may loosen or tighten on the subject as the subject's body part changes shape and/or volume due to movement of the subject. The elastic coupling member 1502 may maintain a constant force of the sensor against the subject as these changes to the subject's body part occur.

FIG. 15B illustrates a zoomed-in view of the cross-section illustrated in FIG. 15A, according to an embodiment. Some of the features in FIG. 15B may be the same as or similar to some of the features in the other FIGS. described herein as noted by same and/or similar reference characters, unless expressly described otherwise. Additionally, reference may be made to features shown in any of the other FIGS. described herein and not shown in FIG. 15B.

The pressure sensor 400 may be coupled to the physiological sensor 206, the elastic coupling member 1502, housing 302, and/or the band 106. For example, the pressure sensor 400 may be disposed within the first chamber 302*o* against the second wall 302*q* between the second wall 302*q* and the elastic coupling member 1502. As another example, the pressure sensor 400 may be disposed between the elastic coupling member 1502 and the physiological sensor 206. As another example, the pressure sensor 400 may be disposed in a recess in the band 106 between the elastic coupling member 1502 and the band 106 and/or between the physiological sensor 206 and the band 106. The pressure sensor 400 may thereby be configured to measure a pressure of the band 106 on the subject and/or a pressure of the physiological sensor 206 against the subject as the band 106 may be attached to the subject.

The pressure sensor 400 may be electronically coupled to the processing device 102, such as via the electrical trace or circuit 116, the PCB 1504, and so forth. The pressure sensor 400 may generate an electronic signal corresponding to a pressure of the physiological sensor 206 on the subject. The pressure sensor 400 may generate an electronic signal corresponding to a pressure of the physiological sensor 206 on the subject as the subject wears the band 106. The processing device 102 may convert the electronic signal into a pressure measurement. The pressure measurement may have a corresponding pressure measurement value. The pressure measurement value may be an absolute pressure measured by the pressure sensor 400 and may have units such as pounds per square inch. The pressure measurement value may be relative to a range of pressures. For example, the pressure measurement value may be represented as "within range," "good," "out of range," "high," "low," and so forth. The pressure measurement value may be a scalar, such as a normalized value that is normalized relative to an optimal pressure and/or an optimal range for the pressure. The optimal pressure range may have a minimum pressure and no maximum pressure. The optimal pressure range may have a maximum pressure and no minimum pressure.

The pressure sensor 400 may enable the subject to adjust the pressure of the band 106 and/or the adjustable measurement device 300 on the subject to an optimal pressure for the physiological sensor 206. The pressure sensor 400 may also enable the processing device 102, or another processing device, to determine how likely a physiological measurement value is to be accurate. If the physiological measurement is taken when the physiological sensor 206 is pressed against the subject with a pressure outside the range of optimal pressures, the physiological measurement may be tagged as being possibly inaccurate, the processing device 102 may prompt the physiological sensor 206 to take another measurement, the processing device 102 may prompt the physiological sensor 206 to take another measurement when the pressure is within the optimal range, the processing device 102 may discard the physiological measurement, the processing device 102 may adjust the value of the physiological measurement according to the pressure measurement value, and so forth. The physiological measurement value may vary as a function of the pressure with which the physiological sensor 206 is pressed against the subject.

FIG. 15C illustrates a zoomed-in view of the cross-section illustrated in FIG. 15A including light piping 1508, according to an embodiment. Some of the features in FIG. 15C may be the same as or similar to some of the features in the other FIGS. described herein as noted by same and/or similar reference characters, unless expressly described otherwise. Additionally, reference may be made to features shown in any of the other FIGS. described herein and not shown in FIG. 15C.

The PCB 1504 may be positioned in the first chamber 302*o*. A light source 1506 may be mounted to the PCB 1504. The light source 1506 may be aligned with one of the openings in the outer wall 302*f*, such as the first opening 1302. The light piping 1508 may be coupled to the first opening 1302. The light piping 1508 may extend into the first chamber 302*o*. The light source 1506 may be tuned to interrogate a body part of the subject. For example, the light source 1506 may include LEDs that emit light including a range of wavelengths. The range of wavelengths may include individual wavelengths that are either strongly absorbed by the physiological structure 204 of the subject and/or strongly reflected by the physiological structure.

The light piping 1508 may isolate the light source 1506 from internal components of the adjustable measurement device 300 including sensors. The light piping may extend from the first opening 1302 to the PCB 1504. The light piping may contact the PCB 1504 and may form an optical seal with the PCB 1504. The light piping 1508 may direct light emitted by the light source 1506 towards the subject. The adjustable measurement device 300 may include optical sensors that interrogate the physiological structure of the subject by detecting wavelengths of light reflected from the physiological structure. Light entering the optical sensor from outside the subject's body may distort measurements of the subject's physiological condition because the light may wash out light received from the subject's body, increase noise in light received by the optical sensors, and so forth.

The first opening 1302 may be open such that the light source 1506 is directly exposed to an ambient environment outside the housing 302. The first opening 1302 may include a transparent covering between the light source 1506 and the ambient environment outside the housing 302. The transparent covering may be transparent to light emitted by the light source 1506. The physiological sensor 206, such as the first sensor 112, may be similarly situated such that the light piping 1508 sequesters the physiological sensor 206 from other internal components of the adjustable measurement device 300. For example, the physiological sensor 206 may be a photodiode and/or another photo detector. The light piping 1508 may prevent light noise, such as light emitted from other electronic components with the housing 302, from reaching the physiological sensor 206.

Figure 16A:
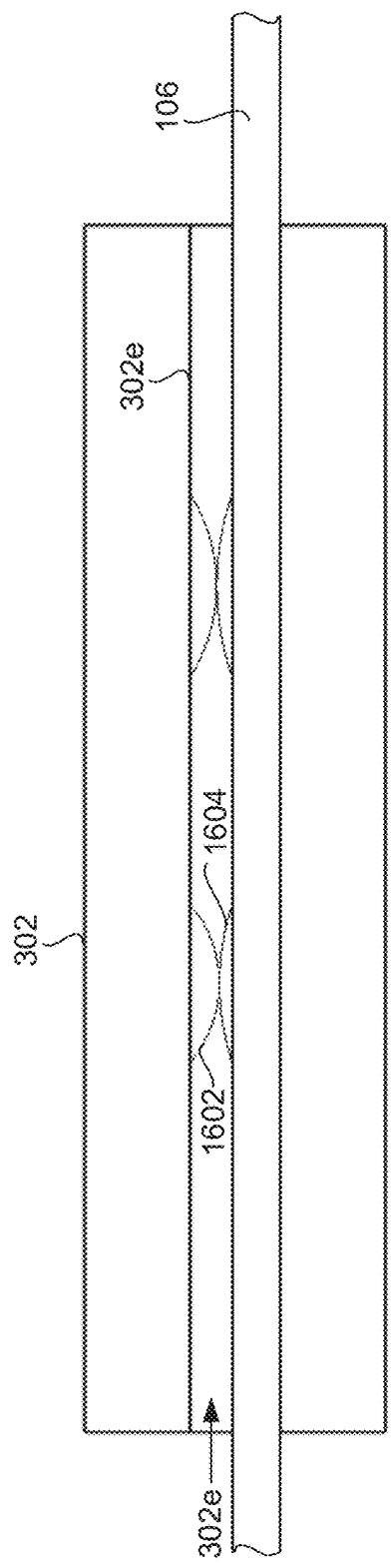
FIG. 16A illustrates a side view of the adjustable measurement device on the band of the wearable device, according to an embodiment.

FIG. 16A illustrates a side view of the adjustable measurement device 300 on the band of the wearable device, according to an embodiment. Some of the features in FIG. 16A may be the same as or similar to some of the features in the other FIGS. described herein as noted by same and/or similar reference characters, unless expressly described otherwise. Additionally, reference may be made to features shown in any of the other FIGS. described herein and not shown in FIG. 16A.

The adjustable measurement device 300 may include electrical contacts 1602 disposed on the inner wall 302*g* within the slot 302*e* of the housing 302. For example, the electrical contacts 1602 may be disposed on the second wall 302*q* and/or on the third wall 302*r*. The band 106 may include exposed conductive tracing 1604 (e.g. electrical contact surfaces). The electrical contacts 1602 of the adjustable measurement device 300 may be electrically interconnected to the electronic components of the adjustable measurement device 300. For example, the electrical contacts 1602 may be electrically coupled to the physiological sensor 206, the power source 108 (when, for example, the power source 108 is disposed in the housing 302), and/or the processing device 102, and so forth via the PCB 1504 and/or the electrical trace or circuit 116. The exposed conductive tracing 1604 of the band 106 may be electrically coupled to the user device 118, the power source 108 (when, for example, the power source 108 is disposed outside the housing 302), and/or an inductor in the band 106, and so forth. The inductor may be an inductive charging device.

The electrical contacts 1602 and the exposed conductive tracing 1604 may transfer power between the adjustable measurement device 300 and the band 106. For example, the power source 108 may be positioned in the band 106 and/or the user device 118 which may be attached to the band 106. Power may be delivered to internal electronic components of the adjustable measurement device 300, such as the control/logic 300a, the communication device 300b, the physiological sensor 206, and so forth, from the power source 108 outside the housing 302 via the electrical contacts 1602 and the exposed conductive tracing 1604. The exposed conductive tracing 1604 may be electrically coupled to the power source 108. The exposed conductive tracing 1604 may form electrical contact with the electrical contacts 1602 of the adjustable measurement device 300. As another example, the processing device 102 may be positioned in the band 106. The processing device 102 may communicate instructions to the physiological sensor 206 in the adjustable measurement device 300 via the electrical contact between the electrical contacts 1602 of the adjustable measurement device 300 and the exposed conductive tracing 1604 of the band 106. As another example, the power source 108 may be positioned in the housing 302. The power source 108 may be a battery. A charging mechanism for the battery, such as an inductor, may be positioned in and/or integrated with the band 106 and/or the user device 118. The battery may be charged using the inductor via the electrical contacts 1602 of the adjustable measurement device 300 and the exposed conductive tracing 1604 of the band 106.

It may be beneficial to spread electronic components of the wearable device 100, including those of the adjustable measurement device 300, to as many areas of the wearable device 100 as possible to minimize the footprint of the wearable device 100 and/or the adjustable measurement device 300. This may include putting the processing device 102 and power source 108 outside the user device 118 and adjustable measurement device 300 and in the band 106. The arrangement of electrical contacts 1602 aligned with the exposed conductive tracing 1604 of the band may enable the adjustable measurement device 300 to be adjustable on the band 106 while still delivering power and/or control instructions from the processing device 102 and/or power source 108 to the adjustable measurement device. The exposed conductive tracing 1604 may have a length of exposure from the band 106 that may correspond to, e.g. may determine, an adjustable range for the position of the adjustable measurement device 300 on the band 106.

Figure 16B:
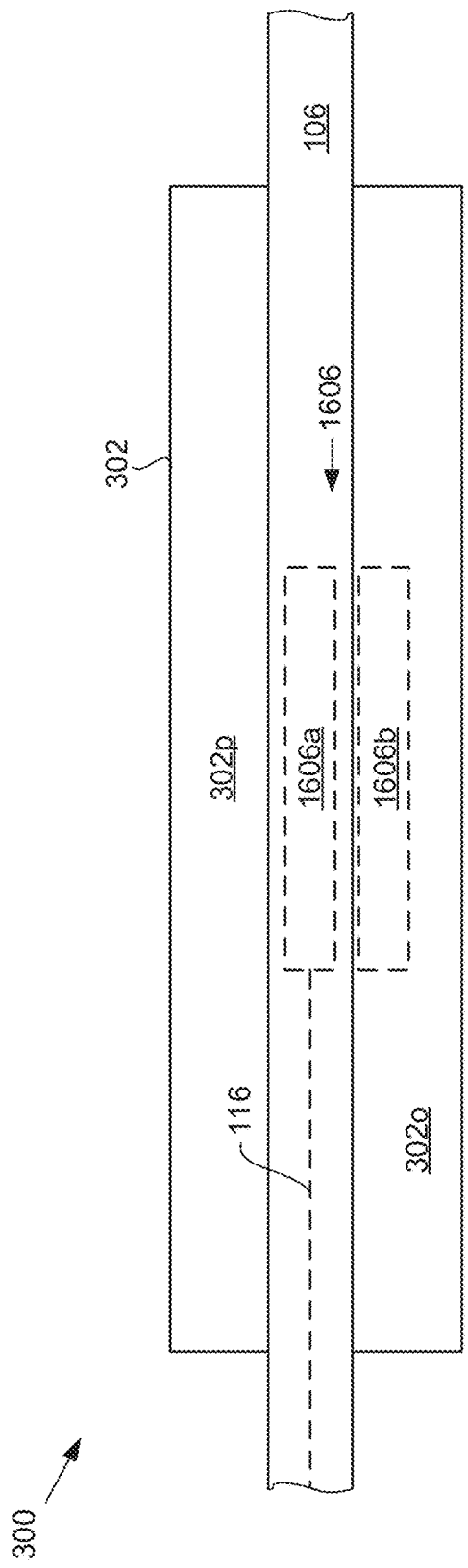
FIG. 16B illustrates a side view of the adjustable measurement device on the band of the wearable device including a wireless charging system, according to an embodiment.

FIG. 16B illustrates a side view of the adjustable measurement device 300 on the band 106 of the wearable device 100 and includes a wireless charging system 1606, according to an embodiment. Some of the features in FIG. 16B may be the same as or similar to some of the features in the other FIGS. described herein as noted by same and/or similar reference characters, unless expressly described otherwise. Additionally, reference may be made to features shown in any of the other FIGS. described herein and not shown in FIG. 16B.

The wireless charging system 1606 may include a first wireless charging device 1606a positioned in the band 106 and a second wireless charging device 1606b positioned in the housing 302 of the adjustable measurement device 300 approximate to the slot 302e. The second wireless charging device 1606b may be electronically coupled to various electronic components of the adjustable measurement device 300, and the first wireless charging device 1606a may be electronically coupled to various electronic components outside the adjustable measurement device 300. For example, the second wireless charging device 1606b may be electronically coupled to the processing device 102 and/or the power source 108 in the housing 302. The user interface 104 may be integrated with the band 106. The first wireless charging device 1606a and the second wireless charging device 1606b may be configured to transfer power and/or data between each other. For example, the first wireless charging device 1606a and/or the second wireless charging device 1606b may include inductors. The processing device 102 and/or the power source 108 may be electronically coupled to the user interface via the wireless charging system 1606.

The wireless charging circuitry of the adjustable measurement device, e.g. the second wireless charging device 1606b, may be disposed in the first chamber 302o, the second chamber 302p, and/or the third chamber 302s. For example, the second wireless charging device 1606b may be positioned in the first chamber 302o adjacent to the second wall 302q. As another example, the second wireless charging device 1606b may be positioned in the second chamber 302p adjacent to the third wall 302r. As yet another example, the second wireless charging device 1606b may be positioned in the third chamber 302s adjacent to the fourth wall 302t. The first wireless charging device 1606a may be integrated into the band 106. The first wireless charging device 1606a may be incorporated into the band 106 to be flush with a surface of the band 106. The first wireless charging device 1606a may be integrated into the band 106 and may be positioned below the surface of the band 106 within the band 106.

The wireless charging system 1606 may enable the adjustable measurement device 300 to be removable from the band 106 while still being configured to be electronically coupled to electronic components of the band 106 and/or the user device 118. The band 106 may include several instances of the first wireless charging device 1606a so that the adjustable measurement device 300 may be adjusted in position relative to the band 106 while still being electronically coupled to the electronic components of the band 106 and/or the user device 118. For example, the band 106 may include two instances of the first wireless charging device 1606a, three instances of the first wireless charging device 1606a, four instances of the first wireless charging device 1606a, and so forth.

Figure 17:
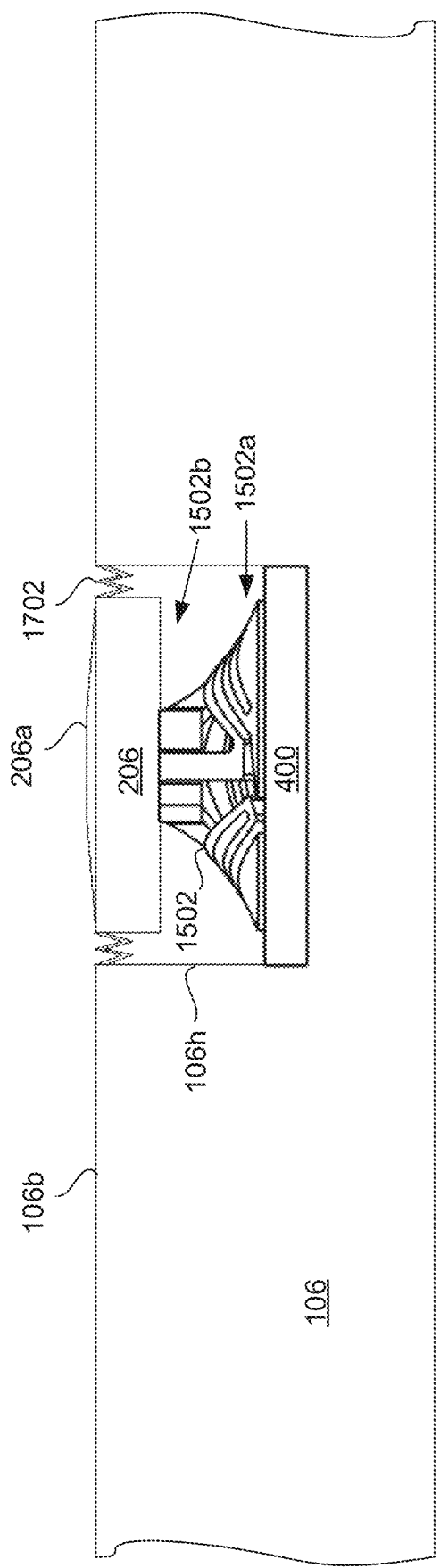
FIG. 17 illustrates a physiological sensor and an elastic coupling member embedded in the band, according to an embodiment.

FIG. 17 illustrates the physiological sensor 206 and the elastic coupling member 1502 embedded in the band 106, according to an embodiment. Some of the features in FIG. 17 may be the same as or similar to some of the features in the other FIGS. described herein as noted by same and/or similar reference characters, unless expressly described otherwise. Additionally, reference may be made to features shown in any of the other FIGS. described herein and not shown in FIG. 17.

The physiological sensor 206 may be embedded in and/or coupled to the band 106. The band 106 may include a recess 106h in the inward-facing surface 106a of the band 106. The elastic coupling member 1502 may be disposed within the recess 106h and/or may be attached to the band 106. A first end 1502a of the elastic coupling member 1502 may be attached to the band 106. A second end 1502b of the elastic coupling member 1502 may be attached to the physiological sensor 206. A flexible seal 1702 may be attached to the inward-facing surface 106a of the band 106 and the physiological sensor 206. The flexible seal 1702 may be attached to a surface within the recess 106h. The flexible seal 1702 and the physiological sensor 206 may cover the recess. The flexible seal 1702 and the physiological sensor 206 may seal off the recess from an ambient environment of the band 106. For example, the flexible seal 1702 may form a flexible hermetic and/or watertight seal with the sensor. The flexible seal 1702 and the physiological sensor 206 may prevent sweat, dirt, and/or oil from the subject's skin from accumulating in the recess 106h.

The processing device 102 may be coupled to the band 106, incorporated with a device attached to the band 106, and/or integrated into the band 106. The processing device 102 may be electronically coupled to the physiological sensor 206, such as via the electrical trace or circuit 116, the PCB 1504, and so forth. The physiological sensor 206 may be configured to generate an electronic signal corresponding to a physiological state of a subject as the band 106 is attached to the subject. The processing device 102 may be configured to receive the electronic signal and convert the electronic signal to a physiological measurement corresponding to the physiological state of the subject.

The physiological sensor 206 may be integrated into the band 106 and/or embedded in the recess 106h of the band 106. A detection surface 206a of the physiological sensor 206 may be exposed on an underside of the band 106, e.g. the inward-facing surface 106a, that rests against a body part of the subject as the band 106 is attached to the subject. The detection surface 206a may be flush with the inward-facing surface 106a, e.g. the detection surface 206a may be coplanar with a plane of the inward-facing surface 106a. The detection surface 206a may be non-coplanar with the plane of the inward-facing surface 106a. For example, the detection surface 206a may be recessed within the band 106, or the detection surface 206a may extend outside of the band 106. If the physiological sensor 206 is fully recessed within the band 106, the physiological sensor 206 may be directly coupled to the band 106 without the elastic coupling member 1502. The open end of the recess 106h may press against the subject as the subject wears the band 106 to isolate the physiological sensor 206 from possible noise.

The recess 106h may extend into the band 106 from the inward-facing surface 106a towards the outward-facing surface 106b. As the subject wears the band 106, the elastic coupling member 1502 may press the physiological sensor 206 against the subject and may cause constant contact between the physiological sensor 206 and the subject. The housing 302 and/or the user device 118 may be attached to the band 106. The processing device 102 may be electronically coupled to the physiological sensor 206 and positioned in the housing 302 or the user device 118. The electrical trace or circuit 116 embedded in the band may extend from the physiological sensor 206 to the housing 302 or the user device 118. The electrical trace or circuit 116 may electronically couple the physiological sensor 206 to the processing device 102 and/or other electronic components of the wearable device 100 such as the user interface 104.

The recess 106h may include a closed end and an open end opposite the closed end. The closed end and the open end may have the same shape or a different shape. For example, the closed end and the open end may both be circular, rectangular, polygonal, and so forth. As another example, the closed end may be a first shape and the open end may be a second shape that is different from the first shape. The closed end may be circular, and the open end may be rectangular. A base of the elastic coupling member 1502 may be circular and may be the same size as the closed end of the recess 106h. The physiological sensor 206 may be rectangular and may fit within the open end of the recess 106h.

The physiological sensor 206 may be tiltable on the elastic coupling member 1502. The physiological sensor 206 may be tiltable relative to the band 106. The physiological sensor 206 may be tiltable relative to the inward-facing surface 106a of the band 106. The physiological sensor 206 may be tiltable from a plane parallel with the band 106 and/or the inward-facing surface 106a of the band 106 by up to 30 degrees. The physiological sensor 206 may be tiltable on the elastic coupling member 1502 from the plane that is coplanar with the band 106 and/or the inward-facing surface 106a at 360 degrees around the physiological sensor 206, i.e. pressure on an edge of the physiological sensor 206 at any point around the physiological sensor 206 may cause the physiological sensor 206 to tilt on the elastic coupling member by up to 30 degrees.

The recess 106h may be configured such that the physiological sensor 206 fits snugly within the recess 106h. For example, the physiological sensor 206 may have a clearance fit within the recess 106h within a range of tolerance. The clearance fit may be with respect to a width of the physiological sensor 206 and a width of the recess 106h. The range of tolerance of the clearance fit may range from 0.25 mm to 2 mm on each side of the physiological sensor 206 between the physiological sensor 206 and the walls of the recess 106h.

The elastic coupling member 1502 may maintain the physiological sensor 206 in approximately constant contact with a body part of the subject as the subject wears the band 106 and as a pressure of the band against the body part changes. For example, the subject may wear the band 106 on the subject's wrist. The cross-sectional diameter of the subject's wrist may change as the subject moves, which may cause a change in the pressure of the band 106 against the subject's wrist. The elastic coupling member 1502 may compress as the pressure of the band 106 on the subject's wrist increases. The elastic coupling member 1502 may expand as the pressure of the band 106 on the subject's wrist decreases. The elastic coupling member may similarly maintain the physiological sensor 206 approximately coplanar with the body part as the subject wears the band 106 and as an alignment of the wearable band with the body part changes. For example, a plane of the inward-facing surface 106a of the band may be parallel to a plane of the subject's body part. As the subject engages in an activity, the plane of the inward-facing surface 106a may become non-parallel (e.g. intersecting) with the plane of the subject's body part. The elastic coupling member 1502 may press the physiological sensor 206 against the subject's body part and the pressure of the subject's body part on the physiological sensor 206 may cause the physiological sensor 206 to tilt relative to the plane of the inward-facing surface 106a of the band 106. The elastic coupling member 1502 may enable such tilting while still maintaining the physiological sensor 206 in constant contact with the subject's body part. A plane of the detection surface 206a may remain parallel with the plane of the body part as the plane of the inward-facing surface 106a is non-parallel with the plane of the body part.

The elastic coupling member 1502 may be an electrical conductor. The elastic coupling member 1502 may electronically couple the physiological sensor 206 to other electronic components of the wearable device 100 such as the processing device 102. For example, the elastic coupling member 1502 may be made of steel. The elastic coupling member 1502 may be electrically coupled to the electronic components of the physiological sensor 206 and may be electrically coupled to the electrical trace or circuit 116.

The physiological sensor 206 may be positioned adjacent to the inward-facing surface 106a of the band. For example, the physiological sensor 206 may be embedded within the band 106. The strain in the band 106 may indicate a pressure of the physiological sensor 206 against the subject. The strain may be measured by a strain gauge in the band 106, e.g. the pressure sensor 400 may be embedded in the band 106. The physiological sensor 206 may be set in the recess 106h. The pressure sensor 400 may also be set in the recess 106h. The pressure sensor 400 may be coupled to the band 106. The pressure sensor 400 may be positioned between the band 106 and the elastic coupling member 1502. The pressure sensor 400 may be positioned between the elastic coupling member 1502 and the physiological sensor 206. The pressure sensor 400 may be positioned to measure a pressure with which the physiological sensor 206 is pressed into the band 106. The processing device 102 may be configured to receive an electronic signal from the pressure sensor 400 corresponding to the pressure on the physiological sensor 206 or the strain in the band 106. The processing device 102 may be configured to generate a pressure measurement value representative of the pressure or the strain. The processing device 102 may be configured to compare the pressure measurement value to a first range of pressure values from a minimum pressure value to a maximum pressure value. The processing device 102 may be configured to generate an alert when the pressure measurement value is outside the first range of pressure values. The user interface 104 may be configured to receive the alert from the processing device 102 and generate an indicator for the alert. The user interface 104 may present the indicator to the subject.

Elements and/or features of how the physiological sensor 206 is incorporated into the band 106 may also be employed to incorporate the physiological sensor 206 into the housing 302 of the adjustable measurement device 300. The recess 106h may be positioned in the inward-facing portion 302a of the housing 302. The elastic coupling member 1502 may be mounted in the recess 106h on the inward-facing portion 302a of the housing 302. The physiological sensor 206 may be coupled to the elastic coupling member 1502 in the recess 106h. The elastic coupling member 1502 may press the physiological sensor 206 against the subject and cause constant contact between the physiological sensor 206 and the subject as the subject wears the adjustable measurement device 300 on the band 106.

The flexible seal 1702 may be disposed within one or more of the openings through the housing 302, such as the first opening 1302, and so forth. The flexible seal 1702 may be disposed between the second wall 302q and the physiological sensor 206. The flexible seal 1702 may form a watertight or hermetic seal between the second wall 302q wall and the physiological sensor 206. The flexible seal 1702 may permit the physiological sensor 206 to move in and/or through the opening as the elastic coupling member 1502 or skin of the subject presses against the physiological sensor 206.

Figure 18:
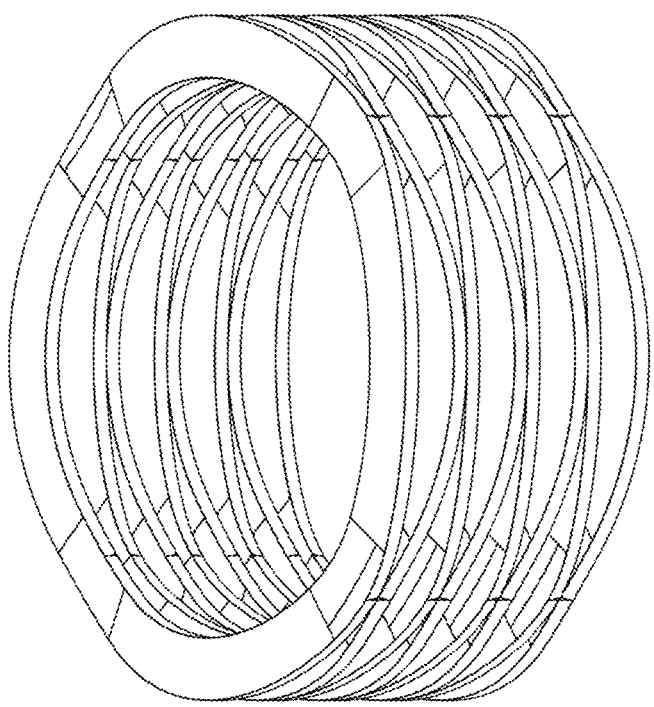
FIG. 18 illustrates a perspective view of a first type of an elastic coupling member, according to an embodiment.

FIG. 18 illustrates a perspective view of a first type of the elastic coupling member 1502, according to an embodiment. Some of the features in FIG. 18A may be the same as or similar to some of the features in the other FIGS. described herein as noted by same and/or similar reference characters, unless expressly described otherwise. Additionally, reference may be made to features shown in any of the other FIGS. described herein and not shown in FIG. 18A.

The elastic coupling member 1502 may be a spring. The elastic coupling member 1502 may be a coil spring. The elastic coupling member 1502 may be a wave spring. The elastic coupling member 1502 may be formed of a material formed in a shape that gives the material an elastic property. The elastic property may include the material having an equilibrium form, an extended form, and a compressed form. When the material is in the equilibrium form, the elastic coupling member 1502 is static. When the material is in the extended form the elastic coupling member 1502 exerts a contracting force. When the material is in the compressed form, the elastic coupling member 1502 exerts an expanding force. The material may include a metal such as steel and/or a plastic material.

Figure 19:
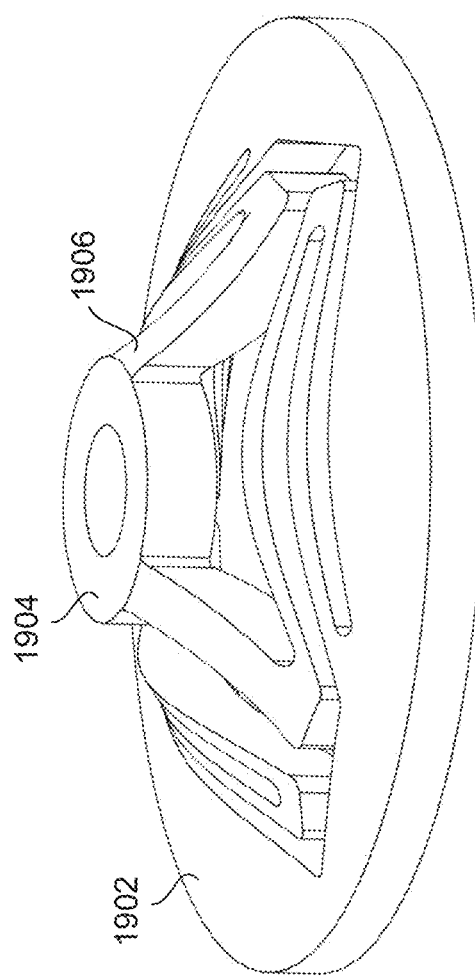
FIG. 19 illustrates a perspective view of a second type of the elastic coupling member, according to an embodiment.

FIG. 19 illustrates a perspective view of a second type of the elastic coupling member 1502, according to an embodiment. Some of the features in FIG. 19A may be the same as or similar to some of the features in the other FIGS. described herein as noted by same and/or similar reference characters, unless expressly described otherwise. Additionally, reference may be made to features shown in any of the other FIGS. described herein and not shown in FIG. 19A.

The elastic coupling member 1502 may be an ortho-conical spring. The ortho-conical spring may include a base end 1902. The base end 1902 may be configured to be coupled to the band 106 and/or the pressure sensor 400 in the recess 106h. For example, the base end 1902 may include an adhesive, hooks, a magnet, and so forth. The closed end of the recess may include complimentary attachment mechanisms. The base end 1902 may have a size and/or shape that matches the size and/or shape of the closed end of the recess 106h. The ortho-conical spring may have a mounting end 1904. The mounting end 1904 may be configured to be coupled to the physiological sensor 206. For example, the mounting end 1904 may include an adhesive, hooks, a magnet, and so forth. An underside of the physiological sensor 206 may include a complementary attachment mechanism. The mounting end 1904 may be smaller in length, width, and/or diameter than the base end 1902. The ortho-conical spring may include a leg 1906 that couples the base end 1902 to the mounting end 1904. A spring constant of the ortho-conical spring may be proportional to an inverse cube of a length of the leg 1906. The ortho-conical spring may have a height in an uncompressed equilibrium state of the ortho-conical spring that may be less than or equal to three-quarters of the length of the leg 1906. In a compressed state, the base end 1902, the mounting end 1904, and the leg 1906 may be coplanar. For example, the leg 1906 may be nested in the base end 1902 and the mounting end 1904 may be nested in the base end 1902 and the leg 1906. In an uncompressed equilibrium state, the ortho-conical spring may be conical.

The base end 1902 may be a recess end, where the base end 1902 is positioned in the recess 106h and attaches to the band 106. The mounting end 1904 may be a sensor end, where the mounting end 1904 attaches to the physiological sensor 206. The sensor end may be smaller than the recess end. For example, the recess end and the sensor end may be circular, and the sensor end may have a smaller diameter than the recess end. The sensor end may have a smaller diameter and/or surface area than the physiological sensor 206. The sensor end may be attached to the physiological sensor 206 at a center of a surface of the physiological sensor 206.

Figure 20:
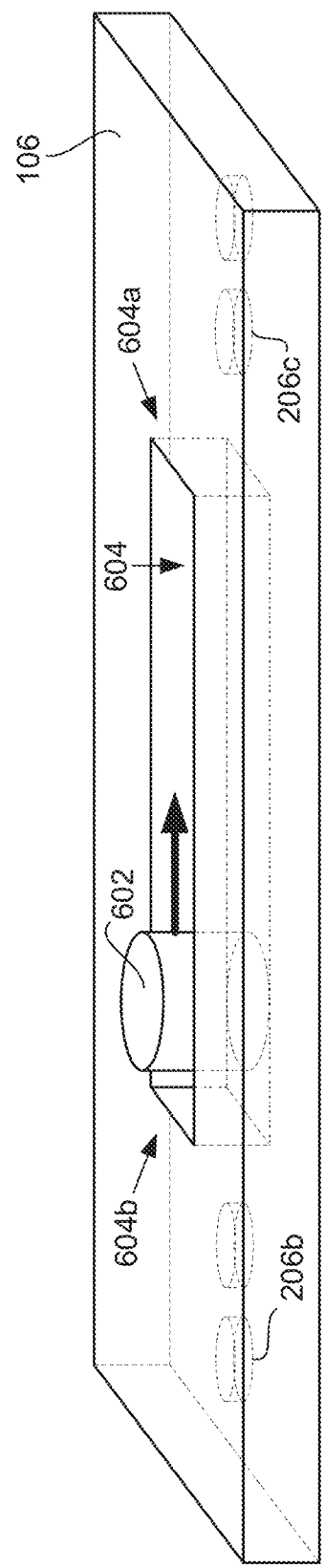
FIG. 20 illustrates the band with embedded physiological sensors and a moveable physiological sensor in the slot, according to an embodiment.

FIG. 20 illustrates the band 106 with embedded instances of the physiological sensor 206 and the moveable sensor 602 in the slot 604 of the band 106, according to an embodiment. Some of the features in FIG. 20 may be the same as or similar to some of the features in the other FIGS. described herein as noted by same and/or similar reference characters, unless expressly described otherwise. Additionally, reference may be made to features shown in any of the other FIGS. described herein and not shown in FIG. 20.

The band 106 may include the slot 604 and the moveable sensor 602 may be positioned in the slot 604. The slot 604 may be positioned in the band 106 along the length of the band 106 (i.e. the longer dimension of the band 106). The adjustable measurement device 300 may be attached to the band 106. The housing 302 may include the second chamber 302p and not the first chamber 302o. The underside 302c of the housing 302 may include the outer wall 302f and not the inner wall 302g. The outer wall 302f may be c-shaped and may wrap partially around the width of the band 106 so that the outer wall 302f extends part-way across the inward-facing surface 106a of the band 106. The outer wall 302f may not intersect with the slot 604. The housing 302 may be positioned against the outward-facing surface 106b of the band 106 over the slot 604. The openings in the housing, such as the first opening 1302, the second opening 1304, and/or the third opening 1306, may be through the third wall 302r portion of the inner wall 302g. At least one of the openings, such as the first opening 1302, may be aligned with the slot 604 as the housing 302 is attached to the band 106. The moveable sensor 602 may extend through, for example, the first opening 1302. As the housing 302 is attached to the band 106, the moveable sensor 602 may extend into and/or through the slot 604.

The moveable sensor 602 may be slidable in the slot 604 along the length of the slot 604 and/or the length of the band 106 as the adjustable measurement device 300 is attached to the band 106. The moveable sensor 602 may be fixed relative to the housing 302 and the housing 302 may be adjustable position-wise on the band 106. As the position of the housing 302 on the band 106 is adjusted along the length of the band 106 and/or the slot 604, the moveable sensor 602 may slide in the slot 604. The housing 302 may be fixed to the band 106. The first opening 1302 may have a length greater than a width of the first opening 1302. The length may extend parallel to the length of the slot 604. The position of the moveable sensor 602 in the first opening 1302 and the slot 604 may be adjustable relative to the band 106 and the housing 302. A lever extending from the housing 302 may be attached to the moveable sensor 602. The position of the moveable sensor 602 may be adjusted by moving the lever.

One or more instances of the physiological sensor 206 may be embedded in the band 106. Two instances of the physiological sensor 206 may be embedded in the band 106. Three instances of the physiological sensor 206 may be embedded in the band. Four instances of the physiological sensor 206 may be embedded in the band, and so forth. A first instance 206b of the physiological sensor 206 may be positioned at a first end 604a of the slot 604. A second instance 206c of the physiological sensor 206 or a first instance of another type of the physiological sensor 206 may be positioned at a second end 604b of the slot 604. The first end 604a and the second end 604b may be opposite length-wise ends of the slot 604 or opposite width-wise ends of the slot 604, e.g. sides of the slot 604. The first instance 206b and the second instance 206c may be fixed relative to each other and/or the band 106. The position of the moveable sensor 602 may be adjustable relative to the fixed positions of the first instance 206b and/or the second instance 206c. The processing device 102 may be configured to determine a shift of the moveable sensor 602 relative to the first instance 206b and/or the second instance 206c of the physiological sensor 206. For example, the processing device 102 may receive signals from the first instance 206b and the second instance 206c and may determine, based on the respective SNRs of the signals, a position of the physiological structure 204 between the first instance 206b and the second instance 206c. Based on the position of the physiological structure, the processing device 102 may output a recommended amount of shift of the moveable sensor 602 towards the first instance 206b or the second instance 206c of the physiological sensor 206.

The arrangement of the slot 604 and the moveable sensor 602 may enable fine-tuning of the sensing capabilities of the adjustable measurement device 300. The first instance 206b and the second instance 206c may identify the position of the physiological structure. The moveable sensor 602 may be placed in direct alignment with the physiological structure to maximize the SNR of the signal generated by the moveable sensor 602.

The first instance 206b of the physiological sensor 206 may be a photo sensor. The second instance 206c of the physiological sensor 206 may be a photo sensor. The moveable sensor 602 may be a light source (e.g. it is a sensor because it is part of a sensing system including the light source and the photo sensor). The photo sensors may straddle the light source. The first instance 206b and the second instance 206c may be light sources. The moveable sensor 602 may be a photo sensor.

Figure 21:
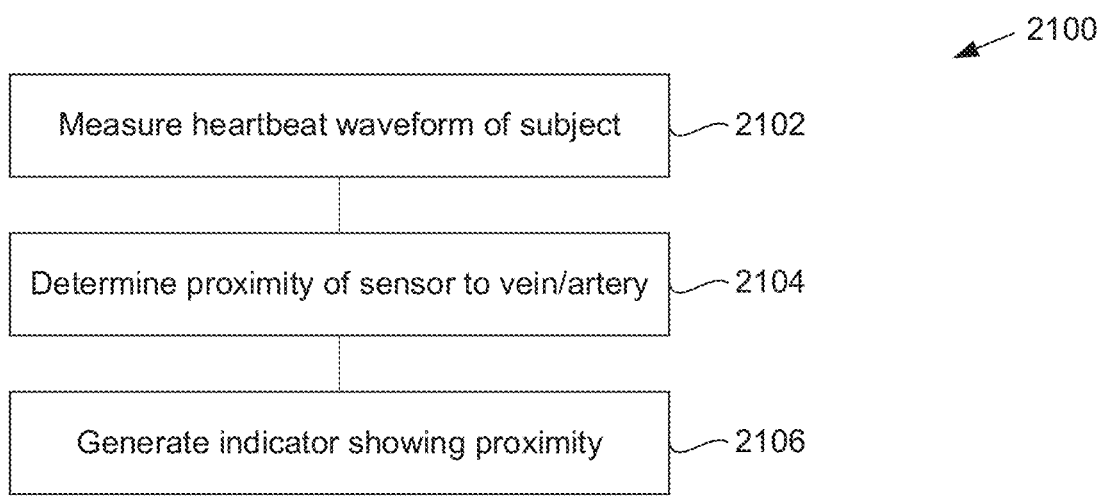
FIG. 21 illustrates a method of determining the physiological sensor's proximity to a physiological structure of the subject, according to an embodiment.

FIG. 21 illustrates a method 2100 of determining a sensor's proximity to a subject's vein and/or artery, according to an embodiment. Some of the features in FIG. 21 may be the same as or similar to some of the features in the other FIGS. described herein as noted by same and/or similar reference characters, unless expressly described otherwise. Additionally, reference may be made to features shown in any of the other FIGS. described herein and not shown in FIG. 21. Elements of the method 2100 may be executed in one or more ways such as by a human, including the subject, by a processing device such as the processing device 102, by mechanisms operating automatically or under human control such as the physiological sensor 206, and so forth.

The method 2100 may include measuring a heartbeat waveform of a subject (block 2102). The heartbeat waveform may be measured, for example, by a physiological sensor (e.g. the physiological sensor 206). The method 2100 may include determining a proximity of the physiological sensor to a physiological structure (e.g. the physiological structure 204) of the subject (block 2104). The physiological structure 204 may be a blood vessel, an organ, a muscle, a skeletal body, a muscular-walled tube, a vein, an artery, and so forth. The proximity may be determined by, for example, calculating a quality of the signal generated by the physiological sensor (e.g. a shape of the signal, an amplitude of the signal, an SNR of the signal, and so forth). The proximity may be determined by comparing the signal to a sample signal. The sample signal may have an ideal signal quality. The sample signal may be a signal generated when the proximity of the sensor to the physiological structure 204 is known to the subject and/or when the proximity is minimized. The sample signal may, for example, be an average best signal SNR, amplitude, shape, etc., averaged over a population of subjects. The population of subjects may have one or more physiological traits in common with the subject.

For example, the population of subjects may have the same age as the subject, may be in the same age range, may have the same gender, may have a similar gender, may have the same or a similar ethnicity, and so forth.

The method 2100 may include generating an indicator (e.g. the indicator 304) that signals to the subject (e.g. informs the subject of) the proximity of the physiological sensor to the physiological structure 204 (block 2106). The proximity may be determined by an amplitude of the signal that indicates the heartbeat waveform of the subject. An increasing amplitude may indicate increasing proximity of the physiological sensor to the physiological structure 204. The proximity may be determined by an SNR of the signal that indicates the heartbeat waveform. An increasing SNR may indicate increasing proximity of the physiological sensor to the physiological structure 204. The proximity may be determined by the shape of the signal over time, where the shape matches a shape of a previously measured heartbeat waveform. Better conformity of the shape with the shape of the previously measured heartbeat waveform may indicate increasing proximity of the physiological sensor to the physiological structure 204. The indicator may include a sound audible by the subject and/or a visual cue visible to the subject. The indicator may change as the proximity of the physiological sensor to the physiological structure 204 changes. The indicator may be an output by the adjustable measurement device 300 and/or the user device 118 communicatively coupled to the adjustable measurement device 300.

Figure 22:
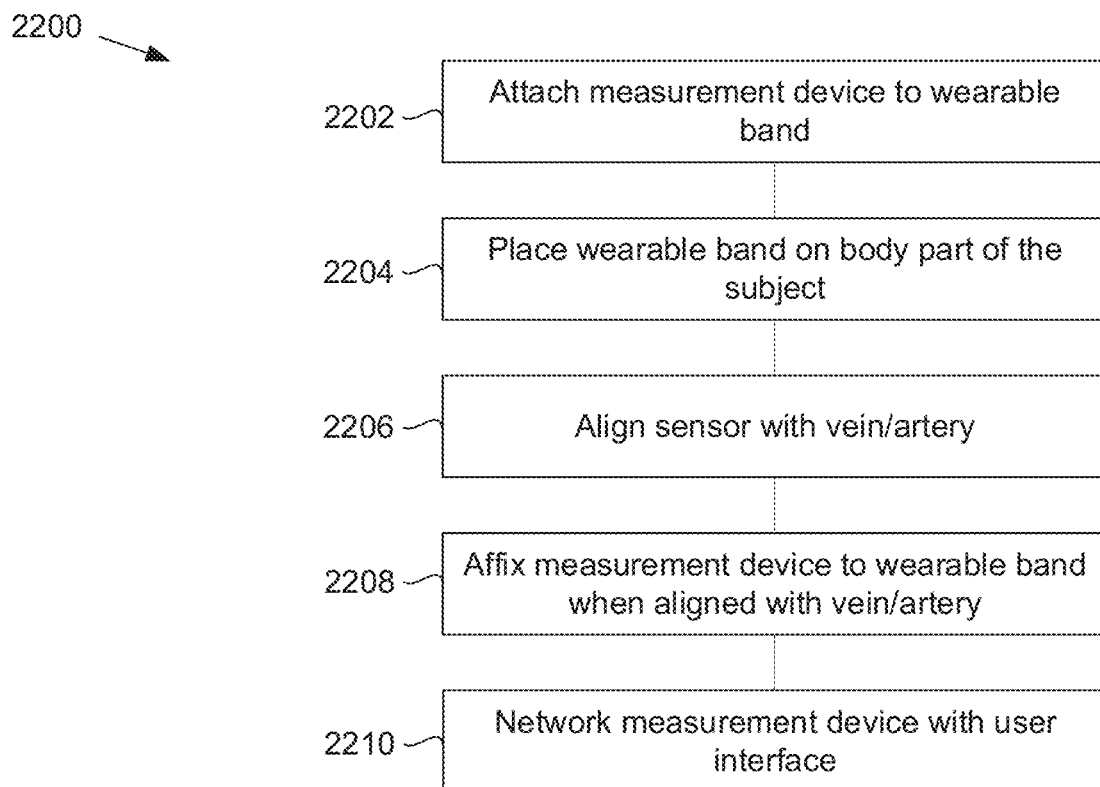
FIG. 22 illustrates a method of positioning the adjustable measurement device on the subject, according to an embodiment.

FIG. 22 illustrates a method 2200 of positioning the adjustable measurement device on the subject, according to an embodiment. Some of the features in FIG. 22 may be the same as or similar to some of the features in the other FIGS. described herein as noted by same and/or similar reference characters, unless expressly described otherwise. Additionally, reference may be made to features shown in any of the other FIGS. described herein and not shown in FIG. 22. Elements of the method 2200 may be executed in one or more ways such as by a human, including the subject, by a processing device such as the processing device 102, by mechanisms operating automatically or under human control such as the physiological sensor 206, and so forth.

The method 2200 may include attaching a measurement device (e.g. the wearable device 100 and/or the adjustable measurement device 300) to a wearable band that is wearable by a subject (e.g. the band 106) such that the measurement device is moveable on the wearable band (block 2202). The measurement device may include a housing formed in a shape that is complementary to a shape of a width of the wearable band (e.g. the housing 302). The housing may include an opening through a wall of the housing (e.g. the first opening 1302, and so forth). The measurement device may include a processing device disposed within the housing (e.g. the processing device 102, the control/logic 300a, and so forth). The measurement device may include an elastic coupling member (e.g. the elastic coupling member 1502) and/or a physiological sensor coupled to the elastic coupling member (e.g. the physiological sensor 206). The physiological sensor may be electronically coupled to the processing device and/or aligned with the opening. A force exerted by the elastic coupling member on the physiological sensor may be in a direction through the opening and away from the housing. The measurement device may include an attachment mechanism configured to attach the housing to the wearable band (e.g. the clamping mechanism 1400). As the subject wears the wearable band as the housing is attached to the wearable band, the physiological sensor and/or the opening may be adjacent to the subject's skin.

The method 2200 may include placing the wearable band on a body part of the subject such that the physiological sensor is pressed against the skin of the subject (block 2204). The physiological sensor may perform best, e.g. may generate the highest-quality signal, when the physiological sensor is pressed against the subject in an optimal range of pressures. The method 2200 may include aligning the physiological sensor with the physiological structure of the subject, such as a muscular-walled tube within the subject's body part (block 2206). The physiological sensor may be aligned with the subject's physiological structure when the signal quality output by the physiological sensor is maximized, such as by a maximum SNR and/or a maximum amplitude, and so forth. The method 2200 may include affixing the measurement device to the wearable band by the attachment mechanism (e.g. the clamping mechanism 1400) when the physiological sensor is aligned with the physiological structure (block 2208). The physiological sensor may be retained in alignment with the physiological structure of the subject by the wearable band.

The method 2200 may include communicatively coupling (e.g. networking) the measurement device with the user interface (block 2210). For example, the measurement device may be wirelessly networked to a user device such as a smartphone, a smartwatch, and so forth, via internal communication devices such as the communication device 110 and the communication device 300b. The measurement device may be hardwired to a user interface (e.g. the user interface 104) and/or a user device incorporating the user interface (e.g. the user device 118) via a circuit (e.g. the electrical trace and circuit 116). The user interface may be coupled to the wearable band or may be uncoupled from the wearable band. The user interface may be coupled to the wearable band separately from the measurement device, such as in a smartwatch on the wearable band. The user interface may be integrated with or integrated with a user device remote from the wearable band.

Figure 23:
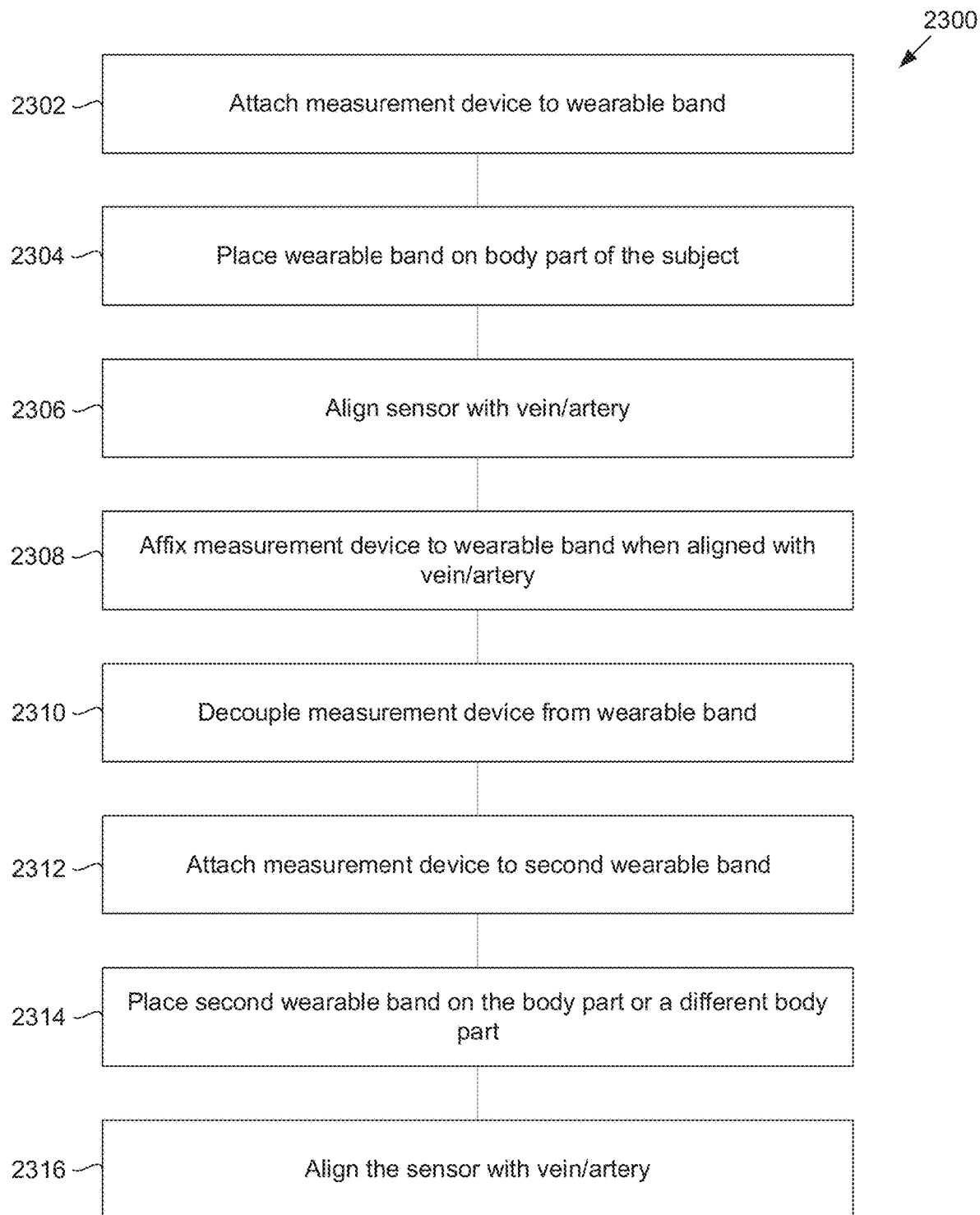
FIG. 23 illustrates a method of repositioning a measurement device on the subject, according to an embodiment.

FIG. 23 illustrates a method 2300 for repositioning the adjustable measurement device on the subject, according to an embodiment. Some of the features in FIG. 23 may be the same as or similar to some of the features in the other FIGS. described herein as noted by same and/or similar reference characters, unless expressly described otherwise. Additionally, reference may be made to features shown in any of the other FIGS. described herein and not shown in FIG. 23. Elements of the method 2300 may be executed in one or more ways such as by a human, including the subject, by a processing device such as the processing device 102, by mechanisms operating automatically or under human control such as the physiological sensor 206, and so forth.

The method 2300 may include attaching the measurement device to the wearable band (block 2302). The method 2300 may include placing the wearable band on the subject, such as on and/or around the body part of the subject (block 2304). The method 2300 may include aligning a physiological sensor of the measurement device (e.g. the physiological sensor 206) with a physiological structure of the subject, such as the muscular-walled tube, and so forth (block 2306). The wearable band may be stationary on the subject as the physiological sensor is aligned with the physiological structure and the measurement device may be adjusted positionwise on the wearable band. The method 2300 may include affixing the measurement device to the wearable band when the physiological sensor is aligned with the physiological structure (block 2308).

The method 2300 may include decoupling the measurement device from the wearable band (block 2310). The method 2300 may include attaching the measurement device to a second wearable band (block 2312). The second wearable band may include, for example, a second instance of the band 106 or another type of the band 106. The method 2300 may include placing the second wearable band on the same body part of the subject as the first wearable band was/is on or a different body part of the subject (block 2314). The method 2300 may include aligning the physiological sensor with the same physiological structure as the physiological sensor was previously aligned with (see, e.g., block 2306), a different physiological structure on the same body part of the subject, the same physiological structure on a different body part of the subject, or a different physiological structure of the different body part (block 2316).

Figure 24:
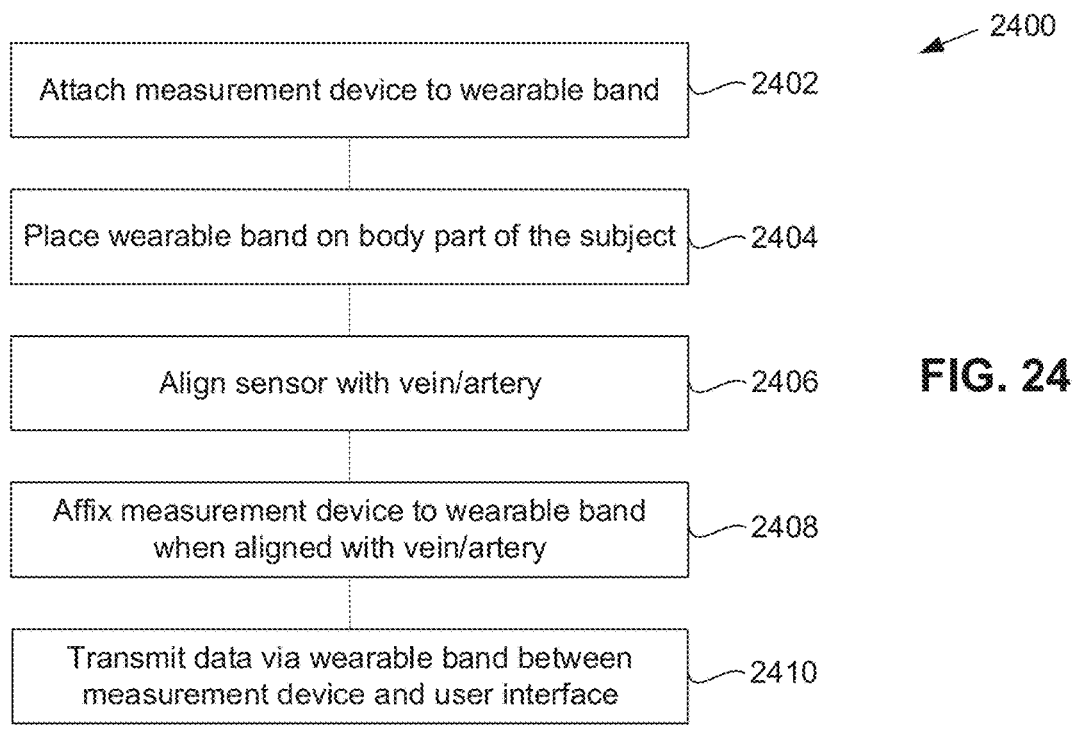
FIG. 24 illustrates a method of transmitting data between the adjustable measurement device and the user interface via the wearable device, according to an embodiment.

FIG. 24 illustrates a method 2400 of transmitting data between the adjustable measurement device and the user interface via the wearable device, according to an embodiment. Some of the features in FIG. 24 may be the same as or similar to some of the features in the other FIGS. described herein as noted by same and/or similar reference characters, unless expressly described otherwise. Additionally, reference may be made to features shown in any of the other FIGS. described herein and not shown in FIG. 24. Elements of the method 2400 may be executed in one or more ways such as by a human, including the subject, by a processing device such as the processing device 102, by mechanisms operating automatically or under human control such as the physiological sensor 206, and so forth.

The method 2400 may include attaching the measurement device to the wearable band (block 2402). The method 2400 may include placing the wearable band and the measurement device on a body part of the subject (block 2404). The method 2400 may include aligning a physiological sensor in the wearable band and/or the measurement device with a physiological structure of the subject such as a vein and/or artery of the subject (block 2406). The method 2400 may include affixing the measurement device to the wearable band when the physiological sensor is aligned with the physiological structure (block 2408). The wearable band may retain the physiological sensor in alignment with the physiological sensor. The method 2400 may include transmitting data via the wearable band between the measurement device and a user interface coupled to the wearable band (block 2410).

The measurement device may include a slot configured to extend at least partially around a width of the wearable band (e.g. the slot 302e). The wearable band may include a data line electronically coupled to the user interface (e.g. the electrical trace or circuit 116). The slot may include an electrical contact electronically coupled to the processing device and/or the sensor (e.g. electrical contact surfaces of the conductive tracing 1604). The data line may electronically couple to the electrical contact as the wearable band is positioned in the slot. Data may be transmitted via the data line.

Figure 25:
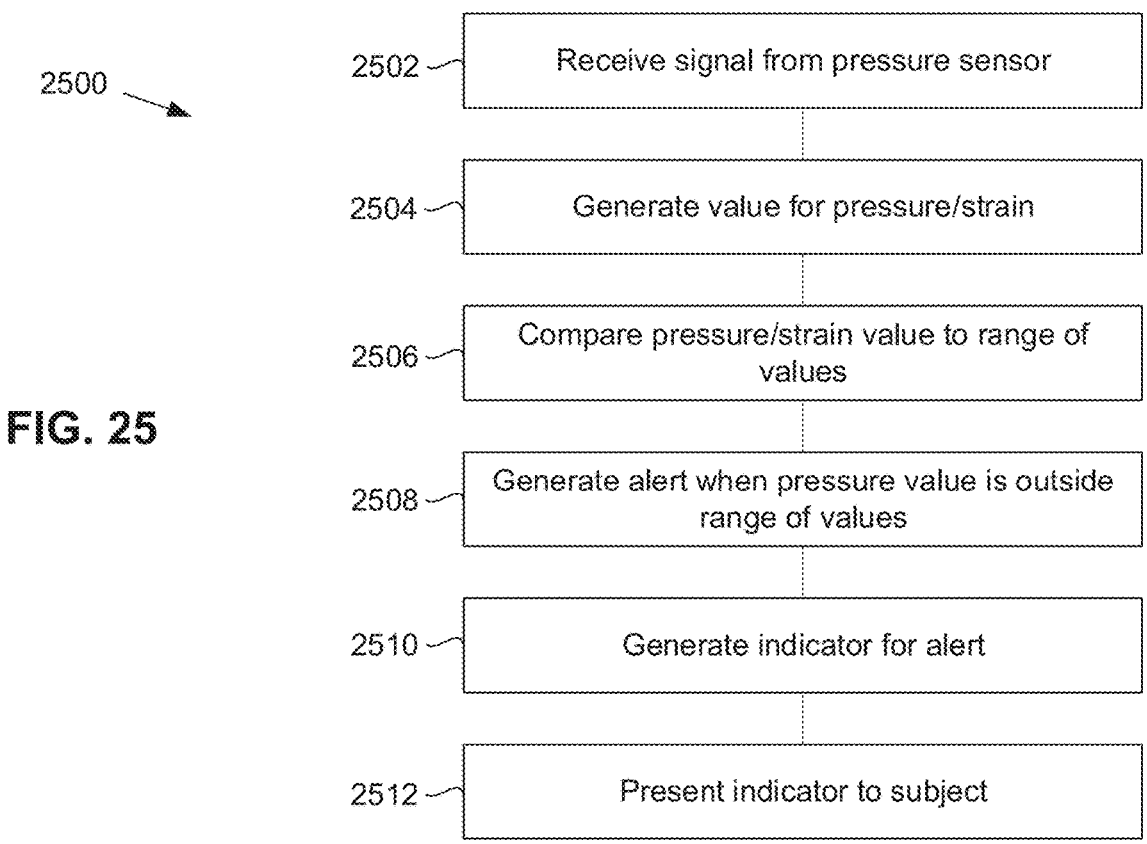
FIG. 25 illustrates a method of measuring a pressure of the physiological sensor against the subject, according to an embodiment.

FIG. 25 illustrates a method 2500 of measuring a pressure of the physiological sensor against the subject, according to an embodiment. Some of the features in FIG. 25 may be the same as or similar to some of the features in the other FIGS. described herein as noted by same and/or similar reference characters, unless expressly described otherwise. Additionally, reference may be made to features shown in any of the other FIGS. described herein and not shown in FIG. Elements of the method 2500 may be executed in one or more ways such as by a human, including the subject, by a processing device such as the processing device 102, by mechanisms operating automatically or under human control such as the physiological sensor 206, and so forth.

The method 2500 may include receiving a signal from a pressure sensor (e.g. the pressure sensor 400) (block 2502). The signal may correspond to a pressure value of the physiological sensor against the subject. The signal may correspond to a strain value of the wearable band on the subject. The method 2500 may include generating a value for the pressure/strain (block 2504). For example, the signal may indicate a resistivity of a strain gauge embedded in the wearable band. A processing device such as the processing device 102 may store and/or execute instructions to calculate the strain based on the resistivity. The processing device may output the strain value. The processing device may store and/or execute instructions to calculate a pressure value based on a capacitance of the pressure sensor. The processing device may be programmed with an algorithm that includes strain as a function of resistivity. The processing device may be programmed with an algorithm that includes pressure as a function of capacitance.

The signal from the pressure sensor may vary over time while the actual pressure of the physiological sensor against the subject remains constant. The variation in the pressure may be due to the volume of the body part to which, for example, the wearable device is attached may change. The volume change may be due to blood being pumped periodically through arteries in the body part of the subject. The periodic variation may be reflected in a periodic variation of the signal from the pressure sensor. The periodic variation of the signal from the pressure sensor may be translated by a processing device into a heartbeat waveform of the subject.

The method 2500 may include comparing the pressure and/or strain value to a range of pressure and/or strain values (block 2506). The range of pressure and/or strain values may be the optimal range within which the physiological sensor takes the best measurements, e.g. the range within which the SNR and/or amplitude of the signal produced by the physiological sensor is maximized when the physiological sensor is properly aligned with the physiological structure being interrogated by the physiological sensor. The method 2500 may include generating an alert when the pressure and/or strain falls outside the range for optimized measurement by the physiological sensor (block 2508). For example, the processing device may calculate a difference between the measured pressure and/or strain and a minimum pressure and/or strain. If the difference is positive, i.e. if the measured value is greater than the minimum value, the pressure may be determined to be greater than the minimum value. The processing device may calculate a difference between the measured value and a maximum value. If the difference is negative, i.e. if the measured value is less than the maximum value, the pressure may be determined to be less than the maximum value. If the measured value is determined to be less than the maximum value and greater than the minimum value, the pressure and/or strain may be determined to be in-range. If the measured value is either greater than the maximum value or less than the minimum value, the pressure and/or strain may be determined to be out-of-range. The pressure and/or strain may be in-range if it is equal to the minimum value or the maximum value. The alert may include notification content generated by the processing device, such as how far out of range the pressure and/or strain is. The alert may include a notification type, such as the pressure and/or strain is too high or too low.

The method 2500 may include generating an indicator for the alert (block 2510). The indicator may include one or more combined graphics. For example, the indicator may include a color-coded arrow that points up if the pressure and/or strain is too high or down if the pressure and/or strain is too low. The indicator may include an icon that indicates the measured value relative to the optimal range. The icon may be color-coded. The indicator may include characters and/or symbols that indicate an action to be performed by the subject, such as increasing the tightness of the wearable band, and so forth. The indicator may flash. The indicator may include sounds audible to the subject. The method 2500 may include presenting the indicator to the subject (block 2512). For example, the processing device may be electronically coupled to a user interface (e.g. the user interface 104). The user interface may be configured to emit the alert by presenting the indicator to the subject. For example, the user interface may include a visual display and/or a speaker.

Figure 26:
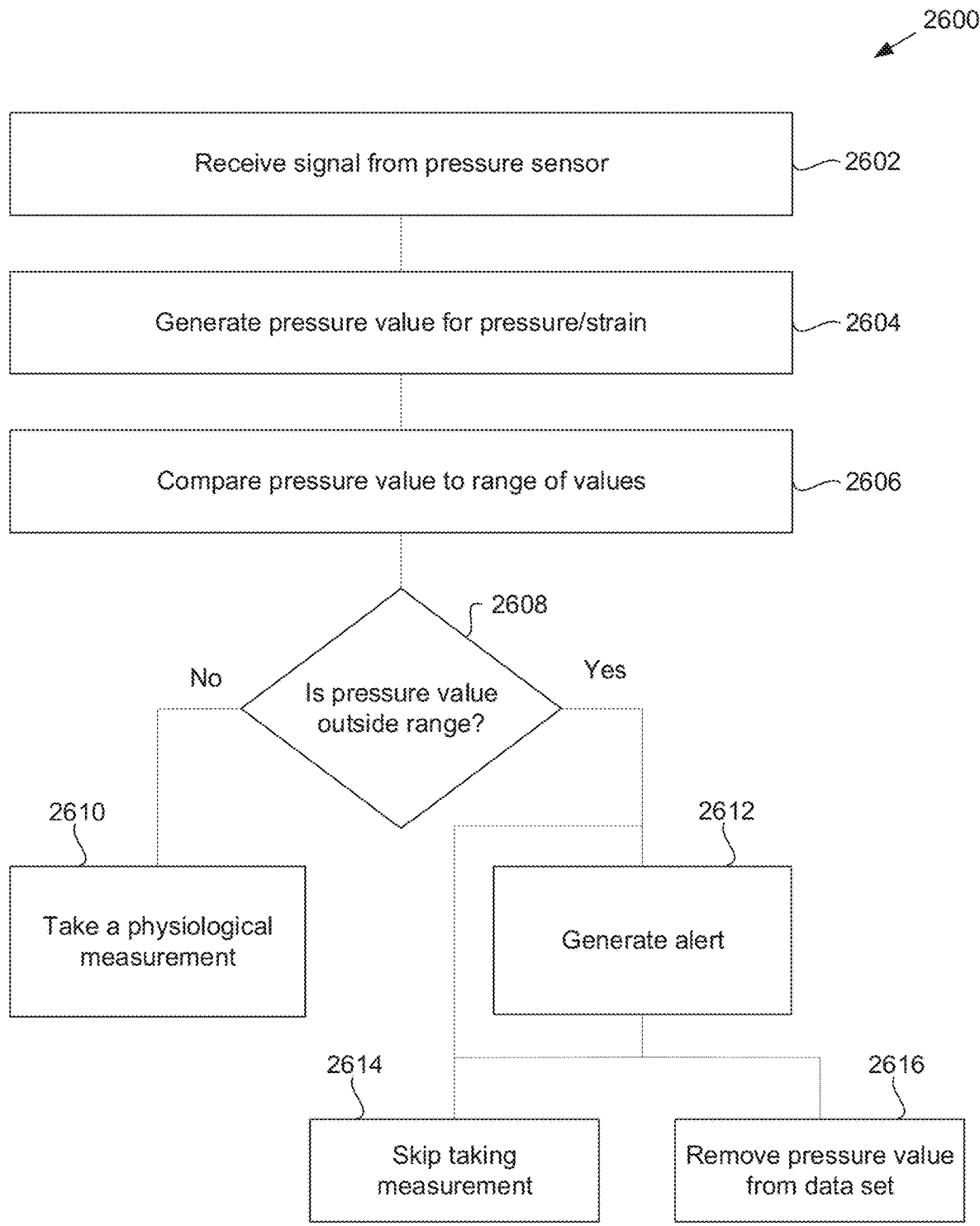
FIG. 26 illustrates a method of generating an alert when the physiological sensor is not pressed against the subject with enough pressure, according to an embodiment.

FIG. 26 illustrates a method 2600 of generating an alert when the physiological sensor is not pressed against the subject with enough pressure, according to an embodiment. Some of the features in FIG. 26 may be the same as or similar to some of the features in the other FIGS. described herein as noted by same and/or similar reference characters, unless expressly described otherwise. Additionally, reference may be made to features shown in any of the other FIGS. described herein and not shown in FIG. 26. Elements of the method 2600 may be executed in one or more ways such as by a human, including the subject, by a processing device such as the processing device 102, by mechanisms operating automatically or under human control such as the physiological sensor 206, and so forth.

The method 2600 may include receiving a signal from a pressure sensor (e.g. the pressure sensor 400) (block 2602). The method 2600 may include generating a value for the pressure and/or strain (block 2604). The method 2600 may include comparing the pressure and/or strain value to a range of pressure and/or strain values (block 2606). The method 2600 may include determining whether the pressure and/or strain value is outside the range of pressure and/or strain values (block 2608). The method 2600 may include taking a physiological measurement if the pressure and/or strain value is within the range of pressure and/or strain values (block 2610). For example, a processing device (e.g. the processing device 102) may be configured to take the physiological measurement by a physiological sensor when the measurement value of the pressure and/or strain is within the optimal range of pressure and/or strain values. The measurement device that includes the physiological sensor may thereby be enabled to interrogate a body part of the subject without distorting a physiological measurement generated by the measurement device.

The method 2600 may include generating an alert if the measured pressure and/or strain is outside the optimal range (block 2612). The method 2600 may include, in response to the measurement value of the pressure and/or strain being outside the range of optimal pressure and/or strain values, skipping taking the physiological measurement (block 2614). For example, the processing device may be programmed with a schedule for taking physiological measurements. The processing device may determine the measured pressure and/or strain is out-of-range and may cancel a scheduled measurement. The subject may request a measurement via a user interface electronically coupled to the processing device (e.g. the user interface 104). The processing device may be programmed to measure the pressure and/or strain after receiving instructions from the subject to take a physiological measurement. The processing device may be programmed to generate the alert and skip the requested physiological measurement if the measured pressure and/or strain is outside the optimal range. The processing device may be programmed to generate an indicator that indicates the physiological measurement was skipped and present the indicator to the subject.

The method 2600 may include removing the measured pressure and/or strain value from a data set of pressure and/or strain measurement values in response to the measured value being outside the optimal range (block 2616). For example, the processing device may be programmed to store measured pressure and/or strain values and correlate the measured values to physiological measurements taken at roughly the same time as the pressure and/or strain measurement. To prevent an inaccurate measurement from skewing statistical analysis of physiological measurements taken from the subject, the physiological measurement may be skipped, and the pressure and/or strain measurement may be removed from the data set.

Figure 27:
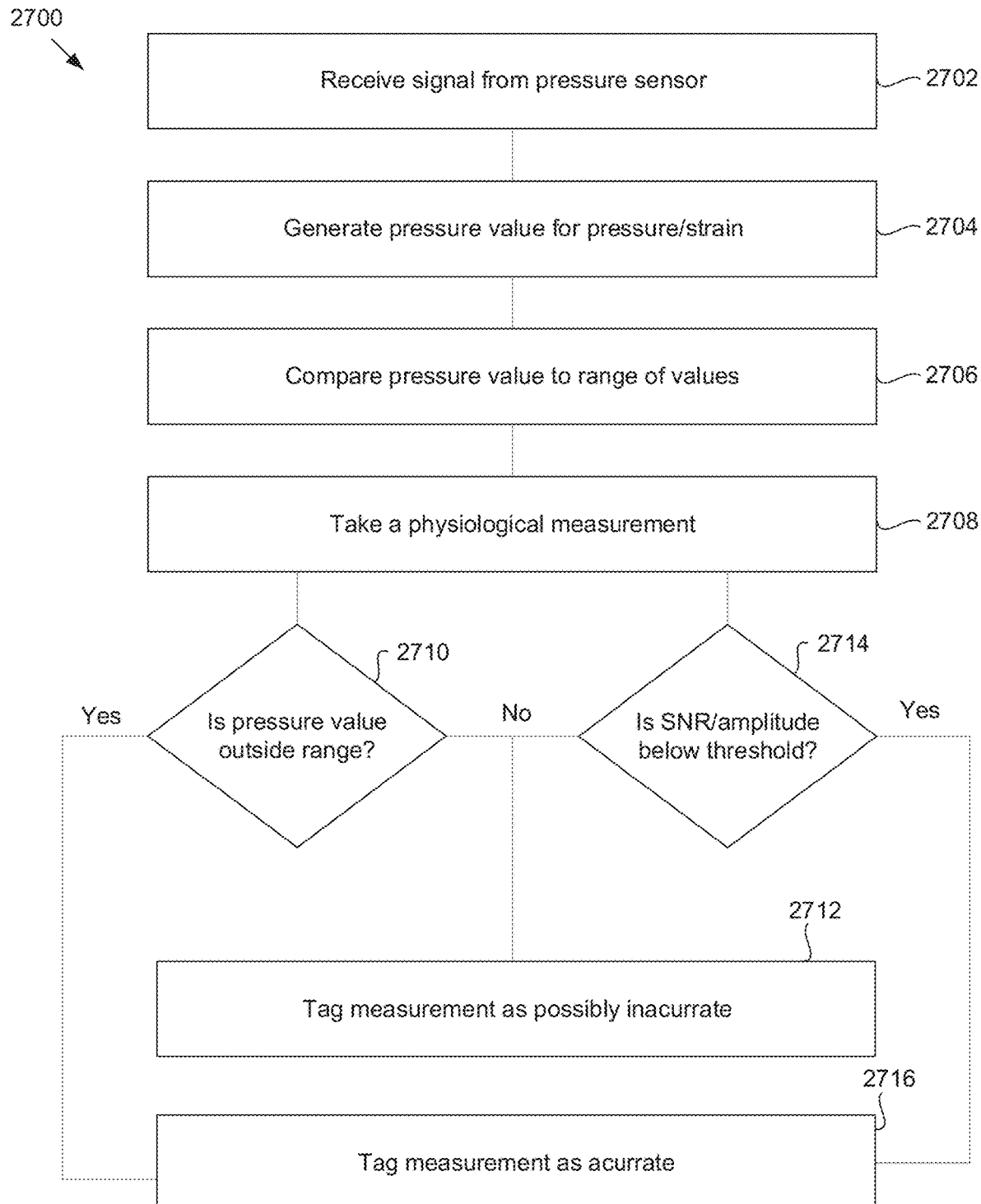
FIG. 27 illustrates a method of tagging a measurement as possibly inaccurate, according to an embodiment.

FIG. 27 illustrates a method 2700 of tagging a measurement as possibly inaccurate, according to an embodiment. Some of the features in FIG. 27 may be the same as or similar to some of the features in the other FIGS. described herein as noted by same and/or similar reference characters, unless expressly described otherwise. Additionally, reference may be made to features shown in any of the other FIGS. described herein and not shown in FIG. 27. Elements of the method 2700 may be executed in one or more ways such as by a human, including the subject, by a processing device such as the processing device 102, by mechanisms operating automatically or under human control such as the physiological sensor 206, and so forth.

The method 2700 may include receiving a signal from a pressure sensor (block 2702). The method 2700 may include generating a value for the pressure and/or strain (block 2704). The method 2700 may include comparing the pressure and/or strain value to an optimal range of pressure and/or strain values (block 2706). The method 2700 may include taking a physiological measurement (block 2708). The physiological measurement may be taken regardless of whether the measured pressure and/or strain falls within the optimal range. The method 2700 may include determining whether the measured pressure and/or strain is within the optimal range (block 2710). The method 2700 may include tagging the physiological measurement as possibly inaccurate if the measured pressure and/or strain is outside the optimal range (block 2712). For example, the processing device may generate a tag stored with the physiological measurement in a database. The tag may indicate whether the pressure and/or strain at the time the physiological measurement was taken fell within the optimal range. The tag may simply act as a flag that the physiological measurement may be inaccurate, where physiological measurements taken when the pressure and/or strain was in the optimal range do not have a tag.

The method 2700 may include determining whether the quality of the signal (e.g. the SNR and/or the amplitude of the signal) corresponding to the physiological measurement is above a threshold value for the signal quality (block 2714). The physiological measurement may be tagged as possibly inaccurate in response to the signal quality falling below the threshold value (e.g. block 2712). For example, the physiological measurement may be tagged as "bad." The bad physiological measurement may correspond to the signal generated by the measurement device (e.g. the physiological sensor in the adjustable measurement device 300) having a signal quality below the threshold level.

The method 2700 may include tagging the measurement as accurate when the pressure value is within the optimal range and/or the signal quality is above the threshold value for the signal quality (block 2716).

Tagging the physiological measurements may enable training and/or updating of an algorithm for determining the optimal pressure and/or strain range. For example, a data set including physiological measurements may include tagged and untagged measurements. Statistical analysis of the combined tagged-untagged data set may yield a variation and distribution of the physiological measurements. Statistical analysis of the untagged data set alone may yield a second variation and distribution of the untagged physiological measurements. If the two statistical analyses yield the same results, the optimal range for pressure and/or strain may be over-broad or not broad enough. If the two statistical analyses yield different results, e.g. if removing the tagged measurements eliminates skewing of the data by inaccurate measurements, the range may be confirmed as being optimal. Tagging the physiological measurements may enable training and/or updating of an algorithm for determining an optimal range of SNRs and/or amplitudes in a similar fashion. Tagging the physiological measurements may enable the processing device to discern between a bad SNR and/or low signal amplitude due to improper alignment and a bad SNR and/or low signal amplitude due to the physiological sensor being pressed against the subject too hard or too soft.

Figure 28:
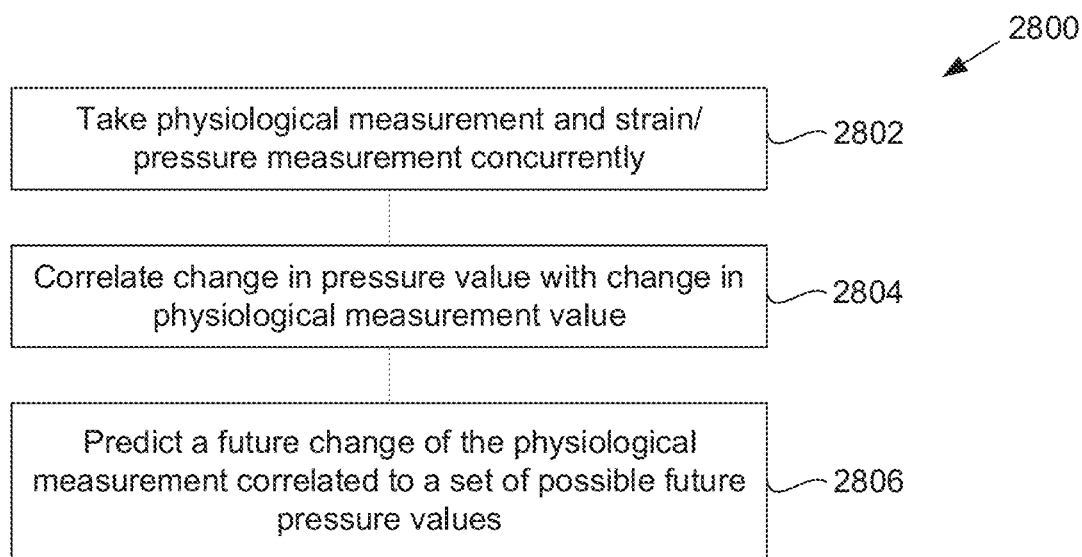
FIG. 28 illustrates a method of correlating a change in the pressure of the physiological sensor to a change in a physiological measurement value, according to an embodiment.

FIG. 28 illustrates a method 2800 of correlating a change in the pressure on the physiological sensor to a change in the physiological measurement value, according to an embodiment. Some of the features in FIG. 28 may be the same as or similar to some of the features in the other FIGS. described herein as noted by same and/or similar reference characters, unless expressly described otherwise. Additionally, reference may be made to features shown in any of the other FIGS. described herein and not shown in FIG. 28. Elements of the method 2800 may be executed in one or more ways such as by a human, including the subject, by a processing device such as the processing device 102, by mechanisms operating automatically or under human control such as the physiological sensor 206, and so forth.

The method 2800 may include taking a physiological measurement and a pressure measurement concurrently (2802). The method 2800 may include taking the physiological measurement and a strain measurement concurrently. For example, a processing device (e.g. the processing device 102) may be configured to record a pressure measurement value concurrently with a physiological measurement value. The processing device may include an internal clock. The processing device may store and/or execute instructions to take the physiological measurement according to a schedule. The processing device may store and/or execute instructions to take pressure measurements according to the same schedule as the physiological measurements. The processing device may store and/or execute instructions that trigger taking the pressure measurement within an amount of time before and/or after the physiological measurement is taken. The amount of time may be less than or equal to half the amount of time between successive physiological measurements. A pressure measurement taken within the amount of time of the physiological measurement may be considered taken "concurrently" with the physiological measurement although not taken at the same clock time as the physiological measurement.

The method 2800 may include correlating a change in the pressure measurement value from one or more of a set of previous pressure measurement values with a change in the physiological measurement value from one or more of a set of previous physiological measurement values (block 2804). For example, the processing device may store an algorithm for the physiological measurement as a function of the pressure measurement. The algorithm may be determined by a curve-fitting process that fits a curve to past physiological measurement data as a function of pressure measurement data. The algorithm may be determined by a regression analysis of the physiological measurement data and the pressure measurement data. The change in the pressure measurement value from a previous value to a current value may be input into the algorithm. The algorithm may output a change in the physiological measurement value as measured by the physiological sensor. The output physiological measurement value may, for example, be an amount of deviation of a measurement value from an actual value for the physiological characteristic. The measurement value may deviate from the actual value due to the change in pressure of the sensor against the subject. The change in the physiological measurement value may, therefore, be correlated to the change in the pressure measurement value.

The method 2800 may include predicting a future change between the physiological measurement value and one or more of a set of future physiological measurement values correlated to one or more of a set of possible future pressure measurement values (block 2806). For example, the prediction may be determined by the algorithm that correlates pressure measurement data to physiological measurement data. The prediction may be done as a function of time. For example, past pressure measurement values may vary cyclically such that changes in future pressure measurement values may be predicted according to the cyclic variation of past pressure measurement values. Deviations of future physiological measurement values from actual values may be predicted based on the cyclic variation of the pressure measurement values. Deviation data may be combined with cyclic variations in the actual values for the physiological characteristic such that the measured value may be predicted.

Figure 29:
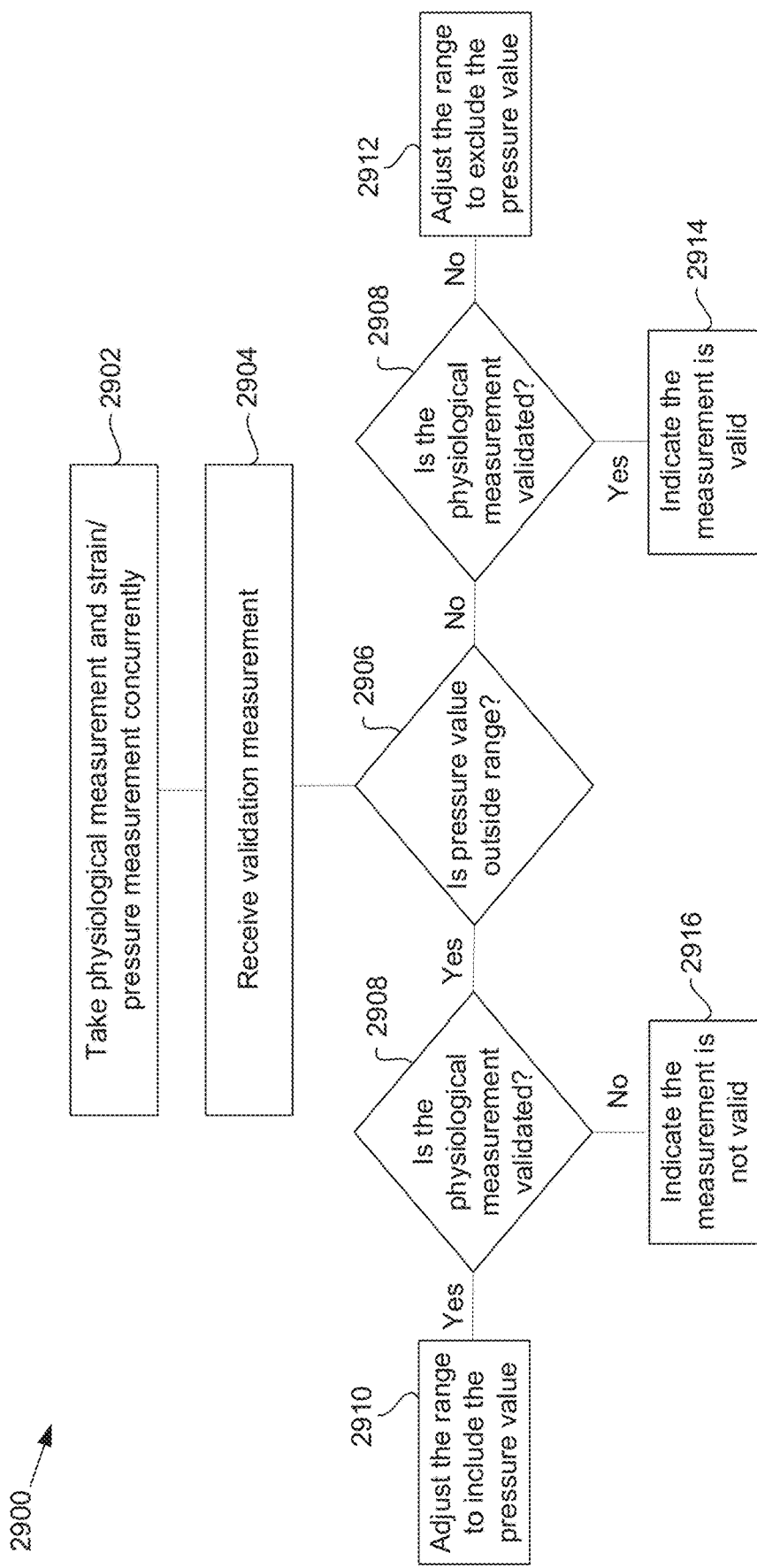
FIG. 29 illustrates a method of validating a physiological measurement, according to an embodiment.

FIG. 29 illustrates a method 2900 of validating a physiological measurement, according to an embodiment. Some of the features in FIG. 29 may be the same as or similar to some of the features in the other FIGS. described herein as noted by same and/or similar reference characters, unless expressly described otherwise. Additionally, reference may be made to features shown in any of the other FIGS. described herein and not shown in FIG. 29. Elements of the method 2900 may be executed in one or more ways such as by a human, including the subject, by a processing device such as the processing device 102, by mechanisms operating automatically or under human control such as the physiological sensor 206, and so forth.

The method 2900 may include taking a physiological measurement and a pressure measurement concurrently (block 2902). The method 2900 may include receiving a validation measurement of the physiological measurement (block 2904). The validation measurement may include a measurement of the same physiological characteristic taken by a separate measurement device concurrently or approximately concurrently with the physiological measurement. For example, the physiological measurement may be a non-invasive glucose measurement taken by the adjustable measurement device 300. The validation measurement may be an invasive glucose measurement taken by an invasive glucometer. The non-invasive glucose measurement and the invasive glucose measurement may be taken within an amount of time of each other. The amount of time may be a few seconds, a few minutes, three minutes, five minutes, ten minutes, and so forth.

The method 2900 may include determining whether the pressure and/or strain measurement value is within the optimal pressure and/or strain range (block 2906). The method 2900 may also include determining whether the validation measurement validates the physiological measurement value (block 2908). In response to the pressure and/or strain measurement value falling outside the optimal range and the physiological measurement being validated by the validation measurement, the method 2900 may include adjusting the optimal range of values to include the pressure and/or strain measurement value (block 2910). In response to the pressure and/or strain measurement value falling within the optimal range and the physiological measurement not being validated by the validation measurement, the method 2900 may include adjusting the optimal range of pressure values to exclude the pressure measurement value (block 2912).

The method 2900 may be executed to identify constituent pressures of the optimal range for the pressure and/or strain measurement values, including a maximum optimal pressure and/or a minimum optimal pressure. The physiological sensor may be pressed against the subject with a variety of pressures when the physiological sensor is optimally aligned with a physiological structure to be measured (e.g. the physiological structure 204). At each pressure level, the physiological measurement and the validation measurement may be taken. The validation measurement may be taken once and compared against a set of physiological measurements taken within a time frame of the validation measurement such as one minute, two minutes, five minutes, ten minutes, and so forth. The time frame may correspond to the physiological characteristic being measured. For example, the physiological characteristic may be the subject's resting heart rate. The heart rate may be measured twenty times at twenty different pressures over ten minutes. Validation of the heart rate may be taken every time the heart rate is measured by the measurement device or may be taken every minute. Validation of the subject's heart rate may be performed once during the ten minutes.

The method 2900 may include indicating the measurement is valid when the pressure value is outside the optimal range and the physiological measurement is validated (block 2914). The method 2900 may include indicating the measurement is not valid when the pressure value is outside the optimal range and the physiological measurement is not validated (block 2916).

Figure 30:
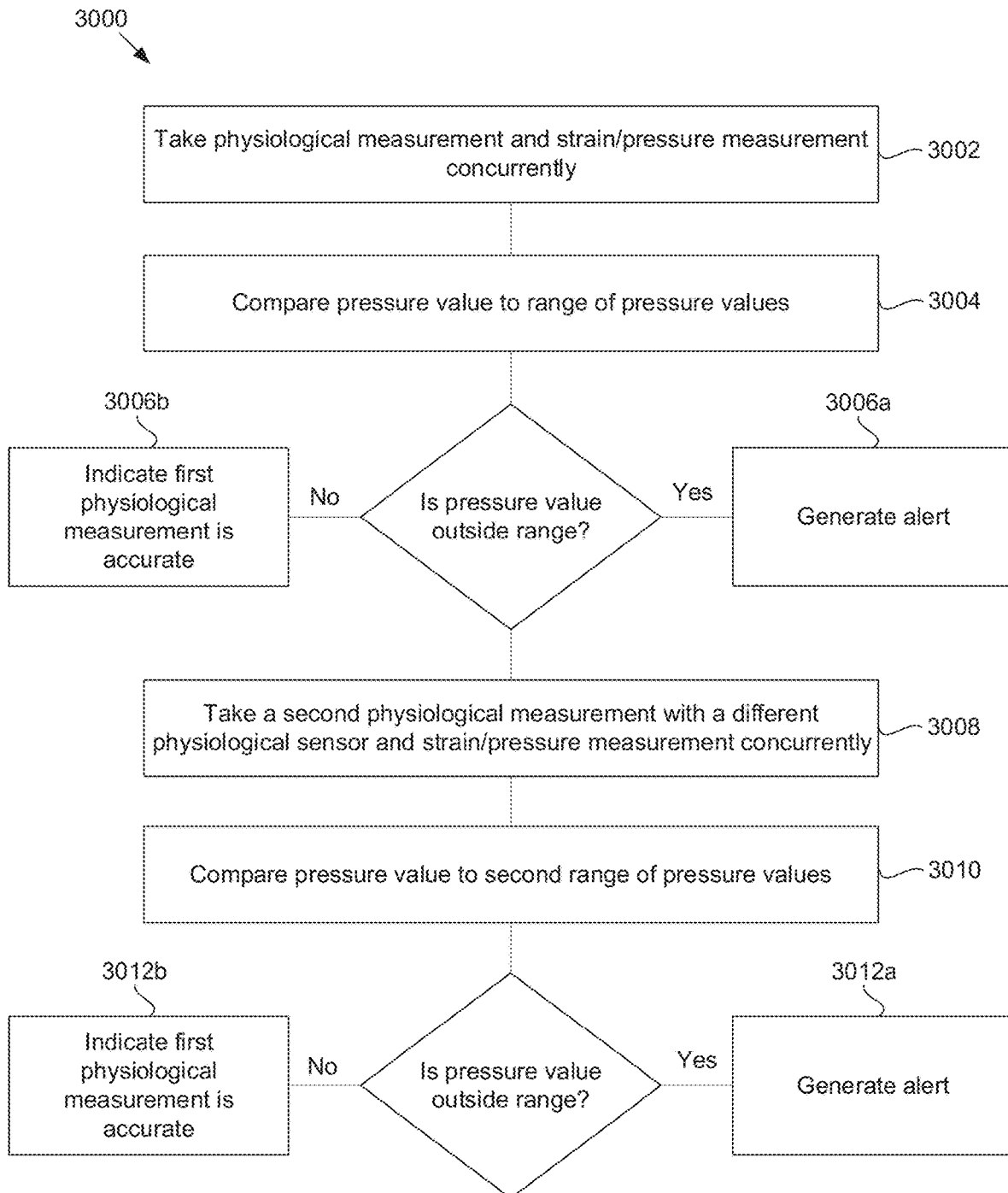
FIG. 30 illustrates a method of taking measurements with different physiological sensors that have different pressure ranges, according to an embodiment.

FIG. 30 illustrates a method 3000 of taking measurements with different physiological sensors that have different pressure ranges, according to an embodiment. Some of the features in FIG. 30 may be the same as or similar to some of the features in the other FIGS. described herein as noted by same and/or similar reference characters, unless expressly described otherwise. Additionally, reference may be made to features shown in any of the other FIGS. described herein and not shown in FIG. 30. Elements of the method 3000 may be executed in one or more ways such as by a human, including the subject, by a processing device such as the processing device 102, by mechanisms operating automatically or under human control such as the physiological sensor 206, and so forth.

The method 3000 may include taking a physiological measurement and a pressure measurement concurrently (block 3002). The method 3000 may include taking the physiological measurement and a strain measurement concurrently (block 3002). The physiological measurement may be taken by a first type of physiological sensor (e.g. the first sensor 112, the second sensor 114, and so forth). The method 3000 may include comparing the pressure and/or strain measurement value to a first range of optimal pressure and/or strain measurement values (block 3004). The first range may include pressure and/or strain values that correspond to the first type of sensor, e.g. that correspond to the amount of pressure that is optimal for the first type of physiological sensor against the subject. The method 3000 may include generating an alert when the pressure and/or strain measurement value is outside the first range (block 3006*a*). The alert may, for example, include notification content that notifies the subject the physiological measurement may be inaccurate. The method 3000 may include indicating the first physiological measurement is accurate when the pressure and/or strain measurement value is within the first range (block 3006*b*).

The method 3000 may include taking a second physiological measurement and a second pressure measurement (or a first pressure measurement if the previous measurement was a strain measurement) concurrently (block 3008). The method 3000 may include taking the second physiological measurement and a second strain measurement (or a first strain measurement if the previous measurement was a pressure measurement) concurrently (block 3008). The second physiological measurement may be taken by a second type of physiological sensor (e.g. if the first type is the first sensor 112, the second type would be the second sensor 114, and so forth). The method 3000 may include comparing the pressure and/or strain measurement value taken concurrently with the second physiological measurement to a second range of optimal pressure and/or strain measurement values (block 3010). The second range may be different than the first range. The second range may include pressure and/or strain values that correspond to the second type of sensor, e.g. that correspond to the amount of pressure that is optimal for the second type of physiological sensor against the subject. The method 3000 may include generating an alert when the pressure and/or strain measurement value measured concurrently with the second physiological measurement is outside the second range (block 3012*a*). The alert may, for example, include notification content that notifies the subject the physiological measurement may be inaccurate. The method 3000 may include indicating the second physiological measurement is accurate when the pressure and/or strain measurement value measured concurrently with the second physiological measurement is within the second range (block 3012*b*).

A measurement device such as the adjustable measurement device 300 may include the two different types of physiological sensors. The first type may have an optimal pressure and/or strain range that is different than an optimal pressure and/or strain range for the second type of physiological sensor. The two optimal ranges may overlap or may be non-overlapping. The processing device may be configured to notify the subject to adjust the pressure of the measurement device against the subject according to which type of physiological sensor is going to take the next physiological measurement. The processing device may be configured to notify the subject to adjust the pressure when the optimal ranges do not overlap. The processing device may be configured to notify the subject when the current pressure of the measurement device on the subject is outside the overlap between the two optimal ranges.

A first range of pressure and/or sensor measurement values may be an overlap between a first subrange and a second subrange. The first subrange may correspond to the first type of physiological sensor and the second subrange may correspond to the second type of physiological sensor. A maximum pressure and/or strain measurement value for the first range may fall within the first subrange. A minimum pressure and/or strain measurement value for the first range may fall within the second subrange.

Figure 31A:
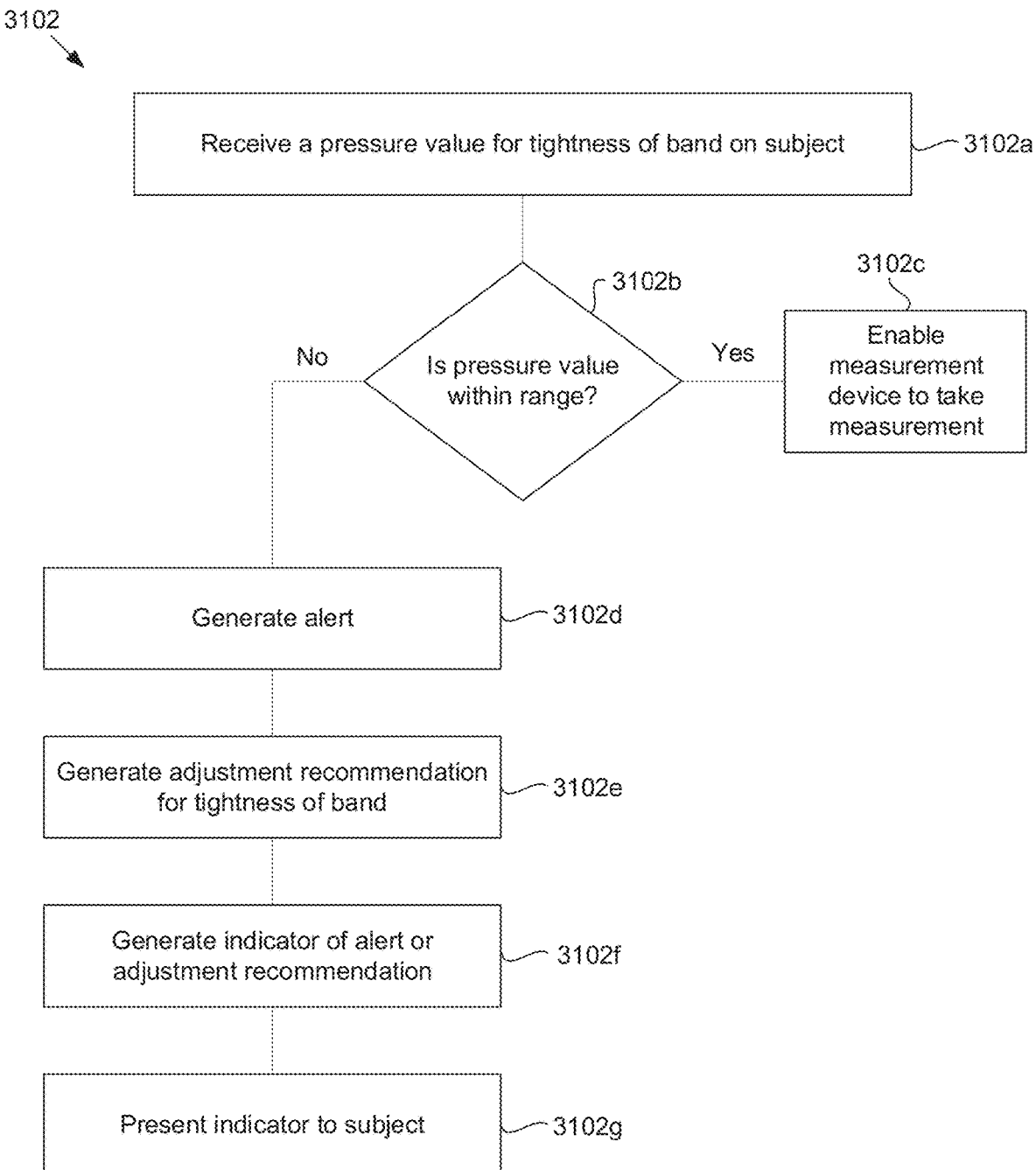
FIG. 31A illustrates a method of enabling the physiological sensor to take a measurement when it is pressed against the subject at a correct pressure within a range of correct pressures, according to an embodiment.

FIG. 31A illustrates a method 3102 of enabling the physiological sensor to take a measurement when it is pressed against the subject at a correct pressure within a range of pressures, according to an embodiment. Some of the features in FIG. 31A may be the same as or similar to some of the features in the other FIGS. described herein as noted by same and/or similar reference characters, unless expressly described otherwise. Additionally, reference may be made to features shown in any of the other FIGS. described herein and not shown in FIG. 31A. Elements of the method 3102 may be executed in one or more ways such as by a human, including the subject, by a processing device such as the processing device 102, by mechanisms operating automatically or under human control such as the physiological sensor 206, and so forth.

The method 3102 may include receiving a pressure measurement value of the tightness of a wearable device on a subject (block 3102a). The pressure measurement value may be a measure of the strain in the band of the wearable device (e.g. the band 106 of the wearable device 100). The pressure measurement value may be a pressure measurement by a pressure sensor (e.g. the pressure sensor 400). For example, the pressure measurement value may be determined by a processing device (e.g. the processing device 102) based on an electronic signal indicating a capacitance of the pressure sensor. The method 3102 may include determining whether the pressure measurement value falls within an optimal range of pressure values ranging from a minimum optimal pressure value to a maximum optimal pressure value (block 3102b). The method 3102 may include enabling a measurement device to take a physiological measurement from the subject without distorting the physiological measurement (block 3102c). The measurement device may be enabled to take an undistorted physiological measurement when the pressure measurement value falls within the optimal range. For example, the processing device (e.g. the processing device 102) may be programmed to take the physiological measurement by the measurement device (e.g. the adjustable measurement device 300) at times when the adjustable measurement device 300 is pressed against the subject at a pressure in the optimal range.

The method 3102 may include generating an alert when the pressure measurement value is outside the optimal range of pressure values (block 3102d). The method 3102 may include generating an adjustment recommendation that recommends an adjustment to the tightness of the wearable device on the subject (block 3102e). For example, the processing device may be programmed to calculate how far outside the optimal range the current pressure is and/or whether the current pressure is above or below the optimal range. The processing device may be programmed to recommend tightening or loosening the band of the wearable device. The method 3102 may include generating an indicator of the alert or the adjustment recommendation (block 3102f). The processing device may be configured to generate the indicator or to communicate the alert and/or the recommendation to a user device such as the user device 118. The method 3102 may include presenting the indicator to the subject (block 3102g).

Figure 31B:
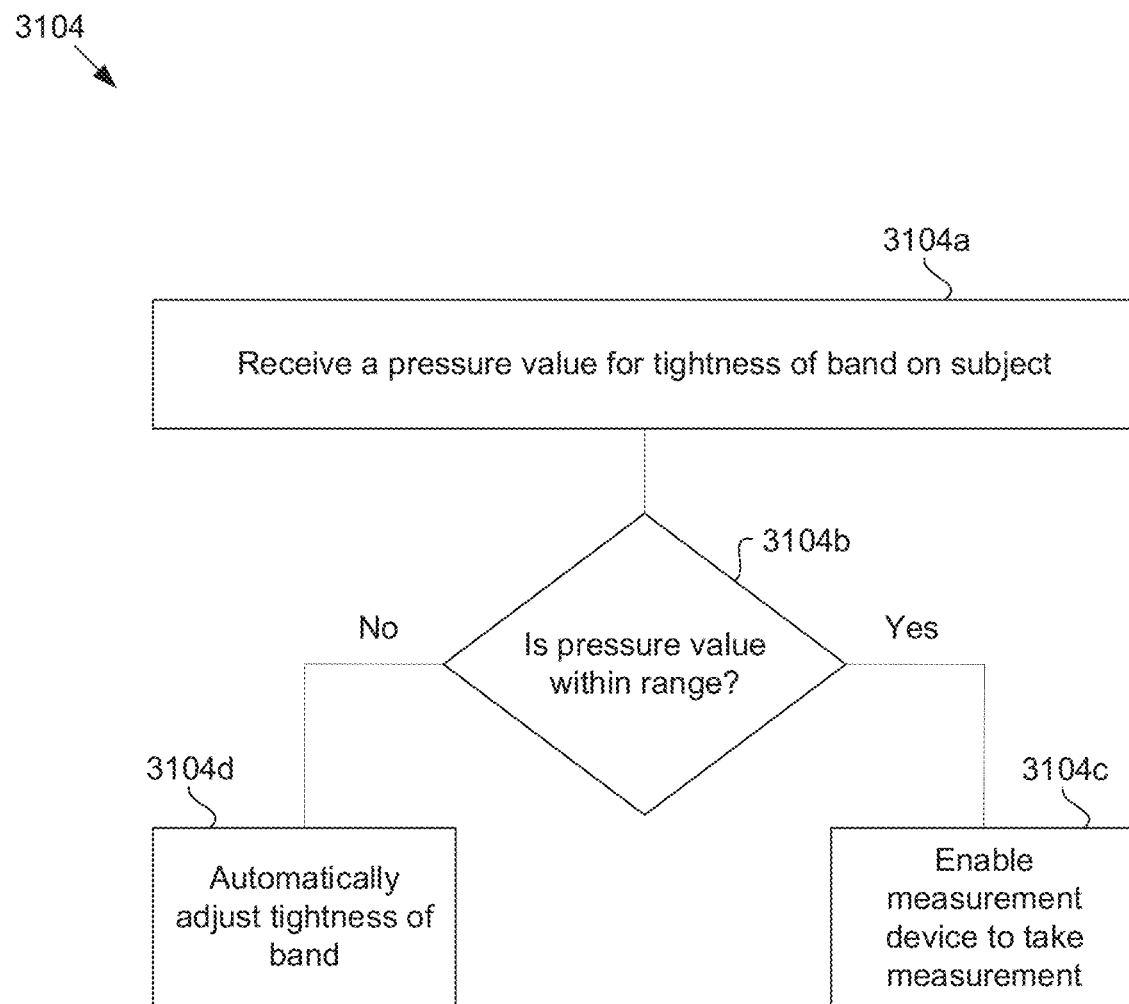
FIG. 31B illustrates a method of automatically adjusting a tightness of the wearable band, according to an embodiment.

FIG. 31B illustrates a method 3104 of automatically adjusting a tightness of the wearable band, according to an embodiment. Some of the features in FIG. 31B may be the same as or similar to some of the features in the other FIGS. described herein as noted by same and/or similar reference characters, unless expressly described otherwise. Additionally, reference may be made to features shown in any of the other FIGS. described herein and not shown in FIG. 31B. Elements of the method 3104 may be executed in one or more ways such as by a human, including the subject, by a processing device such as the processing device 102, by mechanisms operating automatically or under human control such as the physiological sensor 206, and so forth.

The method 3104 may include receiving a pressure measurement value of the tightness of a wearable device on a subject (block 3104a). The method 3104 may include determining whether the pressure measurement value falls within an optimal range of pressure values ranging from a minimum optimal pressure value to a maximum optimal pressure value (block 3104b). The method 3104 may include enabling a measurement device to take a physiological measurement from the subject without distorting the physiological measurement (block 3104c).

The method 3104 may include automatically adjusting the tightness of the wearable device on the subject (block 3104d). The tightness may be automatically adjusted by an electromechanical device (e.g. the motorized band tightening mechanism 510). The tightness may be increased when the pressure of the measurement device against the subject is below the optimal range. The tightness may be decreased automatically when the pressure of the measurement device against the subject is above the optimal range. For example, a processing device (e.g. the processing device 102) may be coupled to a pressure sensor (e.g. the pressure sensor 400) and an electromechanical tightening mechanism (e.g. the motorized band tightening mechanism 510). The processing device may be programmed to activate the electromechanical device upon a trigger event. The trigger event may be the pressure sensor measuring a pressure outside the optimal range.

The wearable device may include a second measurement device that corresponds to a second range of pressure values (e.g. the adjustable measurement device 300 may include the first sensor 112 and the second sensor 114). The optimal range of pressure values for the first measurement device may be different from the optimal range of pressure values for the second measurement device. The tightness of the wearable device may be automatically adjusted to fall within the optimal range for the first measurement device in response to the first measurement device taking a measurement. The tightness of the wearable device may be automatically adjusted to fall within the optimal range of the second measurement device in response to the second measurement device taking a measurement. For example, measurements by the first and second measurement devices may be scheduled, and the processing device may be triggered to activate the electromechanical tightening mechanism according to the schedule of measurements.

Figure 32:
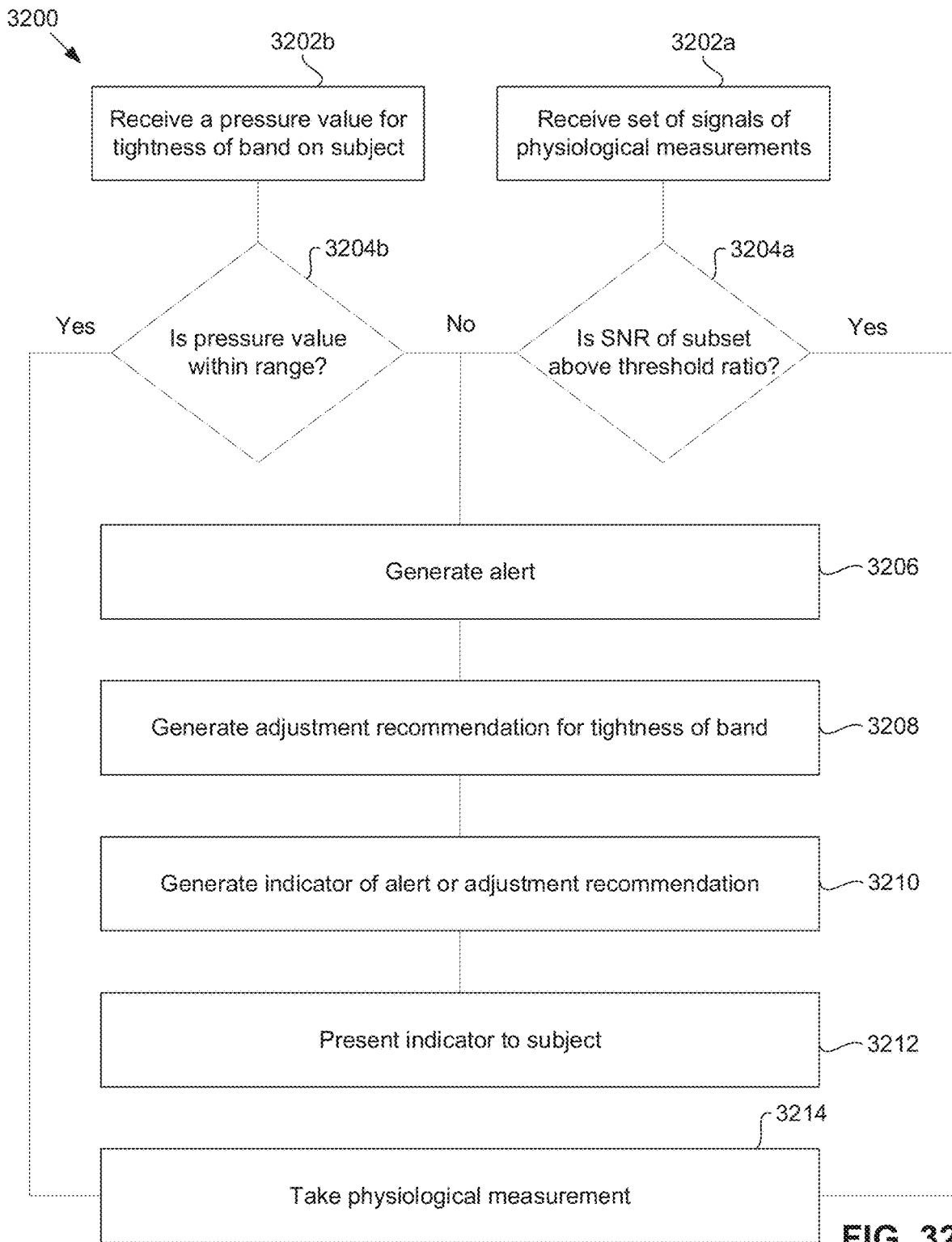
FIG. 32 illustrates a method of determining an adjustment for the pressure of the measurement device and/or the physiological sensor against a subject, according to an embodiment.

FIG. 32 illustrates a method 3200 of determining an adjustment for a pressure of a measurement device and/or physiological sensor against a subject, according to an embodiment. Some of the features in FIG. 32 may be the same as or similar to some of the features in the other FIGS. described herein as noted by same and/or similar reference characters, unless expressly described otherwise. Additionally, reference may be made to features shown in any of the other FIGS. described herein and not shown in FIG. 32.

Elements of the method 3200 may be executed in one or more ways such as by a human, including the subject, by a processing device such as the processing device 102, by mechanisms operating automatically or under human control such as the physiological sensor 206, and so forth.

The method 3200 may include receiving a signal or a set of signals corresponding to a set of physiological measurements taken by a measurement device (e.g. by the physiological sensor 206 of the adjustable measurement device 300) (block 3202a). The method 3200 may include receiving a pressure value for the tightness of the wearable device (e.g. of the band 106 of the wearable device 100) on the subject (block 3202b). The method 3200 may include determining whether an SNR for the signal or SNRs for at least a subset of the set of signals (e.g. at least one SNR of at least one signal) is above a threshold SNR (block 3204a). The method 3200 may include determining, generally, whether the signal quality for the signal or a subset of the set of signals is above a threshold signal quality. For example, the subject may select, via a user interface (e.g. the user interface 104) a type of physiological characteristic for the measurement device to measure. The processing device may be programmed with a signal processing algorithm. The processing device may apply the algorithm to the signals received from the measurement device to determine the SNRs. The method 3200 may include determining whether the pressure value is within the optimal range (block 3204b).

The method 3200 may include a response to the pressure value being out-of-range and/or the SNR being below the threshold SNR. The method 3200 may include generating an alert when the pressure measurement value is outside the optimal range of pressure values and/or when the SNR is below the threshold SNR (block 3206). The method 3200 may include generating an adjustment recommendation that recommends an adjustment to the tightness of the wearable device on the subject (block 3208). For example, the set of signals from the measurement device may be from consecutive measurements taken during a length of time. In response to the set of consecutive signals or a subset of consecutive signals having SNRs or an average SNR below the threshold SNR, the processing device may generate the alert and/or the adjustment recommendation. The alert and/or the adjustment recommendation based on the pressure measurement value relative to the optimal range. For example, if the SNR is below the threshold SNR and the pressure measurement value is outside the optimal range, the processing device may recommend adjusting the tightness of the band. If the SNR is below the threshold SNR and the pressure measurement value is within the optimal range, the processing device may recommend moving the measurement device into better alignment with the physiological structure being measured. The method 3200 may include generating an indicator of the alert or the adjustment recommendation (block 3210). The processing device may be configured to generate the indicator or to communicate the alert and/or the recommendation to a user device such as the user device 118. The method 3200 may include presenting the indicator to the subject (block 3212).

The SNR and/or other signal qualities may be improved by the measurement device being pressed against the subject within the optimal pressure range. The SNR and/or other signal qualities may be improved by aligning the measurement device as closely as possible with the physiological structure the measurement device is to measure. The method 3200 may be executed to enable optimization of the SNR. The method 3200 may be executed to enable optimization of another signal quality such as amplitude.

The method 3200 may include taking a physiological measurement when the pressure value is within the optimal pressure range and/or when the SNR of the subset is above the threshold ratio (block 3214).

Figure 33:
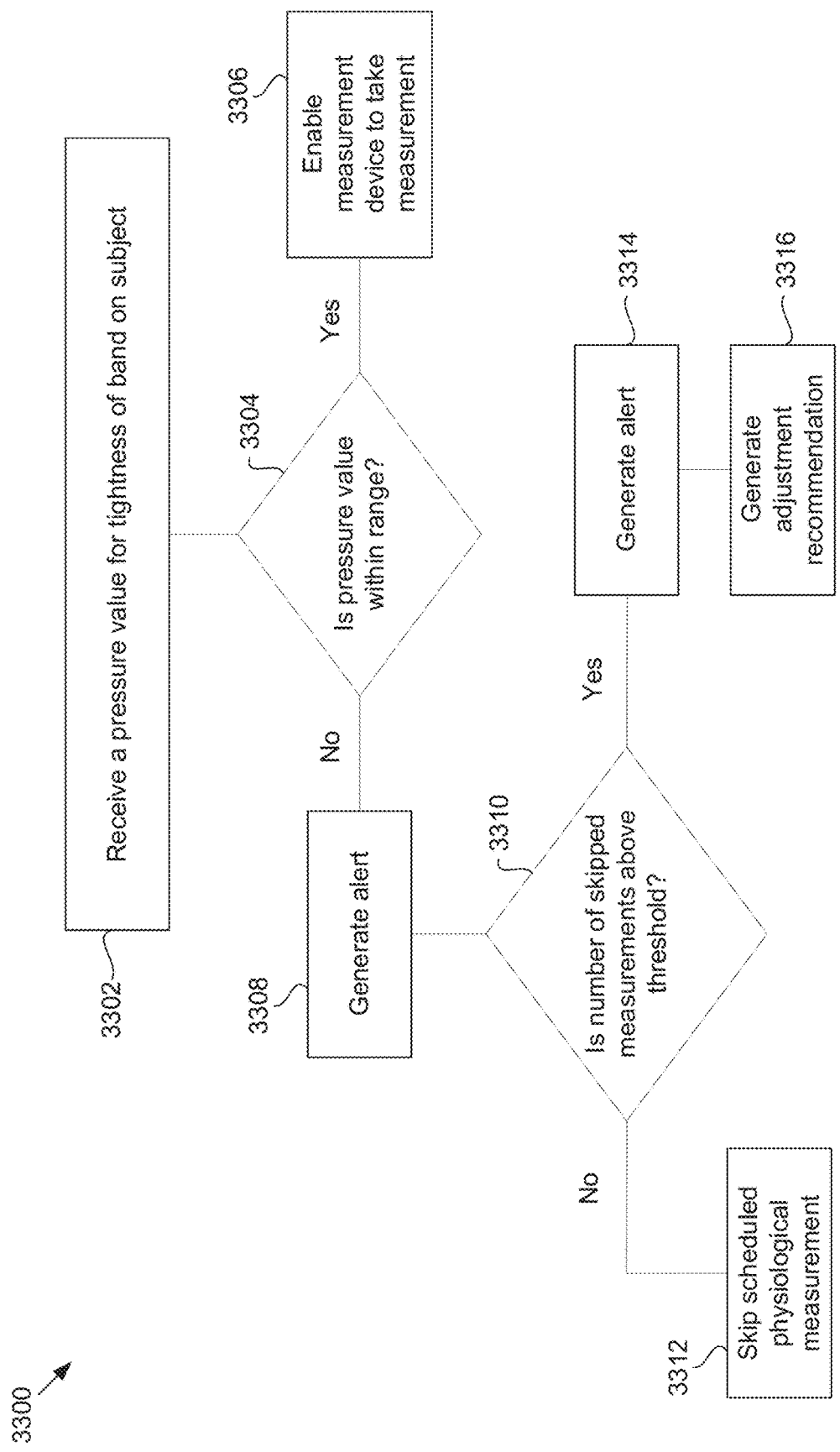
FIG. 33 illustrates a method of skipping physiological measurements when the physiological sensor is not pressed against the subject in the correct pressure range, according to an embodiment.

FIG. 33 illustrates a method 3300 of skipping physiological measurements when the physiological sensor is not pressed against the subject in the correct pressure range, according to an embodiment. Some of the features in FIG. 33 may be the same as or similar to some of the features in the other FIGS. described herein as noted by same and/or similar reference characters, unless expressly described otherwise. Additionally, reference may be made to features shown in any of the other FIGS. described herein and not shown in FIG. 33. Elements of the method 3300 may be executed in one or more ways such as by a human, including the subject, by a processing device such as the processing device 102, by mechanisms operating automatically or under human control such as the physiological sensor 206, and so forth.

The method 3300 may include receiving a pressure measurement value of the tightness of a wearable device on a subject (block 3302). The method 3300 may include determining whether the pressure measurement value falls within an optimal range of pressure values (block 3304). The method 3300 may include enabling a measurement device to take a physiological measurement from the subject when the pressure measurement value is within the optimal range (block 3306). The method 3300 may include generating an alert when the pressure measurement value is outside the optimal range of pressure values (block 3308).

If the pressure measurement value is outside the optimal range, a scheduled measurement by the measurement device may be skipped. For example, the processing device may be programmed with a default schedule by which to take physiological measurements by the measurement device (e.g. the processing device 102 and the physiological sensor 206 on the adjustable measurement device 300). The default setting of the processing device may be to trigger the physiological sensor to take the measurement on schedule. The processing device may be programmed to, in response to receiving a pressure measurement value outside the optimal range, skip the next scheduled physiological measurement, such as by not triggering the physiological sensor to take the measurement.

The method 3300 may include determining whether the number of skipped measurements is above a threshold number (block 3310). For example, the processing device may keep a running tally of the number of skipped physiological measurements previous to the next scheduled physiological measurement. The processing device may store the number skipped within a certain time frame before the next scheduled physiological measurement. The processing device may store the number of consecutively skipped physiological measurements before the next scheduled physiological measurement. The tally may only include the most recent "streak" of consecutive skipped physiological measurements. The method 3300 may include skipping the next scheduled physiological measurement if the number of skipped measurements is below the threshold number for skipped measurements (block 3312).

The method 3300 may include generating an alert in response to the threshold number or more of physiological measurements being skipped (block 3314). The alert may indicate the number of skipped measurements meets and/or exceeds the threshold. The threshold may be programmed into the processing device by a manufacturer of the measurement device. The threshold may be programmed into the processing device by the subject, such as via a user interface. The threshold may be time-dependent such that one skipped measurement for a type of measurement that is taken once a day generates an alert. 100 skipped measurements for a type of measurement that is taken continuously or multiple times per minute may trigger the alert to generated. The alert may indicate generally that measurements are being skipped without indicating how many have been skipped. The alert may indicate how many measurements have been skipped. The method 3300 may include generating an adjustment recommendation (block 3316). The adjustment recommendation may be an adjustment of the tightness of the band on the subject. The adjustment recommendation may be an adjustment of the pressure of the measurement device against the subject. The adjustment recommendation may be an adjustment of the position of the measurement device on the subject.

Figure 34:
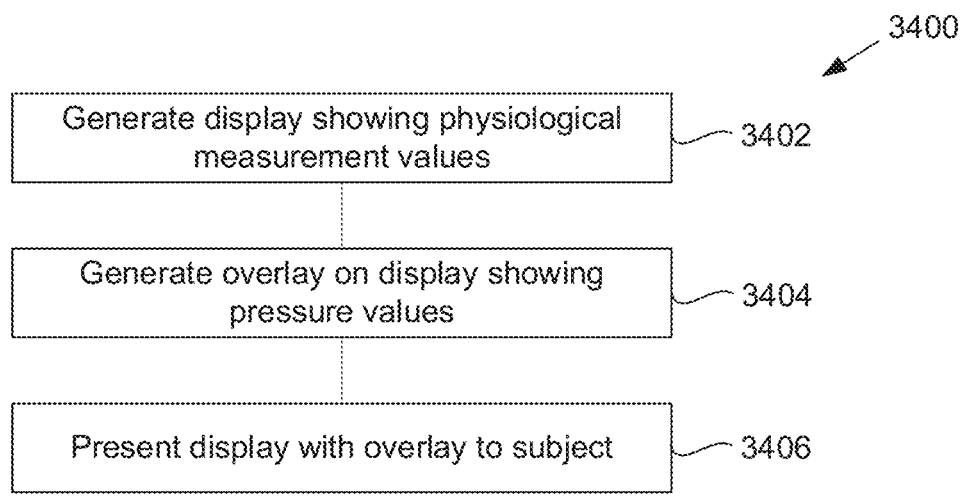
FIG. 34 illustrates a method of generating a graphical display of physiological measurements and pressure values, according to an embodiment.

FIG. 34 illustrates a method 3400 of generating a graphical display of physiological measurements and pressure values, according to an embodiment. Some of the features in FIG. 34 may be the same as or similar to some of the features in the other FIGS. described herein as noted by same and/or similar reference characters, unless expressly described otherwise. Additionally, reference may be made to features shown in any of the other FIGS. described herein and not shown in FIG. 34. Elements of the method 3400 may be executed in one or more ways such as by a human, including the subject, by a processing device such as the processing device 102, by mechanisms operating automatically or under human control such as the physiological sensor 206, and so forth.

The method 3400 may include generating a graphical display showing a set of physiological measurement values taken over a length of time (block 3402). The graphical display may, for example, include data points distributed on a grid with a time axis and a measurement value axis. The units of time and/or the measurement values may be shown or may not be shown. Gridlines may be shown or may not be shown. A curve may connect the data points. Each data point may have a measurement value coordinate that corresponds to a time coordinate. The method 3400 may include generating an overlay on the graphical display showing a set of pressure measurement values taken over the length of time (block 3404). The overlay may have a different visual feature from the curve and/or data points of the physiological measurement. For example, physiological measurements may be indicated by a first color and pressure measurements may be indicated by a second color. The method 3400 may include presenting the graphical display with the overlay to the subject (block 3406). The overlay may enable the subject to visually correlate the pressure of the physiological sensor against the subject with specific physiological measurements to visually identify which measurements may be inaccurate. Without the overlay, the subject may be unaware of whether a specific physiological measurement is accurate.

The overlay may show a set of pressure measurement values relative to the optimal range for the physiological sensor that generates the physiological measurements. A subset of pressure measurement values may be shown on the graphical display by a first visual cue that indicates the subset of pressure measurement values is outside the range of pressure values. A subset of physiological measurement values may be shown on the graphical display by a second visual cue that indicates the subset of physiological measurement values corresponds to the subset of pressure measurement values that is outside the optimal range.

Figure 35:
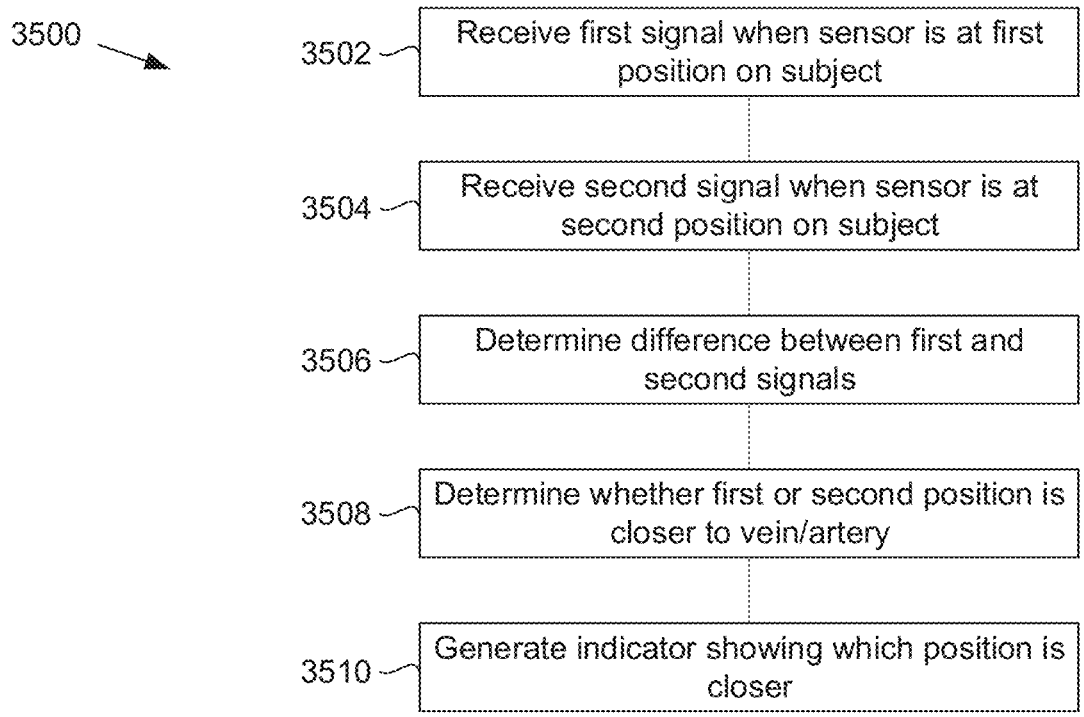
FIG. 35 illustrates a method of determining a relative position of the physiological sensor to the physiological structure of the subject, according to an embodiment.

FIG. 35 illustrates a method 3500 of determining a relative position of a physiological sensor to a physiological structure of a subject, according to an embodiment. Some of the features in FIG. 35 may be the same as or similar to some of the features in the other FIGS. described herein as noted by same and/or similar reference characters, unless expressly described otherwise. Additionally, reference may be made to features shown in any of the other FIGS. described herein and not shown in FIG. 35. Elements of the method 3500 may be executed in one or more ways such as by a human, including the subject, by a processing device such as the processing device 102, by mechanisms operating automatically or under human control such as the physiological sensor 206, and so forth.

The method 3500 may include receiving a first signal from the physiological sensor when the physiological sensor is at a first position on the subject (block 3502). The first position may have an unknown position relative to the physiological subject to be interrogated by the physiological sensor. The first position may have a relative position that is approximately known relative to the physiological sensor. For example, the physiological structure may include a vein and/or artery. A general area of the vein and/or artery may be known, but a precise position may be unknown. The method 3500 may include adjusting the physiological sensor to a second position and receiving a second signal from the physiological sensor when the physiological sensor is at the second position on the subject (block 3504). The second position may have an unknown position relative to the physiological structure. The second position may have an approximately known position relative to the physiological structure.

The method 3500 may include determining a difference between the first signal and the second signal (block 3506). The difference may be calculated based on one or more signal qualities. For example, the difference may be calculated based on a first SNR of the first signal and a second SNR of the second signal. The difference may be calculated based on a first amplitude of the first signal and a second amplitude of the second signal. The difference may be calculated based on a combination of the first SNR and the first amplitude and a combination of the second SNR and the second amplitude. The method 3500 may include determining whether the first position or the second position is closer to the physiological structure (block 3508). For example, the physiological sensor may yield a higher SNR and/or signal amplitude at the first position than at the second position. This may be because the first position is closer to the physiological structure than the second position. This may be because there is less interference from other physiological structures and/or other physiological phenomena at the first position than at the second position, even if the second position is spatially closer to the physiological structure. The method 3500 may include, once it is determined whether the first position or the second position is closer, generating an indicator showing which position is closer and presenting the indicator to the subject (block 3510).

The subject may wear a smartwatch with a band (e.g. the band 106), a smartwatch face (e.g. the user interface 104), and a measurement device attached to the band (e.g. the adjustable measurement device 300). The subject may slide the measurement device on the band to approximately align the physiological sensor in the measurement device (e.g. the first sensor 112, the second sensor 114, and so forth) with a radial artery in the subject's wrist. The subject may press a graphically-displayed button on the touch screen of the smartwatch face and the processor in the smartwatch (e.g.

the processing device 102) may communicate with the physiological sensor, triggering a measurement by the physiological sensor. The measurement may be communicated to the processor and the processor may generate a prompt, displayed to the subject on the smartwatch face, to adjust the position of the measurement device. The subject may adjust the position of the measurement device and then press a graphical button on the touch screen indicating the measurement device has been moved. The processor may trigger another measurement. The processor may compare the SNR and/or the signal shape of the first measurement to the SNR and/or the signal shape of the second measurement. The processor may determine the second position is closer and may generate a prompt, displayed to the subject via the touchscreen, that the measurement device is aligned or to continue moving the measurement device in the same direction on the band and relative to the radial artery.

Figure 36:
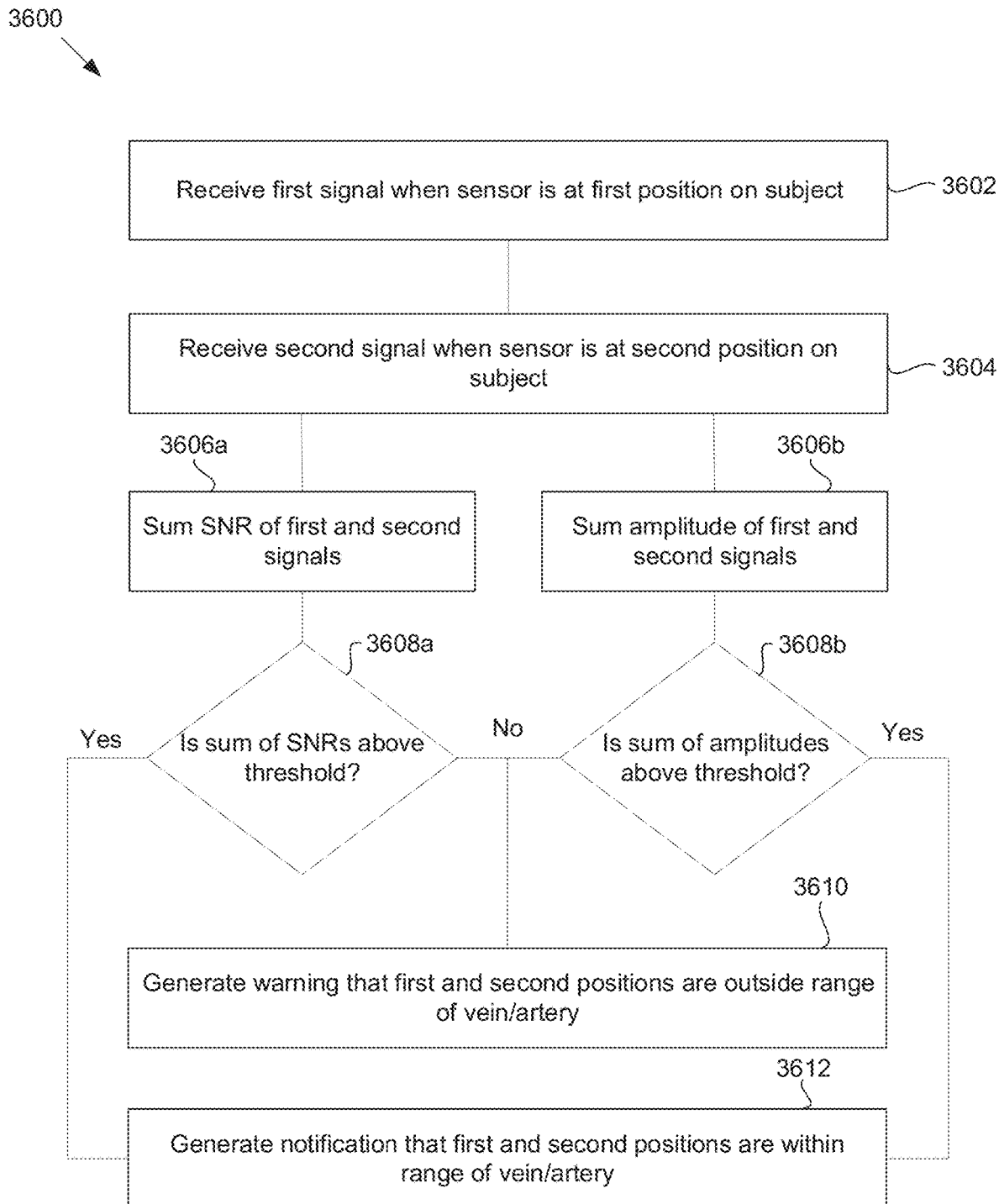
FIG. 36 illustrates a method of using various signal characteristics to determine a relative position of the physiological structure in the subject's body, according to an embodiment.

FIG. 36 illustrates a method 3600 of using various signal characteristics to determine the relative position of a physiological structure in the subject's body, according to an embodiment. Some of the features in FIG. 36 may be the same as or similar to some of the features in the other FIGS. described herein as noted by same and/or similar reference characters, unless expressly described otherwise. Additionally, reference may be made to features shown in any of the other FIGS. described herein and not shown in FIG. 36. Elements of the method 3600 may be executed in one or more ways such as by a human, including the subject, by a processing device such as the processing device 102, by mechanisms operating automatically or under human control such as the physiological sensor 206, and so forth.

The method 3600 may include receiving a first signal from a physiological sensor at a first position on the subject (block 3602). The method 3600 may include receiving a second signal from the physiological sensor at a second position on the subject (block 3604). The second signal may be received from a second physiological sensor integrated into the measurement device at a different position relative to the first physiological sensor. The first signal may be generated at the same time as the second signal. The measurement device may remain stationary on the subject as the first signal is generated by the first physiological sensor and the second signal is generated by the second physiological sensor. The first signal may be generated at a first time and the second signal may be generated at a second time after the first time. The position of the measurement device may be adjusted on the subject between the first time and the second time or the measurement device may remain stationary on the subject between the first time and the second time.

The method 3600 may include determining a sum of the SNR of the first signal (i.e. a first SNR) and the SNR of the second signal (i.e. a second SNR) (block 3606a). The method 3600 may include determining a sum of the amplitude of the first signal (i.e. a first amplitude) and the amplitude of the second signal (i.e. a second amplitude) (block 3606b). The method 3600 may include determining whether the sum of the first SNR and the second SNR meets a threshold SNR level (block 3608a). The method 3600 may include determining whether the sum of the first amplitude and the second amplitude meets a threshold amplitude level (block 3608b). The method 3600 may include, in response to the sum of the SNRs and/or the sum of the amplitudes being less than the respective thresholds, generating a warning that the first and second positions are outside a range of a physiological structure to be interrogated by the measurement device (e.g. a vein and/or artery of the subject) (block 3610).

Perfect alignment of the physiological sensor with the physiological structure may not be necessary to obtain a useful signal (e.g. a signal from which a measurement value can be obtained). For example, the measurement device may include two physiological sensors at different positions in the measurement device (see, e.g., FIGS. 1A and/or 13A-B). The two physiological sensors may be of different types from each other, e.g. the first sensor 112 and the second sensor 114. The two physiological sensors may be employed simultaneously to measure the same physiological characteristic of the subject. For example, the two different physiological sensors may be used to measure the subject's glucose levels. Because of the shape of the subject's vein and/or artery, it may be impossible to perfectly align both sensors with the vein and/or artery. For example, the subject's artery may be curved such that one physiological sensor can be aligned over the artery and the other physiological sensor is positioned to a side of the artery. The signal quality of the first physiological sensor may meet a threshold for an individual sensor and the signal quality of the second physiological sensor may not meet the threshold. However, the processing device may be programmed to use the first signal to clean up the second signal, e.g. by removing noise using a bandpass filter set according to the first signal. A minimum total signal quality of both signals together, e.g. the threshold SNR level or the threshold amplitude level, may allow the processing device to clean up one signal based on the other. Thus, summing the signal qualities may indicate whether the relative positions of both sensors are close enough to the physiological structure to enable accurate measurement by both sensors.

The subject may not know a relative position of the physiological structure or may only know approximately where the physiological structure is but may not know precisely enough to precisely position the measurement device in alignment with the physiological structure. Positioning the measurement device, taking a measurement, repositioning, taking a second measurement, and summing the signal qualities may allow the subject to determine if the measurement device is within a range of the physiological structure to begin a guided alignment process. If the sum is below the threshold level, the measurements may be too noisy to tell the subject a direction to move the measurement device to be in better alignment. If the sum is above the threshold level, the processing device may automatically generate an indicator of which direction the subject should mover the physiological sensor based on which signal has a higher quality.

The method 3600 may include generating a notification that the first position and/or the second position are within range of the vein and/or artery when the sum of the SNR is above the threshold and/or when the sum of the amplitudes is above the threshold (block 3612).

Figure 37:
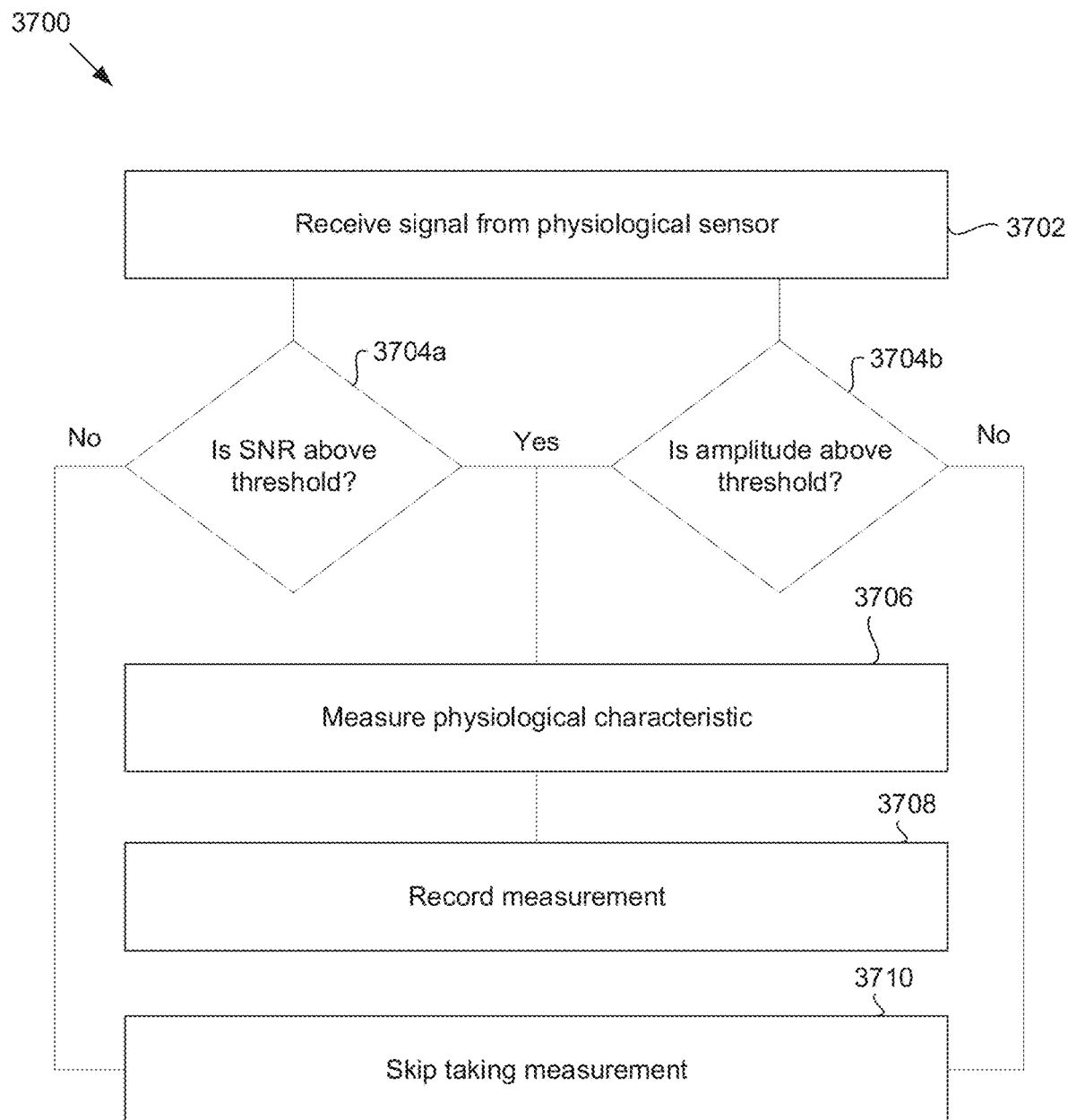
FIG. 37 illustrates a method of recording a measurement of a physiological characteristic, according to an embodiment.

FIG. 37 illustrates a method 3700 of measuring a physiological characteristic, according to an embodiment. Some of the features in FIG. 37 may be the same as or similar to some of the features in the other FIGS. described herein as noted by same and/or similar reference characters, unless expressly described otherwise. Additionally, reference may be made to features shown in any of the other FIGS. described herein and not shown in FIG. 37. Elements of the method 3700 may be executed in one or more ways such as by a human, including the subject, by a processing device such as the processing device 102, by mechanisms operating automatically or under human control such as the physiological sensor 206, and so forth.

The method 3700 may include receiving a signal from a physiological sensor (block 3702). The method 3700 may include determining whether a quality of the signal meets a minimum threshold, such as an SNR of the signal (block 3704a) and/or an amplitude of the signal (block 3704b). The method 3700 may include, in response to the signal quality meeting and/or exceeding the minimum threshold, measuring a physiological characteristic of the subject (block 3706). The method 3700 may include recording the measurement, recording a value associated with the measurement, recording other data regarding the measurement, and/or presenting data regarding the measurement to the subject (block 3708). For example, the time of the measurement and the value associated with the measurement may be sent to a remote database and stored in the database. The value associated with the measurement may be presented to the subject via a user device and/or a user interface integrated into the measurement device. The method may include skipping taking the measurement when the signal quality does not meet the minimum threshold and/or when the amplitude is below the threshold (block 3710).

Figure 38:
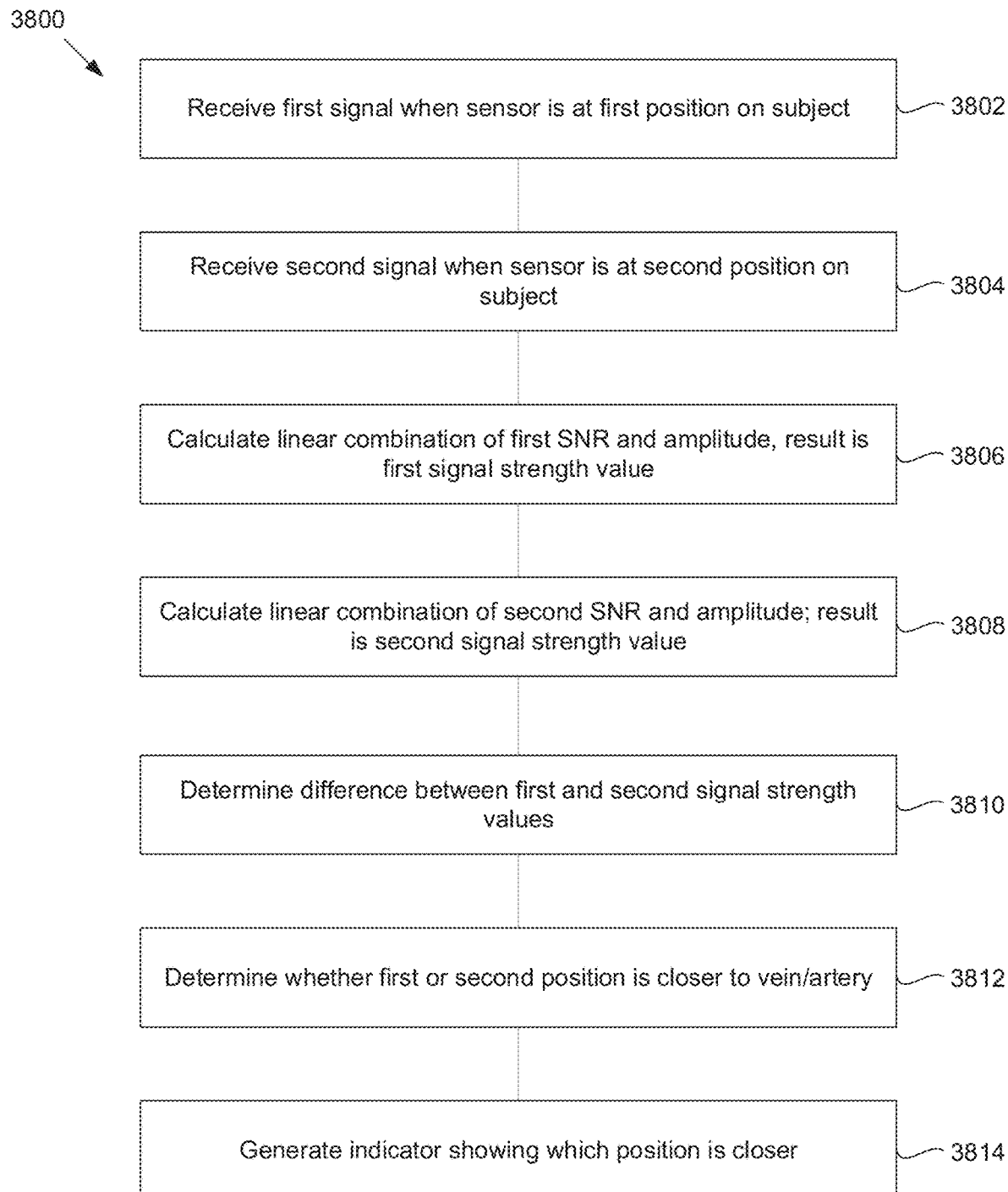
FIG. 38 illustrates a method of determining a relative position of the physiological structure of the subject using a signal strength value, according to an embodiment.

FIG. 38 illustrates a method 3800 of determining a relative position of a physiological structure of the subject using a signal strength value, according to an embodiment. Some of the features in FIG. 38 may be the same as or similar to some of the features in the other FIGS. described herein as noted by same and/or similar reference characters, unless expressly described otherwise. Additionally, reference may be made to features shown in any of the other FIGS. described herein and not shown in FIG. 38. Elements of the method 3800 may be executed in one or more ways such as by a human, including the subject, by a processing device such as the processing device 102, by mechanisms operating automatically or under human control such as the physiological sensor 206, and so forth.

The method 3800 may include receiving a first signal from a physiological sensor when the physiological sensor is at a first position on the subject (block 3802). The method 3800 may include receiving a second signal from the physiological sensor or a second physiological sensor when the physiological sensor or the second physiological sensor is at a second position on the subject (block 3804). The second position may be different than the first. The first and second physiological sensors may be the same type (e.g. both are instances of the first sensor 112) or the first and second physiological sensors may be different types (e.g. one is the first sensor 112 and one is the second sensor 114).

The method 3800 may include calculating a first signal strength value (block 3806). The first signal strength value may correspond to the first signal. The first signal strength value may be, for example, a linear combination of an SNR of the first signal and an amplitude of the first signal. The method 3800 may include calculating a second signal strength value (block 3808). The second signal strength value may correspond to the second signal. The second signal strength value may be, for example, a linear combination of an SNR of the second signal and an amplitude of the second signal. The method 3800 may include determining a difference between the first signal strength value and the second signal strength value (block 3810). For example, the first and second signal strength values may have the same units and the difference may be determined by subtracting the second signal strength value from the first signal strength value. The method 3800 may include determining whether the first position or the second position is closer to the physiological structure (block 3812). For example, if the difference is negative, the difference may indicate the second signal is stronger than the first signal and thus the second position is closer to the physiological structure than the first position. The first position may be spatially closer, or the first position may have fewer intervening elements and/or structures that reduce the quality of the signal. The method 3800 may include generating an indicator showing which position is closer (block 3814). For example, the processing device may cause the user interface to display a symbol representing the first position and a symbol representing the second position. Once it is determined which position is closer to the physiological structure, the processing device may cause the user interface to signify to the user which position is closer such as by highlighting the symbol corresponding to the closer position.

The signal strength value of the closer position (i.e. the first signal strength value if the first position is closer and the second signal strength value of the second position is closer) may be compared to a minimum signal strength value. The minimum signal strength value may be a minimum threshold below which it cannot be determined that the position is closer than the other position. For example, if the signal strength value associated with the closer position is lower than the minimum threshold, then it may not be possible to determine if the position is closer. Similarly, if the difference between the signal strength values does not meet a minimum threshold, then it may not be possible to determine which position is closer. The minimum signal strength value may be a minimum threshold above which a measurement value can be determined from the signal. In response to the signal strength value being greater than the minimum signal strength value, a physiological characteristic of the subject may be measured by the physiological sensor at the closer position.

Figure 39:
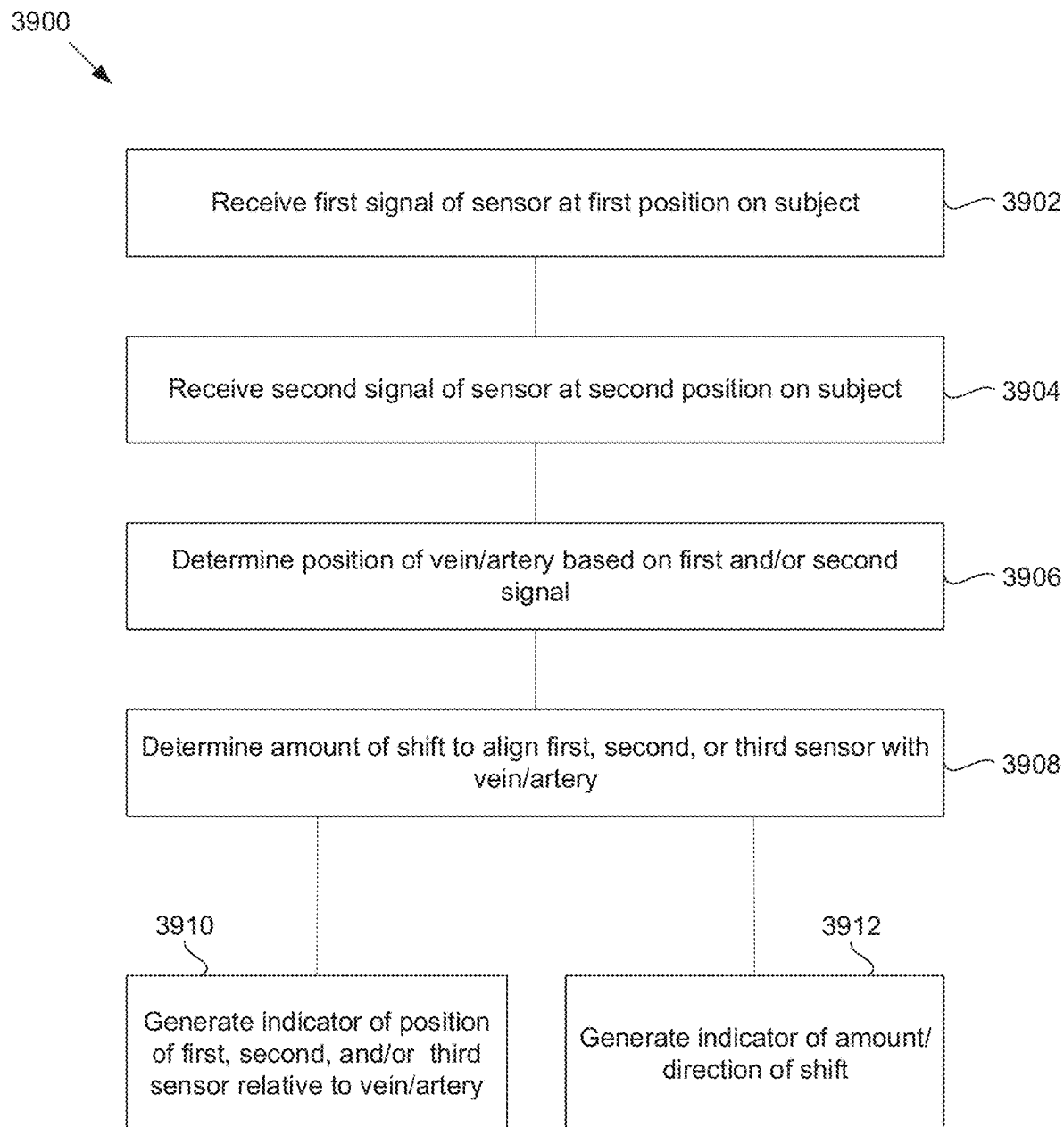
FIG. 39 illustrates a method of determining a shift of the physiological sensor on the subject, according to an embodiment.

FIG. 39 illustrates a method 3900 of determining a shift of the physiological sensor on the subject, according to an embodiment. Some of the features in FIG. 39 may be the same as or similar to some of the features in the other FIGS. described herein as noted by same and/or similar reference characters, unless expressly described otherwise. Additionally, reference may be made to features shown in any of the other FIGS. described herein and not shown in FIG. 39. Elements of the method 3900 may be executed in one or more ways such as by a human, including the subject, by a processing device such as the processing device 102, by mechanisms operating automatically or under human control such as the physiological sensor 206, and so forth.

The method 3900 may include receiving a first signal generated by a first sensor (block 3902). The first sensor may be configured to interrogate a body part of a subject. The first sensor may be positioned at a first position relative to the body part. The first signal may be characterized by a first signal quality (e.g. a first SNR and/or a first amplitude). The method 3900 may include receiving a second signal generated by a second sensor (block 3904). The second sensor may be configured to interrogate the body part. The second sensor may be positioned at a second position relative to the body part. The second position may be different than the first position. The second signal may be characterized by a second signal quality (e.g. a second SNR and/or a second amplitude).

The method 3900 may include determining a first position of a physiological structure within in the body part (e.g. a vein and/or artery) relative to the first sensor and/or the second sensor based on the first signal quality and/or the second signal quality (block 3906). The method 3900 may include determining a shift of the first sensor, the second sensor, and/or a third sensor based on the position of the physiological structure (block 3908). The shift may be an amount the first, second, and/or third sensor should be moved to align the first, second, and/or third sensor with the physiological structure. The method 3900 may include generating a first indicator that indicates whether the first sensor or the second sensor is more closely aligned with the physiological structure (block 3910). The first indicator may indicate a position of the third sensor relative to the physiological structure. The first indicator may indicate that the physiological structure is positioned evenly between the first sensor or the second sensor. The method 3900 may include generating a second indicator that indicates an amount and/or direction of the shift (block 3912). For example, the second indicator may be an arrow presented on a user interface integrated with the measurement device with a number that indicates how much the subject should adjust the position of the measurement device in the direction of the arrow. The second indicator may include a symbol and/or icon that moves on the user interface as the user moves the measurement device. The user interface may display an icon that represents the physiological structure and the second indicator icon may represent the measurement device. As the subject moves the measurement device closer to alignment with the physiological structure, the second indicator may move on the user interface closer to the icon representing the physiological structure.

Figure 40:
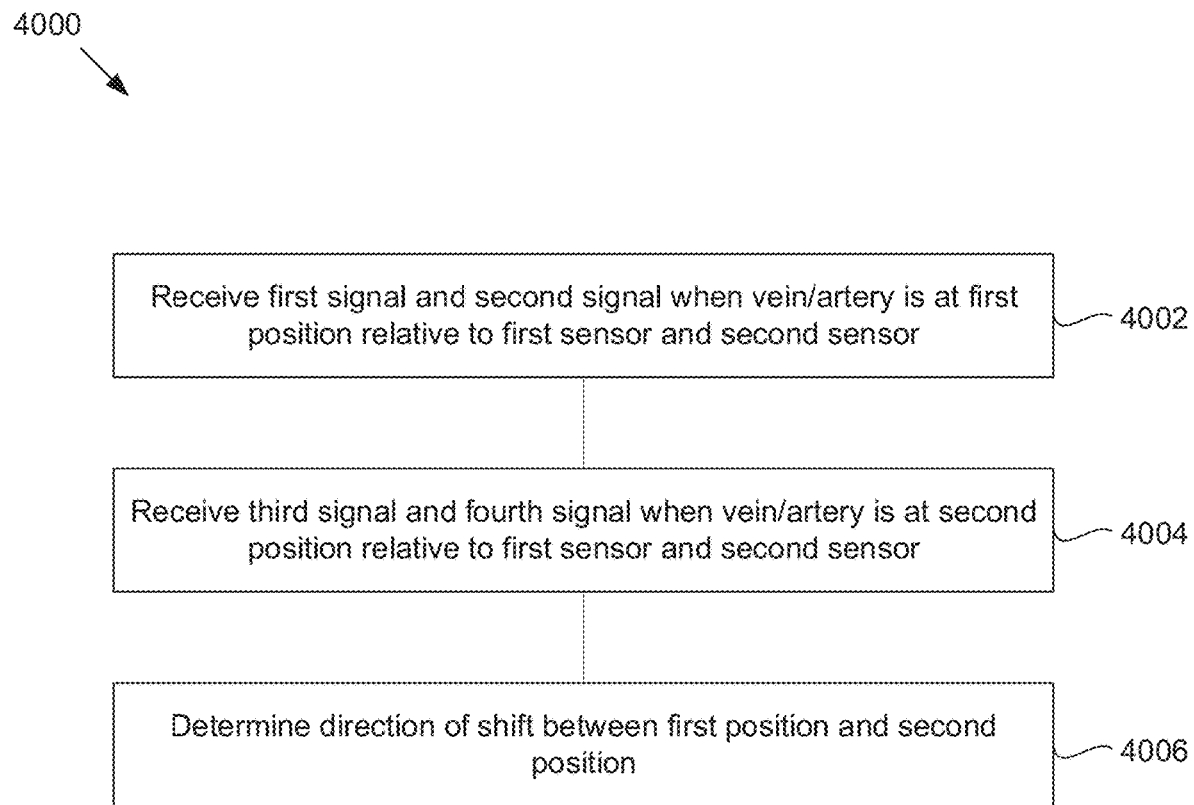
FIG. 40 illustrates a method of determining a direction of the shift of the physiological sensor on the subject, according to an embodiment.

FIG. 40 illustrates a method 4000 of determining a direction of a shift of a physiological sensor on a subject, according to an embodiment. Some of the features in FIG. 40 may be the same as or similar to some of the features in the other FIGS. described herein as noted by same and/or similar reference characters, unless expressly described otherwise. Additionally, reference may be made to features shown in any of the other FIGS. described herein and not shown in FIG. Elements of the method 4000 may be executed in one or more ways such as by a human, including the subject, by a processing device such as the processing device 102, by mechanisms operating automatically or under human control such as the physiological sensor 206, and so forth.

The method 4000 may include receiving a first signal from a first physiological sensor and a second signal from a second physiological sensor when the subject's physiological structure is in a first position relative to the first physiological sensor and the second physiological sensor (block 4002). The first physiological sensor and the second physiological sensor may be incorporated and/or integrated into a measurement device. The position of the measurement device may be adjusted on the subject by moving the measurement device on the subject. The method 4000 may include receiving a third signal from the first physiological sensor and a fourth signal from the second physiological sensor, the third and fourth signals received after receiving the first signal and the second signal (block 4004). The third signal may be characterized by a third signal quality (e.g. a third SNR and/or a third amplitude). The fourth signal may be characterized by a fourth signal quality (e.g. a fourth SNR and/or a fourth amplitude). A second position of the physiological structure relative to the first sensor and/or the second sensor may be determined based on the third signal quality and/or the fourth signal quality. The method 4000 may include determining a direction to shift the measurement device to be in better alignment with the physiological structure based on a difference between the first position and the second position (block 4006).

The method 4000 may be executed to align the physiological structure between two physiological sensors in the measurement device. The first and second signals may indicate the first position is closer to the first physiological sensor than to the second physiological sensor but may not indicate whether the physiological structure is between the two physiological sensors. If the third signal and the fourth signal both decrease in quality when the measurement device is moved, the physiological structure may have been between the sensors at the first position and outside both sensors at the second position. If the third and the fourth signal both increase in quality when the measurement device is moved, the physiological structure may have been outside both sensor at the first position and between the sensor at the second position. If one of the third or the fourth signals increases and the other decreases when the measurement device is moved, the first and second positions of the physiological structure may both be between the first and second physiological sensors. A magnitude of the difference between the third and fourth signal qualities may indicate whether the physiological structure, when at the second position, is aligned more closely to the first physiological sensor, more closely to the second physiological sensor, or approximately evenly between the two physiological sensors.

The above description sets forth numerous specific details such as examples of specific systems, components, methods, and so forth, to provide a good understanding of several implementations. It will be apparent to one skilled in the art, however, that at least some implementations may be practiced without these specific details. In other instances, well-known components or methods are not described in detail or are presented in a simple block diagram format to avoid unnecessarily obscuring the present implementations. Thus, the specific details set forth above are merely exemplary. Particular implementations may vary from these exemplary details and still be contemplated to be within the scope of the present implementations.

It is to be understood that the above description is intended to be illustrative and not restrictive. Many other implementations will be apparent to those of skill in the art upon reading and understanding the above description. The scope of the present implementations should, therefore, be determined regarding the appended claims, along with the full scope of equivalents to which such claims are entitled.

The disclosure above encompasses multiple distinct embodiments with independent utility. While these embodiments have been disclosed in a particular form, the specific embodiments disclosed and illustrated above are not to be considered in a limiting sense as numerous variations are possible. The subject matter of the embodiments includes the novel and non-obvious combinations and sub-combinations of the various elements, features, functions and/or properties disclosed above and inherent to those skilled in the art pertaining to such embodiments. Where the disclosure or subsequently filed claims recite "a" element, "a first" element, or any such equivalent term, the disclosure or claims is to be understood to incorporate one or more such elements, neither requiring nor excluding two or more of such elements.

Applicant(s) reserves the right to submit claims directed to combinations and sub-combinations of the disclosed embodiments that are believed to be novel and non-obvious. Embodiments embodied in other combinations and sub-combinations of features, functions, elements and/or properties may be claimed through amendment of those claims or presentation of new claims in the present application or in a related application. Such amended or new claims, whether they are directed to the same embodiment or a different embodiment and whether they are different, broader, narrower, or equal in scope to the original claims, are to be considered within the subject matter of the embodiments described herein.

The invention claimed is:

1. A system, comprising:
a wearable hand that is wearable by a subject, the wearable band comprising an inside surface that rests against the subject as the subject wears the wearable band;
a first physiological sensor coupled to the wearable band, wherein the first physiological sensor is:
    positioned adjacent to the inside surface of the wearable band;
    embedded in the wearable band; or
    positioned in the wearable band adjacent to the subject as the subject wears the wearable band;
a second physiological sensor coupled to the wearable band, wherein the second physiological sensor is:
    comprised of:
        a substrate;
        a plurality of intermediate layers composed of at least one of a conductive layer, an insulating layer, and/or a catalyst layer;
        parallel rows of microelectrodes composed of nanotube bundles; and
        interstitial filler forming a continuous surface around the top surface of at least one of the parallel rows of microelectrodes and with the inside surface of the flexible band; and
    embedded in the wearable band;
a pressure sensor coupled to the wearable band, wherein the pressure sensor is:
    positioned in the wearable band between the first physiological sensor and the wearable band such that the pressure sensor is positioned to measure a pressure with which the first physiological sensor and/or second physiological sensor is pressed into the wearable band; or
    integrated into the wearable band such that the pressure sensor is positioned to measure a strain in the wearable band;
a processor electronically or communicatively coupled to the first physiological sensor, the second physiological sensor and the pressure sensor, wherein the processor is configured to:
    receive an electronic signal from the pressure sensor corresponding to the pressure on the first physiological sensor and/or second physiological sensor or the strain in the wearable band;
    generate a pressure measurement value representative of the pressure or the strain;
    compare the pressure measurement value to a first range of pressure values from a minimum pressure value to a maximum pressure value; and
    generate an alert when the pressure measurement value is outside the first range of pressure values; and
a user interface electronically or communicatively coupled to the processor, wherein the user interface is configured to:
    receive the alert from the processor;
    generate an indicator for the alert; and
    present the indicator to the subject.

2. The system of claim 1, wherein:
the indicator comprises a visual indicator or an audible indicator;
the indicator notifies the subject whether the pressure measurement value is above the maximum pressure value or below the minimum pressure value;
the indicator notifies the subject of an amount by which the pressure measurement value is outside the first range of pressure values;
the indicator instructs the subject to increase the pressure on the first physiological sensor or decrease the pressure on the first physiological sensor; or
the indicator instructs the subject to tighten the wearable band or loosen the wearable band.

3. The system of claim 1, wherein the processor is further configured to:
take a physiological measurement by the first physiological sensor when the pressure measurement value is within the first range of pressure values;
in response to the pressure measurement value being outside the first range of pressure values, skip taking the physiological measurement; or
in response to the pressure measurement value being outside the first range of pressure values, removing the pressure measurement value from a data set of pressure measurement values.

4. The system of claim 1, wherein the processor is further configured to:
take a physiological measurement by the first physiological sensor; or
in response to the pressure measurement value being outside the first range of pressure values, tag the physiological measurement as possibly inaccurate or inaccurate.

5. The system of claim 1, wherein the processor is further configured to:
take a physiological measurement by the first physiological sensor at approximately a same time as the pressure or strain is measured;
correlate a change in the pressure measurement value from one or more of a set of previous pressure measurement values with a change in the physiological measurement value from one or more of a set of previous physiological measurement values; or
generate a prediction of future change between the physiological measurement value and one or more of a set of future physiological measurement values correlated to one or more of a set of possible future pressure measurement values.

6. The system of claim 1, wherein the processor is further configured to:
take a physiological measurement by the first physiological sensor approximately concurrently with a pressure measurement that yields the pressure measurement value;
receive a validation measurement from a measurement device, wherein the validation measurement is a same type as the physiological measurement;
in response to the pressure measurement value falling outside the first range of pressure values and the physiological measurement being validated by the validation measurement, adjusting the first range of pressure values to include the pressure measurement value; or
in response to the pressure measurement value falling within the first range of pressure values and the physiological measurement not being validated by the validation measurement, adjusting the first range of pressure values to exclude the pressure measurement value.

7. The system of claim 1, wherein the processor is further configured to:
- take a physiological measurement by the second physiological sensor approximately concurrently with a pressure measurement that generates the pressure measurement value; and
- compare the pressure measurement value to a second range of pressure values, wherein the second range of pressure values is different than the first range of pressure values.

8. A method, comprising:
- receiving a first physiological measurement value, the first physiological measurement being determined based at least in part on data from a first physiological sensor located in a band of a wearable device;
- determining whether the first physiological measurement value falls within a first range of first physiological values from a minimum first physiological value to a maximum first physiological value, wherein a first measurement device is enabled, when the first physiological measurement value is within the first range of first physiological values, to interrogate a body part of the subject without distorting a physiological measurement generated by a second measurement device;
- generating:
  - an alert when the first physiological measurement value is outside the first range of first physiological values;
  - an adjustment recommendation that recommends an adjustment to a subject's activity; or
  - an indicator of the alert or the activity recommendation; and
  - presenting the indicator to the subject;
- receiving the first physiological measurement or a second physiological measurement value, the second physiological measurement being determined based at least in part on data from a second physiological sensor located in the band of the wearable device;
- determining whether the first or second physiological measurement value falls within a first or second range of second physiological values from a minimum first or second physiological value to a maximum first or second physiological value, wherein a second measurement device is enabled, when the first or second physiological measurement value is within the first or second range of second physiological values, to interrogate a body part of the subject without distorting a physiological measurement generated by the first measurement device;
- generating:
  - an alert when the first or second physiological measurement value is outside the first or second range of second physiological values;
  - an adjustment recommendation that recommends an adjustment to a subject's activity; or
  - an indicator of the alert or the activity recommendation; and
  - presenting the indicator to the subject;
- receiving a pressure measurement value of a tightness of a wearable device on a subject, the pressure measurement being determined based at least in part on data from a pressure sensor located in the band of the wearable device;
- determining whether the pressure measurement value falls within a first range of pressure values from a minimum pressure value to a maximum pressure value, wherein a first measurement device is enabled, when the pressure measurement value is within the first range of pressure values, to interrogate a body part of the subject without distorting a physiological measurement generated by the first measurement device;
- generating:
  - an alert when the pressure measurement value is outside the first range of pressure values;
  - an adjustment recommendation that recommends an adjustment to the tightness of the wearable device on the subject; or
  - an indicator of the alert or the adjustment recommendation; and
  - presenting the indicator to the subject.

9. The method of claim 8, further comprising, in response to the pressure measurement value being below the first range of pressure values, automatically increasing the tightness of the wearable device on the subject, wherein the tightness is automatically adjusted by an electromechanical device.

10. The method of claim 8, further comprising determining the first range of pressure values, wherein:
- the first measurement device corresponds to a first subrange of pressure values;
- the first range of pressure values is an overlap of pressure values between the first subrange of pressure values and a second subrange of pressure values;
- a second measurement device integrated with the wearable device corresponds to the second subrange of pressure values; and
- the first subrange of pressure values and the second subrange of pressure values overlap from the maximum pressure value to the minimum pressure value.

11. The method of claim 8, further comprising automatically adjusting the tightness of the wearable device on the subject, wherein:
- the wearable device comprises a measurement device that corresponds to a second range of pressure values, wherein the first range of pressure values is different from the second range of pressure values;
- the tightness of the wearable device is automatically adjusted to fall within the first range of pressure values in response to the first measurement device taking a first measurement; or
- the tightness of the wearable device is automatically adjusted to fall within the second range of pressure values in response to the second measurement device taking a second measurement.

12. The method of claim 8, further comprising:
- receiving a set of signals corresponding to a set of physiological measurements taken by the first measurement device;
- determining signal-to-noise ratios for the signals; and
- in response to a subset of the signals having a signal-to-noise ratio below a threshold ratio, generating the alert or the adjustment recommendation based on the pressure measurement value relative to the range of pressure values.

13. The method of claim 8, further comprising:
- receiving a set of signals corresponding to a set of physiological measurements taken by the first measurement device;
- determining signal-to-noise ratios for the signals; and
- in response to a subset of consecutive signals taken during a length of time having a signal-to-noise ratio below a threshold ratio, generating the alert or the adjustment recommendation based on the pressure measurement value relative to the range of pressure values.

14. The method of claim 8, further comprising:
in response to the pressure measurement value falling outside the range of pressure values, skipping taking the physiological measurement at a time when the physiological measurement is set to be taken; and
in response to a threshold number of physiological measurements being skipped, generating the alert or the adjustment recommendation.

15. A method, comprising:
receiving a physiological measurement value, the physiological measurement being determined based at least in part on data from a physiological sensor located in a band of the wearable device;
determining whether the physiological measurement value falls within a range of physiological values from a minimum physiological value to a maximum physiological value, wherein a measurement device is enabled, when the physiological measurement value is within a range of pressure values, to interrogate a body part of the subject without distorting a physiological measurement generated by the measurement device;
generating:
an alert when the physiological measurement value is outside a range of physiological values;
an adjustment recommendation that recommends an adjustment to a subject's activity; or
an indicator of the alert or the activity recommendation; and presenting the indicator to the subject;
receiving a pressure measurement value of a pressure of the measurement device against a subject, wherein:
the measurement device is integrated into a band of a wearable device that is worn by the subject; and
the measurement device is pressed against the subject as the subject wears the wearable device;
determining whether the pressure measurement value falls within a range of pressure values from a minimum pressure value to a maximum pressure value;
in response to the measurement value being within the range of pressure values, enabling another device to interrogate a body part of the subject without distorting a physiological measurement generated by the measurement device;
in response to the pressure measurement value being outside the range of pressure values:
tagging the physiological measurement value as possibly inaccurate or inaccurate;
skipping taking the physiological measurement; or removing the pressure measurement value from a data set of pressure measurement values; and
in response to the pressure measurement value falling within the range of pressure values, enabling the measurement device to interrogate a body part of the subject without distorting a physiological measurement generated by the measurement device.

16. The method of claim 15, further comprising:
in response to the pressure measurement value falling outside the range of pressure values, skipping taking the physiological measurement at a time when the physiological measurement is set to be taken; and
generating an indicator that indicates the physiological measurement was skipped; and
presenting the indicator to the subject.

17. The method of claim 15, in response to the pressure measurement value falling outside the range of pressure values, generating a tag that indicates the physiological measurement may be inaccurate.

18. The method of claim 15, further comprising adding a tag to a bad physiological measurement, wherein the bad physiological measurement corresponds to a signal generated by the measurement device having a signal-to-noise ratio below a threshold level.

19. The method of claim 15, further comprising:
generating a graphical display showing a set of physiological measurement values taken over a length of time; and
generating an overlay on the graphical display showing a set of pressure measurement values taken over the length of time; and
presenting the graphical display with the overlay to the subject.

20. The method of claim 19, wherein:
the overlay shows the set of pressure measurement values relative to the range of pressure values;
a subset of pressure measurement values is shown on the graphical display by a first visual cue that indicates the subset of pressure measurement values are outside the range of pressure values; and
a subset of physiological measurement values is shown on the graphical display by a second visual cue that indicates the subset of physiological measurement values corresponds to the subset of pressure measurement values.

* * * * *